US010323010B2

(12) United States Patent
Storey et al.

(10) Patent No.: US 10,323,010 B2
(45) Date of Patent: Jun. 18, 2019

(54) METHODS OF CHEMICAL SYNTHESIS OF SUBSTITUTED 10H-PHENOTHIAZINE-3,7-DIAMINE COMPOUNDS

(71) Applicant: WisTa Laboratories Ltd., Singapore (SG)

(72) Inventors: John Mervyn David Storey, Old Aberdeen (GB); Christopher Paul Larch, Old Aberdeen (GB); Steven John Kemp, Old Aberdeen (GB); Scott Clunas, Old Aberdeen (GB); Sarah Louise Nicoll, Old Aberdeen (GB); Helen Sarah Gibbard, Old Aberdeen (GB); Michael Simpson, Old Aberdeen (GB); James Peter Sinclair, Old Aberdeen (GB); Colin Marshall, Old Aberdeen (GB)

(73) Assignee: WISTA LABORATORIES LTD., Singapore (SG)

( * ) Notice: Subject to any disclaimer, the term of this patent is extended or adjusted under 35 U.S.C. 154(b) by 0 days.

(21) Appl. No.: 15/746,338

(22) PCT Filed: Jul. 20, 2016

(86) PCT No.: PCT/EP2016/067302
§ 371 (c)(1),
(2) Date: Jan. 19, 2018

(87) PCT Pub. No.: WO2017/013174
PCT Pub. Date: Jan. 26, 2017

(65) Prior Publication Data
US 2018/0208565 A1    Jul. 26, 2018

(30) Foreign Application Priority Data
Jul. 20, 2015 (GB) .................................. 1512678.2

(51) Int. Cl.
*C07D 279/20* (2006.01)
(52) U.S. Cl.
CPC ................... *C07D 279/20* (2013.01)
(58) Field of Classification Search
CPC ................................................. C07D 279/20
USPC .......................................................... 544/37
See application file for complete search history.

(56) References Cited

U.S. PATENT DOCUMENTS

2010/0204215 A1    8/2010  Galey et al.
2013/0315992 A1   11/2013  Clunas et al.

FOREIGN PATENT DOCUMENTS

AU      2013200732 A1    2/2013
DE         43 02 013 C1   6/1994
WO       WO-96/30766 A1  10/1996
WO       WO-01/51479 A2   7/2001
WO       WO-02/055720 A2  7/2002
WO     WO-2005/030676 A1   4/2005
WO     WO-2007/110627 A2  10/2007
WO     WO-2007/110630 A1  10/2007
WO     WO-2008/007074 A2   1/2008
WO     WO-2012/107706 A1   8/2012
WO     WO-2012/135402 A1  10/2012

OTHER PUBLICATIONS

Bondareff et al., "Immunohistochemical Staging of Neurofibrillary Degeneration in Alzheimer's Disease," Journal of Neuropathology and Experimental Neurology, vol. 53, No. 2, 1994, pp. 158-164.
Epstein et al., "Spectrophotometric Study of Thionine," J. Opt. Soc. Am., vol. 31, 1941, pp. 77-84.
Goedert et al., "Cloning and sequencing of the cDNA encoding an isoform of microtubule-associated protein tau containing four tandem repeats: differential expression of tau protein mRNAs in human brain," The EMBO Journal, vol. 8, No. 2, 1989, pp. 393-399.
Goedert et al., "Multiple Isoforms of Human Microtubule-Associated Protein Tau: Sequences and Localization in Neurofibrillary Tangles of Alzheimer's Disease," Neuron, vol. 3, 1989, pp. 519-526.
Guttmann and Ehrlich, "On the Effect of Methylene Blue on Malaria," Berlin Clinical Weekly, vol. 28, 1891, pp. 953-956 with English translation.
International Preliminary Report on Patentability issued in corresponding application No. PCT/EP2016/067302 dated Jan. 23, 2016.
International Search Report and Written Opinion issued in corresponding application No. PCT/EP2016/067302 dated Oct. 18, 2016.
Jakes et al., "Identification of 3- and 4-repeat tau isoforms within the PHF in Alzheimer's disease," The EMBO Journal, vol. 10, No. 10, 1991, pp. 2725-2729.
Jung et al., "An efficient conversion of nitroaromatics and aromatic amines to tertiary amines in one-pot way," Tetrahedron, vol. 59, 2003, pp. 10331-10338.
Kang et al., "The precursor of Alzheimer's disease amyloid A4 protein resembles a cell-surface receptor," Nature, vol. 325, 1987, pp. 733-736.

(Continued)

*Primary Examiner* — Kahsay Habte
(74) *Attorney, Agent, or Firm* — Foley & Lardner LLP

(57) ABSTRACT

The present invention pertains generally to the field of chemical synthesis, and more particularly to methods of chemical synthesis which include the step of preparing a substituted 10H-phenothiazine-3,7-diamine compound of Formula (1) by a step of selective alkylation by reductive amination, in which the corresponding unsubstituted diamine of Formula (4) is reacted with aldehyde/ketone, under reductive amination conditions. The present invention also relates to such methods which incorporate additional subsequent and/or preceding steps, for example, to prepare compounds of Formulae (2) and (3) from compounds of Formula (1), and to prepare compounds of Formula (4) from, for example, compounds of Formulae (5), (6), (7), (8), and (9). Compounds of Formula (1), Formula (2), and Formula (3) are useful, for example, in the treatment of diseases of protein aggregation, such as Alzheimer's disease.

23 Claims, 3 Drawing Sheets

(56) References Cited

OTHER PUBLICATIONS

Lai et al., "Examination of Phosphorylated Tau Protein as a PHF-Precursor at Early Stage Alzheimer's Disease," Neurobiology of Aging, vol. 16, No. 3, 1995, pp. 443-445.
May et al., "Reduction and uptake of methylene blue by human erythrocytes," Am J Physiol Cell Physiol, vol. 286, 2004, pp. C1390-C1398.
Mena et al., "Monitoring pathological assembly of tau and B-amyloid proteins in Alzheimer's disease," Acta Neuropathol, vol. 89, 1995, pp. 50-56.
Mena et al., "Staging the pathological assembly of truncated tau protein into paired helical filaments in Alzheimer's disease," Acta Neuropathol, vol. 91, 1996, pp. 633-641.
Michaelis et al., "Semiquinone Radicals of the Thiazines," J. Am. Chem. Soc., vol. 62, 1940, pp. 204-211.
Mukaetova-Ladinska et al., "Biochemical and Anatomical Redistribution of Tau Protein in Alzheimer's Disease," American Journal of Pathology, vol. 143, No. 2, 1993, pp. 565-578.
Mukaetova-Ladinska et al., "Staging of Cytoskeletal and B-Amyloid Changes in Human Isocortex Reveals Biphasic Synaptic Protein Response during Progression of Alzheimer's Disease," American Journal of Pathology, vol. 157, No. 2, 2000, pp. 623-636.
Novak et al., "Molecular characterization of the minimal protease resistant tau unit of the Alzheimer's disease paired helical filament," The EMBO Journal, vol. 12, No. 1, 1993, pp. 365-370.
Rengelshausen et al., "Pharmacokinetic interaction of chloroquine and methylene blue combination against malaria," Eur J Clin Pharmacol, vol. 60, 2004, pp. 709-715.
Schirmer et al., "Methylene blue as an antimalarial agent," Redox Report, vol. 8, No. 5, 2003, pp. 272-275.
Search Report issued in corresponding Great Britain application No. GB 1512678.2 dated Apr. 4, 2016.
Tomilin et al., "Cation Radicals of N-Substituted Phenothiazines," Chemistry of Heterocyclic Compounds, vol. 32, No. 3, 1996, pp. 365-370.
Tomilin et al., "Synthesis and Properties of Phenothiazine Derivatives," Chemistry of Heterocyclic Compounds, vol. 32, No. 9, 1996, pp. 1105-1108.
Wildes et al., "Correlation of Open-Circuit Voltage and Short-Circuit Current of the Totally Illuminated, Thin-Layer Iron-Thionine Photogalvanic Cell with Photostationary Composition," Journal of the American Chemical Society, vol. 100, No. 21, 1978, pp. 6568-6572.
Wischik et al., "Brain microtubule-associated proteins: modifications in disease," Eds. J. Avila, R. Brandt and K. S. Kosik (Harwood Academic Publishers, Amsterdam, 1997, pp. 185-241.
Wischik et al., "Isolation of a fragment of tau derived from the core of the paired helical filament of Alzheimer's disease," Proc. Natl. Acad. Sci., vol. 84, 1988, pp. 4506-4510.
Wischik et al., "Neurobiology of Alzheimer's Disease," D. Dawbarn and S. J. Allen (The Molecular and Cellular Neurobiology Series, Bios Scientific Publishers, Oxford, 2nd Edition, 2001.
Wischik et al., "Selective inhibition of Alzheimer disease-like tau aggregation by phenothiazines," Proc. Natl. Acad. Sci., vol. 93, 1996, pp. 11213-11218.
Wischik et al., "Structural characterization of the core of the paired helical filament of Alzheimer disease," Proc. Natl. Acad. Sci., vol. 85, 1988, pp. 4884-4888.

Hydrogen uptake (%) - - -
Temperature (°C) ———
Pressure (bar) - · - -

METHODS OF CHEMICAL SYNTHESIS OF SUBSTITUTED 10H-PHENOTHIAZINE-3,7-DIAMINE COMPOUNDS

CROSS REFERENCE TO RELATED APPLICATIONS

The present application is a national stage entry of International Patent Application no. PCT/EP2016/067302, filed Jan. 20, 2016, which claims priority to United Kingdom Patent Application No. 1512678.2, filed Jul. 20, 2015, each of which is incorporated herein by reference in its entirety.

RELATED APPLICATION

This application is related to United Kingdom patent application number 1512678.2 filed 20 Jul. 2015, the contents of which are incorporated herein by reference in their entirety.

TECHNICAL FIELD

The present invention pertains generally to the field of chemical synthesis, and more particularly to methods of chemical synthesis which include the step of preparing a substituted 10H-phenothiazine-3,7-diamine compound of Formula (1) by a step of selective alkylation by reductive amination, in which the corresponding unsubstituted diamine of Formula (4) is reacted with aldehyde/ketone, under reductive amination conditions. The present invention also relates to such methods which incorporate additional subsequent and/or preceding steps, for example, to prepare compounds of Formulae (2) and (3) from compounds of Formula (1), and to prepare compounds of Formula (4) from, for example, compounds of Formulae (5), (6), (7), (8), and (9). See, e.g., FIG. 1. Compounds of Formula (1), Formula (2), and Formula (3) are useful, for example, in the treatment of diseases of protein aggregation, such as Alzheimer's disease.

BACKGROUND

A number of publications are cited herein in order to more fully describe and disclose the invention and the state of the art to which the invention pertains. Each of these references is incorporated herein by reference in its entirety into the present disclosure, to the same extent as if each individual reference was specifically and individually indicated to be incorporated by reference.

Throughout this specification, including the claims which follow, unless the context requires otherwise, the word "comprise," and variations such as "comprises" and "comprising," will be understood to imply the inclusion of a stated integer or step or group of integers or steps but not the exclusion of any other integer or step or group of integers or steps.

It must be noted that, as used in the specification and the appended claims, the singular forms "a," "an," and "the" include plural referents unless the context clearly dictates otherwise. Thus, for example, reference to "a pharmaceutical carrier" includes mixtures of two or more such carriers, and the like.

Ranges are often expressed herein as from "about" one particular value, and/or to "about" another particular value. When such a range is expressed, another embodiment includes from the one particular value and/or to the other particular value. Similarly, when values are expressed as approximations, by the use of the antecedent "about," it will be understood that the particular value forms another embodiment.

This disclosure includes information that may be useful in understanding the present invention. It is not an admission that any of the information provided herein is prior art or relevant to the presently claimed invention, or that any publication specifically or implicitly referenced is prior art.

Any sub-titles herein are included for convenience only, and are not to be construed as limiting the disclosure in any way.

Dementia

Conditions of dementia are frequently characterised by a progressive accumulation of intracellular and/or extracellular deposits of proteinaceous structures such as β-amyloid plaques and neurofibrillary tangles (NFTs) in the brains of affected patients. The appearance of these lesions largely correlates with pathological neurofibrillary degeneration and brain atrophy, as well as with cognitive impairment (see, e.g., Mukaetova-Ladinska et al., 2000). In Alzheimer's disease, both neuritic plaques and NFTs contain paired helical filaments (PHFs), of which a major constituent is the microtubule-associated protein tau (see, e.g., Wischik et al., 1988a). Plaques also contain extracellular β-amyloid fibrils derived from the abnormal processing of amyloid precursor protein (APP) (see, e.g., Kang et al., 1987). An article (Wischik et al., 2001) discusses in detail the putative role of tau protein in the pathogenesis of neurodegenerative dementias. Loss of the normal form of tau, accumulation of pathological PHFs, and loss of synapses in the mid-frontal cortex all correlate with associated cognitive impairment. Furthermore, loss of synapses and loss of pyramidal cells both correlate with morphometric measures of tau-reactive neurofibrillary pathology, which parallels, at a molecular level, an almost total redistribution of the tau protein pool from a soluble to a polymerised form (i.e., PHFs) in Alzheimer's disease (see, e.g., Mukaetova-Ladinska et al., 1993).

Tau exists in alternatively-spliced isoforms, which contain three or four copies of a repeat sequence corresponding to the microtubule-binding domain (see, e.g., Goedert et al., 1989a; Goedert et al., 1989b). Tau in PHFs is proteolytically processed to a core domain (see, e.g., Wischik et al., 1988a; Wischik et al., 1988b; Novak et al., 1993) which is composed of a phase-shifted version of the repeat domain; only three repeats are involved in the stable tau-tau interaction (see, e.g., Jakes et al., 1991). Once formed, PHF-like tau aggregates act as seeds for the further capture and provide a template for proteolytic processing of full-length tau protein (see, e.g., Wischik et al., 1996a).

The phase shift which is observed in the repeat domain of tau incorporated into PHFs suggests that the repeat domain undergoes an induced conformational change during incorporation into the filament. During the onset of AD, it is envisaged that this conformational change could be initiated by the binding of tau to a pathological substrate, such as damaged or mutated membrane proteins (see, e.g., Wischik et al., 1997).

In the course of their formation and accumulation, PHFs first assemble to form amorphous aggregates within the cytoplasm, probably from early tau oligomers which become truncated prior to, or in the course of, PHF assembly (see, e.g., Mena et al., 1995; Mena et al., 1996). These filaments then go on to form classical intracellular NFTs. In this state, the PHFs consist of a core of truncated tau and a fuzzy outer coat containing full-length tau (see, e.g., Wischik et al., 1996a). The assembly process is exponential, consuming the cellular pool of normal functional tau and inducing new tau synthesis to make up the deficit (see, e.g., Lai et al., 1995). Eventually, functional impairment of the neurone progresses to the point of cell death, leaving behind an extracellular NFT. Cell death is highly correlated with the number of extracellular NFTs (see, e.g., Wischik et al., 2001). As tangles are extruded into the extracellular space, there is progressive loss of the fuzzy outer coat of the PHFs with corresponding loss of N-terminal tau immunoreactivity, but preservation of tau immunoreactivity associated with the PHF core (see, e.g., Bondareff et al., 1994).

Methylthioninium Chloride (MTC)

Methythioninium Chloride (MTC) (also known as Methylene blue (MB); methylthionine chloride; tetramethylthionine chloride; 3,7-bis(dimethylamino) phenothiazin-5-ium chloride; C.I. Basic Blue 9; tetramethylthionine chloride; 3,7-bis(dimethylamino) phenazathionium chloride; Swiss blue; C.I. 52015; C.I. Solvent Blue 8; aniline violet; and Urolene Blue®) is a low molecular weight (319.86), water soluble, tricyclic organic compound of the following formula:

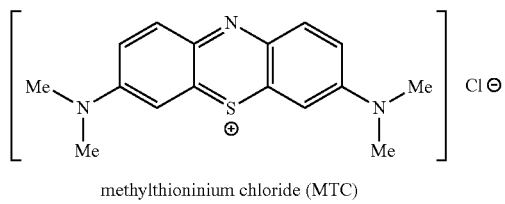

methylthioninium chloride (MTC)

MTC is a well known phenothiazine dye and redox indicator and has also been used as an optical probe of biophysical systems, as an intercalator in nanoporous materials, as a redox mediator, and in photoelectrochromic imaging.

MTC and other diaminophenothiazines have been described as inhibitors of protein aggregation in diseases in which proteins aggregate pathologically.

In particular, diaminophenothiazines including MTC have been shown to inhibit tau protein aggregation and to disrupt the structure of PHFs, and reverse the proteolytic stability of the PHF core (see, e.g., Wischik et al., 1996b). Such compounds were disclosed for use in the treatment or prophylaxis of various diseases, including Alzheimer's disease.

Wischik et al., 2007a discloses certain specific diaminophenothiazine compounds related to MTC which are useful as drugs, for example in the treatment of Alzheimer's disease.

Additionally, Schweiger et al., 2005, discusses radiolabelled phenothiazines, and their use in diagnosis and therapy, for example, of tauopathies.

MTC has also been disclosed for other medical uses. For example it is currently used to treat methemoglobinemia (a condition that occurs when the blood cannot deliver oxygen where it is needed in the body). MTC is also used as a medical dye (for example, to stain certain parts of the body before or during surgery); a diagnostic (for example, as an indicator dye to detect certain compounds present in urine); a mild urinary antiseptic; a stimulant to mucous surfaces; a treatment and preventative for kidney stones; and in the diagnosis and treatment of melanoma.

MTC has been used to treat malaria, either singly (see, e.g., Guttmann and Ehrlich, 1891) or in combination with chloroquine (see, e.g., Schirmer et al., 2003; Rengelshausen et al., 2004).

MTC (under the name Virostat®, from Bioenvision Inc., New York) has also shown potent viricidal activity in vitro. Specifically Virostat® is effective against viruses such as HIV and West Nile Virus in laboratory tests. Virostat® is also currently in clinical trials for the treatment of chronic Hepatitis C, a viral infection of the liver. The virus, HCV, is a major cause of acute hepatitis and chronic liver disease, including cirrhosis and liver cancer.

MTC, when combined with light, can also prevent the replication of nucleic acid (DNA or RNA). Plasma, platelets and red blood cells do not contain nuclear DNA or RNA. When MTC is introduced into the blood components, it crosses bacterial cell walls or viral membrane then moves into the interior of the nucleic acid structure. When activated with light, the compound then binds to the nucleic acid of the viral or bacterial pathogen, preventing replication of the DNA or RNA. Because MTC can inactivate pathogens, it has the potential to reduce the risk of transmission of pathogens that would remain undetected by testing.

Oral and parenteral formulations of MTC have been commercially available in the United States, usually under the name Urolene Blue®.

Leuco Methylthioninium (LMT)

MTC, a phenothiazin-5-ium salt, may be considered to be an "oxidized form" in relation to the corresponding 10H-phenothiazine compound, N,N,N',N'-tetramethyl-10H-phenothiazine-3,7-diamine ("Leuco methylthionine", LMT), which may be considered to be a "reduced form":

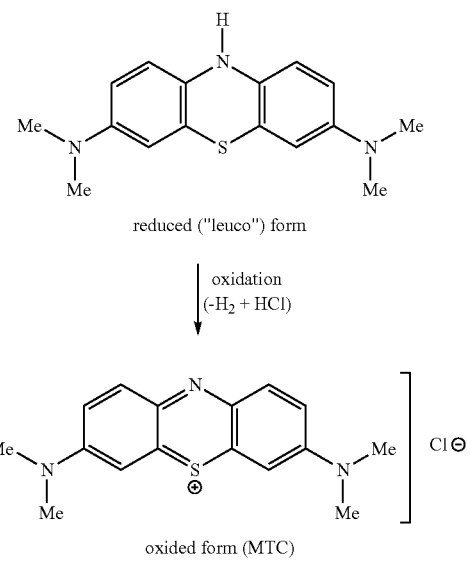

The "reduced form" (or "leuco form"), LMT, is known to be unstable and can be readily and rapidly oxidized to give the corresponding "oxidized" form, e.g., MTC.

It has been shown that human erythrocytes sequentially reduce and take up MTC; that MTC itself is not taken up by the cells; that it is the reduced form of MTC that crosses the cell membrane; that the rate of uptake is enzyme dependent; and that both MTC and reduced MTC are concentrated in cells (LMT, once inside the cell oxidises to MT+ and an equilibrium is established). See, e.g., May et al., 2004.

MTC and similar drugs are taken up in the gut and enter the bloodstream. Unabsorbed drug percolates down the alimentary canal, to the distal gut. One important undesired side-effect is the effect of the unabsorbed drug in the distal gut, for example, sensitisation of the distal gut and/or antimicrobial effects of the unabsorbed drug on flora in the distal gut, both leading to diarrhoea. Therefore, it is desirable to minimize the amount of drug that percolates to the distal gut. By increasing the drug's uptake in the gut (i.e., by increasing the drug's bioavailability), dosage may be reduced, and the undesired side-effects, such as diarrhoea, may be ameliorated. Since it is the reduced form of MTC that is taken up by cells, it may be desirable to administer the reduced form to patients. This may also reduce reliance on the rate limiting step of enzymatic reduction.

Wischik et al., 2002 describes the use of reduced forms of certain diaminophenothiazines for the treatment of protein aggregating diseases, primarily tauopathies.

Wischik et al., 2007b describes certain 10H-phenothiazine-3,7-diaminium salts, effective as drugs or pro-drugs for the treatment of diseases including Alzheimer's disease. These compounds are also in the "reduced" or "leuco" form when considered in respect of MTC. Among the examples described therein are the di-HCl salt (LMT.2HCl), the di-HBr salt (LMT.2HBr), and the di-HI salt (LMT.2HI).

Wischik et al., 2012 describe further 10H-phenothiazine-3,7-diaminium salts, including certain sulfonate salts, effective as drugs or pro-drugs for the treatment of diseases including Alzheimer's disease. Among the examples described therein are the di-mesylate salt (LMT.2MsOH; LMTM), the di-edisylate salt (LMT.2EsOH), the di-tosylate salt (LMT.2TsOH), the di-benzenesulfonate salt (LMT.2BSA), the ethanedisulfonate salt (LMT.EDSA), the propanedisulfonate salt (LMT.PDSA), and the naphth-1,7-di-sulfonate salt (LMT.NDSA).

Galey et al., 2010, describes certain 10H-phenothiazine-2,8-diamine compounds of the following formula which allegedly have biocidal activity and are useful in the agro-food industry and in the treatment of effluent. The document describes methods for preparing the 10H-phenothiazine-2,8-diamine compounds using a step of cross-coupling of anilines and halo benzenes followed by sulphur insertion and phenothiazine ring formation. According to the general teaching provided therein, the substituents on the pendant amino groups (i.e., —$R_{2a}$, —$R_{2b}$, —$R_{8a}$, —$R_{8b}$) may be present throughout synthesis (i.e., may be present before cross-coupling and phenothiazine ring formation) or may be added later, after phenothiazine ring formation, by alkylation, reductive amination, or acylation. However, in all of the worked examples, only the first method was used; that is, the substituents on the pendant amino groups, if present, were already attached before the cross-coupling reaction was carried out. Despite the lack of worked examples, and without any supporting evidence, the authors appear to allege that the proposed addition of substituents on the pendant amino groups after phenothiazine ring formation, according to the second method, would be selective for the pendant amino groups over the ring nitrogen that forms part of the phenothiazine ring (see, e.g., paragraph [0182] therein).

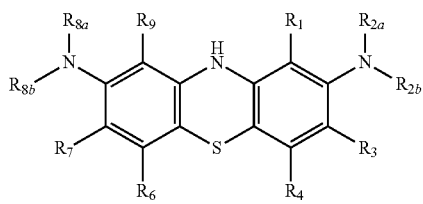

Booth et al., 2001, describes methods of preparing a range of tricyclic compounds of the following formula which allegedly have anti-viral activity. A small number of compounds were prepared using "singleton synthesis" and characterised; however, none of these compounds is a phenothiazine. See, e.g., pages 98-101 therein. A large number of compounds were prepared using "combinatorial chemistry synthesis" by reductive amination of a suitable amine using an aldehyde/ketone and sodium triacetoxyborohydride. See, e.g., pages 10-15 therein. The combinatorial products were characterised by mass spectrometry only, and chemical structures were tentatively assigned accordingly, without further supporting evidence. No yields were reported. Of the 458 compounds listed on pages 21-35 therein and the 446 compounds shown in the table at pages 36-98 therein, only 20 compounds are phenothiazines (i.e., Examples 88, 89, 324, and 415-431). However, each one is a 10H-phenothiazine-2-amine, and not a 10H-phenothiazine-3,7-diamine.

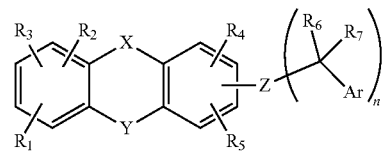

Improved Methods of Synthesis

It is generally desirable that chemical compounds which are intended to be used as pharmaceuticals are provided in a form that is sufficiently free of undesired impurities. This is especially true for chemical compounds that are intended to be used as part of long-term therapy, for example, daily administration for a period of months or years (or, indeed, indefinitely).

The presence of even relatively small amounts of certain undesirable impurities can render a chemical compound unacceptable for use in therapy, for example, accordingly the specifications set by national regulatory bodies (e.g., the US Food and Drug Administration, the European Medicines Agency, etc.).

Among the many undesired impurities are certain metals, including especially chromium (Cr). It is often extremely difficult to remove these metal impurities from a chemical compound that has been prepared by a method of chemical synthesis which used them.

For example, a method of chemical synthesis which employs, as an oxidizing agent, a chromium compound (e.g., chromate, $CrO_4^{2-}$; dichromate, $Cr_2O_7^{2-}$) often yields a product with residual chromium, which cannot easily (or at all) be reduced to acceptable levels.

As discussed above, thioninium salts (such as MTC), thionines (such as LMT), and thionine di-salts (such as LMT.2EsOH) have utility in the long-term treatment of chronic conditions (such as Alzheimer's disease) and accordingly must be provided in a form with extremely low metal (including, e.g., chromium) content.

Such compounds are conventionally prepared by methods of chemical synthesis which involve one or more oxidation steps which use chromium-based oxidizing agents. Consequently, the resulting product must undergo substantial purification in order to reduce the chromium content to acceptable levels.

Accordingly, there is a need for alternative methods of chemical synthesis of such thionine/thioninium compounds which avoid the need to use such metal-based (e.g., chromium-based) oxidizing agents.

The inventors have identified such methods, which are described herein. For example, thionine compounds of Formula (1) (such as LMT), thionine di-salt compounds of Formula (2) (such as LMT.2EsOH), and thioninium compounds of Formula (3) (such as MTC) can be prepared by methods which avoid the use of chromium oxidizing agents.

More specifically, the methods described herein include a step of preparing a substituted 10H-phenothiazine-3,7-diamine compound of Formula (1) by a step of selective alkylation by reductive amination, in which the corresponding unsubstituted diamine of Formula (4) is reacted with aldehyde/ketone, under reductive amination conditions.

Surprisingly and unexpectedly, the alkylation by reductive amination is selective, that is, the alkylation is selective for the pendant amino groups at the 3- and 7-positions in compounds of Formula (4), as compared to the bridging amino group at the 10-position in compounds of Formula (4). Surprisingly and unexpectedly, alkylation by reductive amination preferentially occurs at the pendant amino groups at the 3- and 7-positions, even to the point of di-alkylation at both of those positions, with little or no alkylation occurring at the bridging amino group at the 10-position.

Consequently (and surprisingly and unexpectedly), compounds of Formula (1) can be obtained in good yield without the use of chromium oxidizing agents, and thus without the need for further purification to remove residual chromium.

SUMMARY OF THE INVENTION

The present invention relates to methods for the chemical synthesis which include the step of preparing a substituted 10H-phenothiazine-3,7-diamine compound of Formula (1) by a step of selective alkylation by reductive amination, in which the corresponding unsubstituted diamine of Formula (4) is reacted with aldehyde/ketone, under reductive amination conditions.

Accordingly, one aspect of the invention is a method of chemical synthesis of a compound of Formula (1):

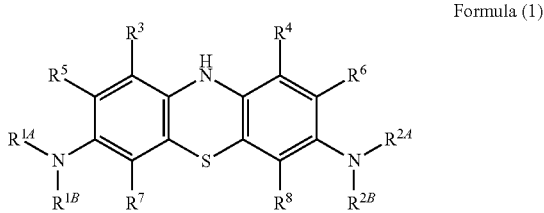

Formula (1)

comprising the step of:
reductive amination, in which a compound of Formula (4):

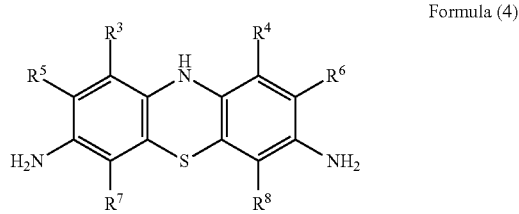

Formula (4)

is reacted with aldehyde/ketone and a reductive amination agent, under reductive amination conditions,
to give the corresponding compound of Formula (1),
wherein a carbonyl group, (O=)C<, of the aldehyde/ketone gives rise to a corresponding nitrogen substituent, –CH<;
wherein:
  $R^{1A}$ is independently a substituent with one point of attachment, wherein the attachment is via a —CH< group; and
  $R^{1B}$ is independently H or a substituent with one point of attachment, wherein the attachment is via a —CH< group;
or
  $R^{1A}$ and $R^{1B}$, taken together, form a substituent with two points of attachment, wherein each of the attachments is via a —CH< group;
  $R^{2A}$ is independently a substituent with one point of attachment, wherein the attachment is via a —CH< group; and
  $R^{2B}$ is independently H or a substituent with one point of attachment, wherein the attachment is via a —CH< group;
or
  $R^{2A}$ and $R^{2B}$, taken together, form a substituent with two points of attachment, wherein each of the attachments is via a —CH< group;
and wherein:
  $R^3$ is independently —H, —$R^{T3}$, —$R^{T3H}$, —F, —Cl, —Br, —I, —OH, —$OR^{T3}$, —$NH_2$, —$NHR^{T3}$, —$NR^{T3}{}_2$, pyrrolidino, piperidino, morpholino, —C(=O)OH, or —C(=O)$OR^{T3}$; wherein each —$R^{T3}$ is a $C_{1-10}$alkyl group and $R^{T3H}$ is a $C_{1-10}$haloalkyl group; and
  $R^4$ is independently —H, —$R^{T4}$, —$R^{T4H}$, —F, —Cl, —Br, —I, —OH, —$OR^{T4}$, —$NH_2$, —$NHR^{T4}$, —$NR^{T4}{}_2$, pyrrolidino, piperidino, morpholino, —C(=O)OH, or —C(=O)$OR^{T4}$; wherein each —$R^{T4}$ is a $C_{1-10}$alkyl group and $R^{T4H}$ is a $C_{1-10}$haloalkyl group;
and wherein:
  $R^5$ is independently —H, —$R^{T5}$, —$R^{T5H}$, —F, —Cl, —Br, —I, —OH, —$OR^{T5}$, —$NH_2$, —$NHR^{T5}$, —$NR^{T5}{}_2$, pyrrolidino, piperidino, morpholino, —C(=O)OH, or —C(=O)$OR^{T5}$; wherein each —$R^{T5}$ is a $C_{1-10}$alkyl group and $R^{T5H}$ is a $C_{1-10}$haloalkyl group; and
  $R^6$ is independently —H, —$R^{T6}$, —$R^{T6H}$, —F, —Cl, —Br, —I, —OH, —$OR^{T6}$, —$NH_2$, —$NHR^{T6}$, —$NR^{T6}{}_2$, pyrrolidino, piperidino, morpholino, —C(=O)OH, or —C(=O)$OR^{T6}$; wherein each —$R^{T6}$ is a $C_{1-10}$alkyl group and $R^{T6H}$ is a $C_{1-10}$haloalkyl group;
and wherein:
  $R^7$ is independently —H, —$R^{T7}$, —$R^{T7-1}$, —F, —Cl, —Br, —I, —OH, —$OR^{T7}$, —$NH_2$, —$NHR^{T7}$, —$NR^{T7}{}_2$, pyrrolidino, piperidino, morpholino, —C(=O)OH, or —C(=O)$OR^{T7}$; wherein each —$R^{T7}$ is a $C_{1-10}$alkyl group and $R^{T7H}$ is a $C_{1-10}$haloalkyl group; and
  $R^8$ is independently —H, —$R^{T8}$, —$R^{T8H}$, —F, —Cl, —Br, —I, —OH, —$OR^{T8}$, —$NH_2$, —$NHR^{T8}$, —$NR^{T8}{}_2$, pyrrolidino, piperidino, morpholino, —C(=O)OH, or —C(=O)$OR^{T8}$; wherein each —$R^{T8}$ is a $C_{1-10}$alkyl group and $R^{T8H}$ is a $C_{1-10}$haloalkyl group.

The present invention also relates to such methods which incorporate additional subsequent and/or preceding steps, for example, to prepare compounds of Formulae (2) and (3) from compounds of Formula (1), and to prepare compounds of Formula (4) from, for example, compounds of Formulae (5), (6), (7), (8), and (9). See, e.g., FIG. 1.

Another aspect of the present invention pertains to a compound of Formula (1), Formula (2), or Formula (3), as described herein, which is obtained by a method of synthesis as described herein, or a method comprising a method of synthesis as described herein.

Another aspect of the present invention pertains to a compound of Formula (1), Formula (2), or Formula (3), as described herein, which is obtainable by a method of synthesis as described herein, or a method comprising a method of synthesis as described herein.

Another aspect of the present invention pertains to novel intermediates, as described herein, which are suitable for use in the methods of synthesis described herein.

Another aspect of the present invention pertains to the use of such novel intermediates, as described herein, in the methods of synthesis described herein.

Another aspect of the invention pertains to a composition (e.g., a pharmaceutical composition) comprising a compound of Formula (1), Formula (2), or Formula (3), as described herein, and a pharmaceutically acceptable carrier or diluent.

Another aspect of the invention pertains to a method of preparing a composition (e.g., a pharmaceutical composition) comprising the step of mixing a compound of Formula (1), Formula (2), or Formula (3), as described herein, and a pharmaceutically acceptable carrier or diluent.

Another aspect of the present invention pertains to a compound of Formula (1), Formula (2), or Formula (3), as described herein, for use in medicine, for example, for use in treatment or prophylaxis, for example, for use in treatment or prophylaxis of a disorder (e.g., a disease), as described herein.

Another aspect of the present invention pertains to use of a compound of Formula (1), Formula (2), or Formula (3), as described herein, in the manufacture of a medicament, for example, for use in a method of treatment or prophylaxis, for example, for use in a method of treatment or prophylaxis of a disorder (e.g., a disease), as described herein.

Another aspect of the present invention pertains to a method of treatment or prophylaxis, for example, a method of treatment or prophylaxis of a disorder (e.g., a disease), as described herein, comprising administering to a subject in need of treatment a therapeutically-effective amount of a compound of Formula (1), Formula (2), or Formula (3), as described herein, preferably in the form of a pharmaceutical composition.

As will be appreciated by one of skill in the art, features and preferred embodiments of one aspect of the invention will also pertain to other aspects of the invention.

DETAILED DESCRIPTION OF THE INVENTION

Compounds

Figure 1:
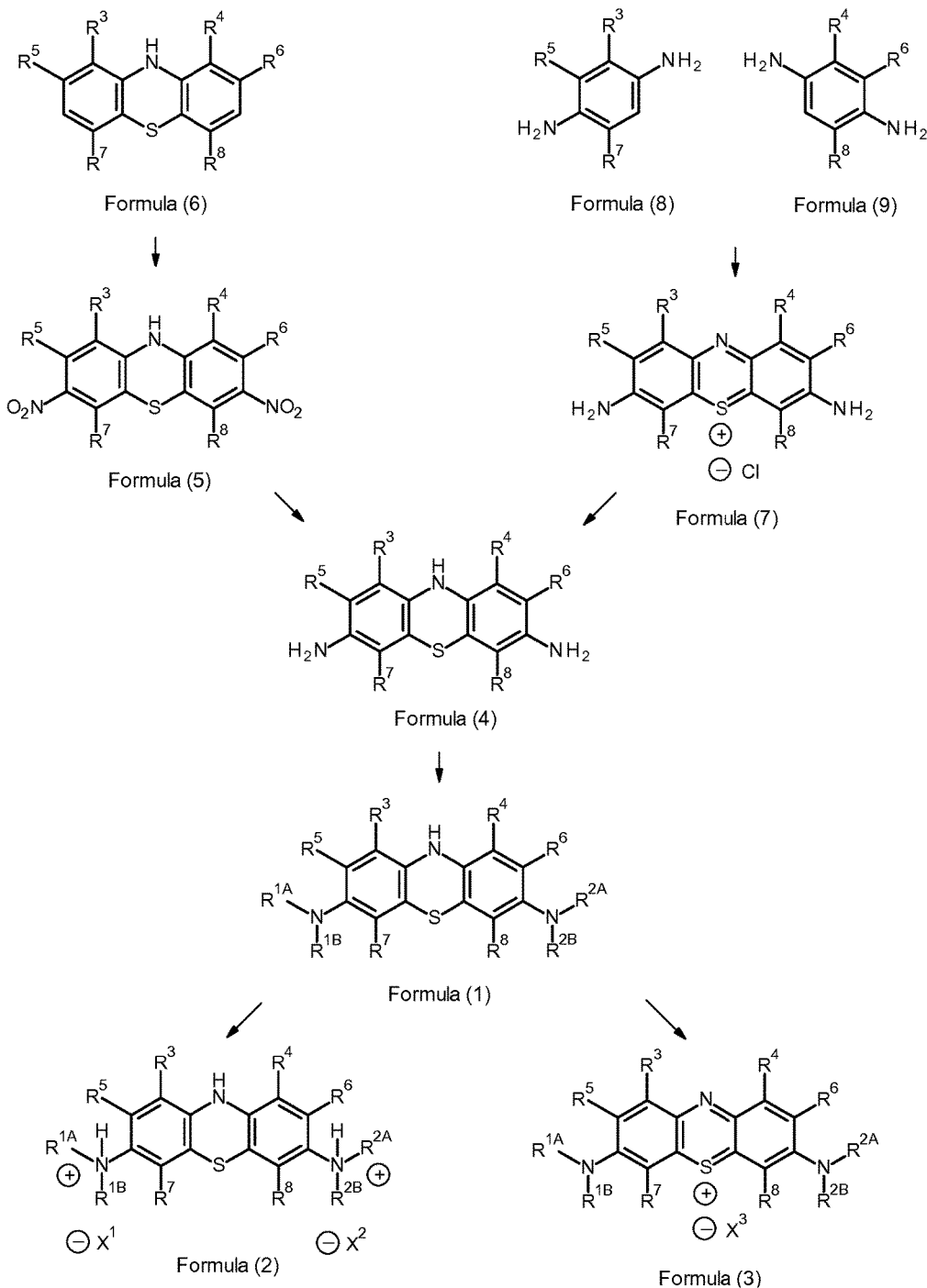
FIG. 1 shows the chemical synthetic routes described herein, in which a compound of Formula (1) is prepared from the corresponding compound of Formula (4); in which a compound of Formula (4) is prepared from the corresponding compound of Formula (5); in which a compound of Formula (5) is prepared from the corresponding compound of Formula (6); in which a compound of Formula (4) is prepared from the corresponding compound of Formula (7); in which a compound of Formula (7) is prepared from the corresponding compounds of Formulae (8) and (9); in which a compound of Formula (2) is prepared from the corresponding compound of Formula (1); and in which a compound of Formula (3) is prepared from the corresponding compound of Formula (1).

The present invention relates generally to methods of chemical synthesis, and more particularly, to methods of chemical synthesis of compounds of Formula (1), Formula (2), and Formula (3). Compounds of Formula (1), Formula (2), and Formula (3) are useful, for example, in the treatment of diseases of protein aggregation, such as Alzheimer's disease.

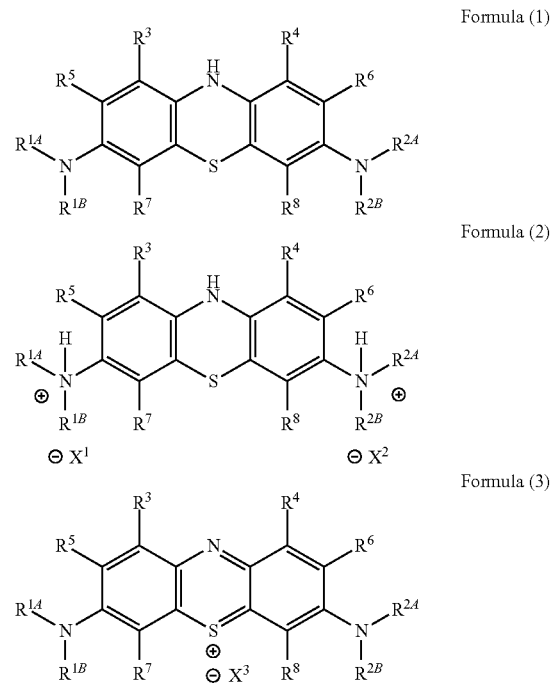

The Groups $R^{1A}$ and $R^{1B}$

In the compounds described herein:

$R^{1A}$ is independently a substituent with one point of attachment, wherein the attachment is via a —CH< group; and $R^{1B}$ is independently H or a substituent with one point of attachment, wherein the attachment is via a —CH< group;

or $R^{1A}$ and $R^{1B}$, taken together, form a substituent with two points of attachment, wherein each of the attachments is via a —CH< group.

For example, when $R^{1A}$ is —$CH_3$, it may be denoted —$CH(H)_2$, where the leading CH forms the point of attachment, —CH<.

Similarly, when $R^{1A}$ is —$CH_2CH_3$, it may be denoted —$CH(CH_3)(H)$, where the leading CH forms the point of attachment, —CH<.

Similarly, when $R^{1A}$ is cyclohexyl, it may be denoted —$CH[-(CH_2)_5-]$, where the leading CH forms the point of attachment, —CH<.

Similarly, when $R^{1A}$ is benzyl (i.e., —$CH_2$-phenyl), it may be denoted —$CH(phenyl)(H)$, where the leading CH forms the point of attachment, —CH<.

Similarly, when $R^{1A}$ and $R^{1B}$, taken together, form butylene (i.e., —$(CH_2)_4$—), it may be denoted —$CH(H)(-CH_2CH_2-)CH(H)$—, where the leading and following CH groups form the points of attachment, —CH< and >CH—.

In one embodiment:
$R^{1A}$ is —$CH(R^{1AX})(R^{1AY})$; and
$R^{1B}$ is independently —H or —$CH(R^{1BX})(R^{1BY})$; or
$R^{1A}$ and $R^{1B}$, taken together, form —$CH_2$—$R^{1AB}$—$CH_2$—;
wherein:
$R^{1AX}$ is independently —H, $C_{1-10}$alkyl, $C_{3-6}$cycloalkyl, or $C_{6-10}$carboaryl; and
$R^{1AY}$ is independently —H, $C_{1-10}$alkyl, $C_{3-6}$cycloalkyl, or $C_{6-10}$carboaryl; or
$R^{1AX}$ and $R^{1AY}$, taken together, form $C_{4-6}$alkylene;
and wherein:
$R^{1BX}$ is independently —H, $C_{1-10}$alkyl, $C_{3-6}$cycloalkyl, or $C_{6-10}$carboaryl; and
$R^{1BY}$ is independently —H, $C_{1-10}$alkyl, $C_{3-6}$cycloalkyl, or $C_{6-10}$carboaryl; or
$R^{1BX}$ and $R^{1BY}$, taken together, form $C_{4-6}$alkylene;
and wherein:
$R^{1AB}$ is $C_{2-4}$alkylene;
wherein:
each $C_{6-10}$ carboaryl is optionally substituted with one or more groups selected from: —$R^{S1}$, —F, —Cl, —Br, —I, —OH, —$OR^{S1}$, —$NH_2$, —$NHR^{S1}$, —$NR^{S1}_2$, pyrrolidino, piperidino, morpholino, —C(=O)OH, and —C(=O)$OR^{S1}$; wherein each —$R^{S1}$ is a $C_{1-4}$alkyl group.

"N-Monosubstituted":
In one embodiment:
$R^{1A}$ is —$CH(R^{1AX})(R^{1AY})$; and
$R^{1B}$ is —H.

"N,N-Disubstituted":
In one embodiment:
$R^{1A}$ is —$CH(R^{1AX})(R^{1AY})$; and
$R^{1B}$ is —$CH(R^{1BX})(R^{1BY})$; or
$R^{1A}$ and $R^{1B}$, taken together, form —$CH_2$—$R^{1AB}$—$CH_2$—.

In one embodiment:
$R^{1A}$ is —$CH(R^{1AX})(R^{1AY})$; and
$R^{1B}$ is —$CH(R^{1BX})(R^{1BY})$).

In one embodiment, $R^{1A}$ and $R^{1B}$ are the same.

For example, when $R^{1A}$ and $R^{1B}$ are both -Me, the group —$NR^{1A}R^{1B}$ (in Formula (1) and Formula (3)) is —$NMe_2$ and the group —$N(H^+)R^{1A}R^{1B}$ (in Formula (2)) is —$N(H^+)Me_2$.

In one embodiment, $R^{1A}$ and $R^{1B}$ are different.

For example, when $R^{1A}$ is -iPr and $R^{1B}$ is —H, the group —$NR^{1A}R^{1B}$ (in Formula (1) and Formula (3)) is —$N(iPr)H$ and the group —$N(H+)R^{1A}R^{1B}$ (in Formula (2)) is —$N(H^+)$(iPr)H.

"N,N-Disubstituted, Ring-Forming":
In one embodiment:
$R^{1A}$ and $R^{1B}$, taken together, form —$CH_2$—$R^{1AB}$—$CH_2$—.

The Groups $R^{2A}$ and $R^{2B}$
In the compounds described herein:
$R^{2A}$ is independently a substituent with one point of attachment, wherein the attachment is via a —CH< group; and
$R^{2B}$ is independently H or a substituent with one point of attachment, wherein the attachment is via a —CH< group;
or
$R^{2A}$ and $R^{2B}$, taken together, form a substituent with two points of attachment,
wherein each of the attachments is via a —CH< group.

In one embodiment:
$R^{2A}$ is —$CH(R^{2AX})(R^{2AY})$; and
$R^{2B}$ is independently —H or —$CH(R^{2BX})(R^{2BY})$; or
$R^{2A}$ and $R^{2B}$, taken together, form —$CH_2$—$R^{2AB}$—$CH_2$—;
wherein:
$R^{2AX}$ is independently —H, $C_{1-10}$alkyl, $C_{3-6}$cycloalkyl, or $C_{6-10}$carboaryl; and
$R^{2AY}$ is independently —H, $C_{1-10}$alkyl, $C_{3-6}$cycloalkyl, or $C_{6-10}$carboaryl; or
$R^{2AX}$ and $R^{2AY}$, taken together, form $C_{4-6}$alkylene;
and wherein:
$R^{2BX}$ is independently —H, $C_{1-10}$alkyl, $C_{3-6}$cycloalkyl, or $C_{6-10}$carboaryl; and
$R^{2BY}$ is independently —H, $C_{1-10}$alkyl, $C_{3-6}$cycloalkyl, or $C_{6-10}$carboaryl; or
$R^{2BX}$ and $R^{2BY}$, taken together, form $C_{4-6}$alkylene;
and wherein:
$R^{2AB}$ is $C_{2-4}$alkylene;
wherein:
each $C_{6-10}$carboaryl is optionally substituted with one or more groups selected from: —$R^{S1}$, —F, —Cl, —Br, —I, —OH, —$OR^{S1}$, —$NH_2$, —$NHR^{S1}$, —$NR^{S1}_2$, pyrrolidino, piperidino, morpholino, —C(=O)OH, and —C(=O)$OR^{S1}$; wherein each —$R^{S1}$ is a $C_{1-4}$alkyl group.

"N-Monosubstituted":
In one embodiment:
$R^{2A}$ is —$CH(R^{2AX})(R^{2AY})$; and
$R^{2B}$ is —H.

"N,N-Disubstituted":
In one embodiment:
$R^{2A}$ is —$CH(R^{2AX})(R^{2AY})$; and
$R^{2B}$ is —$CH(R^{2BX})(R^{2BY})$; or
$R^{2A}$ and $R^{2B}$, taken together, form —$CH_2$—$R^{2AB}$—$CH_2$—.

In one embodiment:
$R^{2A}$ is —$CH(R^{2AX})(R^{2AY})$; and
$R^{2B}$ is —$CH(R^{2BX})(R^{2BY})$.

In one embodiment, $R^{2A}$ and $R^{2B}$ are the same.
In one embodiment, $R^{2A}$ and $R^{2B}$ are different.

"N,N-Disubstituted, Ring-Forming":
In one embodiment:
$R^{2A}$ and $R^{2B}$, taken together, form —$CH_2$—$R^{2AB}$—$CH_2$—.

The Groups —$NR^{1A}R^{1B}$ and —$NR^{2A}R^{2B}$
In one embodiment, —$NR^{1A}R^{1B}$ and —$NR^{2A}R^{2B}$ are the same.

For example, when:
$R^{1AX}$ is —H; $R^{1AY}$ is —H; (i.e., from formaldehyde)
$R^{1BX}$ is —H; $R^{1BY}$ is —H; (i.e., from formaldehyde)
$R^{2AX}$ is —H; $R^{2AY}$ is —H; (i.e., from formaldehyde)
$R^{2BX}$ is —H; $R^{2BY}$ is —H; (i.e., from formaldehyde)

then:
  $R^{1A}$ is —CH($R^{1AX}$)($R^{1AY}$) is —CH$_3$; (i.e., from formaldehyde)
  $R^{1B}$ is —CH($R^{1BX}$)($R^{1BY}$) is —CH$_3$; (i.e., from formaldehyde)
  $R^{2A}$ is —CH($R^{2AX}$)($R^{2AY}$) is —CH$_3$; (i.e., from formaldehyde)
  $R^{2B}$ is —CH($R^{2BX}$)($R^{2BY}$) is —CH$_3$; (i.e., from formaldehyde)
and then:
  —NR$^{1A}$R$^{1B}$ is —N(CH$_3$)$_2$; and
  —NR$^{2A}$R$^{2B}$ is —N(CH$_3$)$_2$.
For example, when:
  $R^{1AX}$ is —CH$_3$; $R^{1AY}$ is —CH$_3$; (i.e., from acetone)
  $R^{1B}$ is —H;
  $R^{2AX}$ is —CH$_3$; $R^{2AY}$ is —CH$_3$; (i.e., from acetone)
  $R^{2B}$ is —H;
then:
  $R^{1A}$ is —CH($R^{1AX}$)($R^{1AY}$) is —CH(CH$_3$)$_2$; (i.e., from acetone)
  $R^{1B}$ is —H;
  $R^{2A}$ is —CH($R^{2AX}$)($R^{2AY}$) is —CH(CH$_3$)$_2$; (i.e., from acetone)
  $R^{2B}$ is —H;
and then:
  —NR$^{1A}$R$^{1B}$ is —N(iPr)H; and
  —NR$^{2A}$R$^{2B}$ is —N(iPr)H.
In one embodiment, —NR$^{1A}$R$^{1B}$ and —NR$^{2A}$R$^{2B}$ are different.

The Groups $R^{1AX}$ and $R^{1AY}$
  In one embodiment:
    $R^{1AX}$ is independently —H, C$_{1-10}$alkyl, C$_{3-6}$cycloalkyl, or C$_{6-10}$carboaryl; and
    $R^{1AY}$ is independently —H, C$_{1-10}$alkyl, C$_{3-6}$cycloalkyl, or C$_{6-10}$carboaryl; or
    $R^{1AX}$ and $R^{1AY}$, taken together, form C$_{4-6}$alkylene;
  wherein:
    each C$_{6-10}$carboaryl is optionally substituted with one or more groups selected from: —R$^{S1}$, —F, —Cl, —Br, —I, —OH, —OR$^{S1}$, —NH$_2$, —NHR$^{S1}$, —NR$^{S1}$$_2$, pyrrolidino, piperidino, morpholino, —C(=O)OH, and —C(=O)OR$^{S1}$; wherein each —R$^{S1}$ is a C$_{1-4}$alkyl group.
  In one embodiment:
    $R^{1AX}$ is independently —H, C$_{1-6}$alkyl, C$_{3-6}$cycloalkyl, or C$_{6-10}$carboaryl; and
    $R^{1AY}$ is independently —H, C$_{1-6}$alkyl, C$_{3-6}$cycloalkyl, or C$_{6-10}$carboaryl; or
    $R^{1AX}$ and $R^{1AY}$, taken together, form C$_{4-6}$alkylene.
  In one embodiment:
    $R^{1AX}$ is independently —H, C$_{1-4}$alkyl, C$_{5-6}$cycloalkyl, or phenyl; and
    $R^{1AY}$ is independently —H, C$_{1-4}$alkyl, C$_{5-6}$cycloalkyl, or phenyl; or
    $R^{1AX}$ and $R^{1AY}$, taken together, form C$_{4-6}$alkylene.
  In one embodiment:
    $R^{1AX}$ is independently —H, C$_{1-4}$alkyl or phenyl; and
    $R^{1AY}$ is independently —H, C$_{1-4}$alkyl or phenyl; or
    $R^{1AX}$ and $R^{1AY}$, taken together, form C$_{4-6}$alkylene.
  In one embodiment:
    $R^{1AX}$ is independently —H or C$_{1-4}$alkyl; and
    $R^{1AY}$ is independently —H or C$_{1-4}$alkyl; or
    $R^{1AX}$ and $R^{1AY}$, taken together, form C$_{4-6}$alkylene.
  In one embodiment:
    $R^{1AX}$ is independently —H or C$_{1-4}$alkyl; and
    $R^{1AY}$ is independently —H or C$_{1-4}$alkyl.

"CH— Unsubstituted" (i.e., from formaldehyde):
  In one embodiment:
    $R^{1AX}$ is —H.
    $R^{1AY}$ is —H.
  In this embodiment, $R^{1AX}$ is —H and $R^{1AY}$ is —H, and so $R^{1A}$ is —CH($R^{1AX}$)($R^{1AY}$) is —CH$_3$ (from formaldehyde, HC(=O)H).

"CH-Monosubstituted" (i.e., from other aldehydes):
  In one embodiment:
    $R^{1AX}$ is independently C$_{1-10}$alkyl, C$_{3-6}$cycloalkyl, or C$_{6-10}$carboaryl; and
    $R^{1AY}$ is —H;
  wherein:
    C$_{6-10}$carboaryl is optionally substituted with one or more groups selected from: —R$^{S1}$, —F, —Cl, —Br, —I, —OH, —OR$^{S1}$, —NH$_2$, —NHR$^{S1}$, —NR$^{S1}$$_2$, pyrrolidino, piperidino, morpholino, —C(=O)OH, and —C(=O)OR$^{S1}$; wherein each —R$^{S1}$ is a C$_{1-4}$alkyl group.
  In one embodiment:
    $R^{1AX}$ is independently C$_{1-6}$alkyl, C$_{3-6}$cycloalkyl, or C$_{6-10}$carboaryl; and
    $R^{1AY}$ is —H.
  In one embodiment:
    $R^{1AX}$ is independently C$_{1-4}$alkyl, C$_{5-6}$cycloalkyl, or phenyl; and
    $R^{1AY}$ is —H.
  In one embodiment:
    $R^{1AX}$ is independently C$_{1-4}$alkyl or phenyl; and
    $R^{1AY}$ is —H.
  In one embodiment:
    $R^{1AX}$ is C$_{1-4}$alkyl; and
    $R^{1AY}$ is —H.
  For example, in one embodiment, $R^{1AX}$ is -Me and $R^{1AY}$ is —H, and so $R^{1A}$ is —CH($R^{1AX}$)($R^{1AY}$) is —CH$_2$CH$_3$ (from acetaldehyde, CH$_3$C(=O)H).

"CH-Disubstituted" (i.e., from ketones):
  In one embodiment:
    $R^{1AX}$ is independently C$_{1-10}$alkyl, C$_{3-6}$cycloalkyl, or C$_{6-10}$carboaryl; and
    $R^{1AY}$ is independently C$_{1-10}$alkyl, C$_{3-6}$cycloalkyl, or C$_{6-10}$carboaryl; or
    $R^{1AX}$ and $R^{1AY}$, taken together, form C$_{4-6}$alkylene;
  wherein:
    each C$_{6-10}$carboaryl is optionally substituted with one or more groups selected from: —R$^{S1}$, —F, —Cl, —Br, —I, —OH, —OR$^{S1}$, —NH$_2$, —NHR$^{S1}$, —NR$^{S1}$$_2$, pyrrolidino, piperidino, morpholino, —C(=O)OH, and —C(=O)OR$^{S1}$; wherein each —R$^{S1}$ is a C$_{1-4}$alkyl group.
  In one embodiment:
    $R^{1AX}$ is independently C$_{1-6}$alkyl, C$_{3-6}$cycloalkyl, or C$_{6-10}$carboaryl; and
    $R^{1AY}$ is independently C$_{1-6}$alkyl, C$_{3-6}$cycloalkyl, or C$_{6-10}$carboaryl; or
    $R^{1AX}$ and $R^{1AY}$, taken together, form C$_{4-6}$alkylene.
  In one embodiment:
    $R^{1AX}$ is independently C$_{1-4}$alkyl, C$_{5-6}$cycloalkyl, or phenyl; and
    $R^{1AY}$ is independently C$_{1-4}$alkyl, C$_{5-6}$cycloalkyl, or phenyl; or
    $R^{1AX}$ and $R^{1AY}$, taken together, form C$_{4-6}$alkylene.
  In one embodiment:
    $R^{1AX}$ is independently C$_{1-4}$alkyl or phenyl; and
    $R^{1AY}$ is independently C$_{1-4}$alkyl or phenyl; or
    $R^{1AX}$ and $R^{1AY}$, taken together, form C$_{4-6}$alkylene.

In one embodiment:
$R^{1AX}$ is $C_{1-4}$alkyl; and
$R^{1AY}$ is $C_{1-4}$alkyl; or
$R^{1AX}$ and $R^{1AY}$, taken together, form $C_{4-6}$alkylene.

In one embodiment:
$R^{1AX}$ is $C_{1-4}$alkyl; and
$R^{1AY}$ is $C_{1-4}$alkyl.

For example, in one embodiment, $R^{1AX}$ is -Me and $R^{1AY}$ is -Me, and so $R^{1A}$ is —CH($R^{1AX}$)($R^{1AY}$) is —CH(CH$_3$)$_2$ (from acetone, CH$_3$C(=O)CH$_3$).

"CH-Disubstituted, Ring-Forming" (i.e., from cyclic ketones):

In one embodiment:
$R^{1AX}$ and $R^{1AY}$, taken together, form $C_{4-6}$alkylene.

For example, in one embodiment, $R^{1AX}$ and $R^{1AY}$, taken together, form —(CH$_2$)$_5$—, and so $R^{1A}$ is —CH($R^{1AX}$)($R^{1AY}$) is —CH[—(CH$_2$)$_5$—], that is, cyclohexyl (from cyclohexanone).

The Groups $R^{1BX}$ and $R^{1BY}$

In one embodiment:
$R^{1BX}$, if present, is independently —H, $C_{1-10}$alkyl, $C_{3-6}$cycloalkyl, or $C_{6-10}$carboaryl; and
$R^{1BY}$, if present, is independently —H, $C_{1-10}$alkyl, $C_{3-6}$cycloalkyl, or $C_{6-10}$carboaryl; or
$R^{1BX}$ and $R^{1BY}$, if present, taken together, form $C_{4-6}$alkylene;

wherein:
each $C_{6-10}$carboaryl is optionally substituted with one or more groups selected from: —$R^{S1}$, —F, —Cl, —Br, —I, —OH, —O$R^{S1}$, —NH$_2$, —NH$R^{S1}$, —N$R^{12}$, pyrrolidino, piperidino, morpholino, —C(=O)OH, and —C(=O)O$R^{S1}$; wherein each —$R^{S1}$ is a $C_{1-4}$alkyl group.

In one embodiment:
$R^{1BX}$, if present, is independently —H, $C_{1-6}$alkyl, $C_{3-6}$cycloalkyl, or $C_{6-10}$carboaryl; and
$R^{1BY}$, if present, is independently —H, $C_{1-6}$alkyl, $C_{3-6}$cycloalkyl, or $C_{6-10}$carboaryl; or
$R^{1BX}$ and $R^{1BY}$, if present, taken together, form $C_{4-6}$alkylene;

In one embodiment:
$R^{1BX}$, if present, is independently —H, $C_{1-4}$alkyl, $C_{5-6}$cycloalkyl, or phenyl; and
$R^{1BY}$, if present, is independently —H, $C_{1-4}$alkyl, $C_{5-6}$cycloalkyl, or phenyl; or
$R^{1BX}$ and $R^{1BY}$, if present, taken together, form $C_{4-6}$alkylene.

In one embodiment:
$R^{1BX}$, if present, is independently —H, $C_{1-4}$alkyl, or phenyl; and
$R^{1BY}$, if present, is independently —H, $C_{1-4}$alkyl, or phenyl; or
$R^{1BX}$ and $R^{1BY}$, if present, taken together, form $C_{4-6}$alkylene.

In one embodiment:
$R^{1BX}$, if present, is independently —H or $C_{1-4}$alkyl; and
$R^{1BY}$, if present, is independently —H or $C_{1-4}$alkyl; or
$R^{1BX}$ and $R^{1BY}$, if present, taken together, form $C_{4-6}$alkylene.

In one embodiment:
$R^{1BX}$, if present, is independently —H or $C_{1-4}$alkyl; and
$R^{1BY}$, if present, is independently —H or $C_{1-4}$alkyl.

"CH-Unsubstituted" (i.e., from formaldehyde):
In one embodiment:
$R^{1BX}$ is —H.
$R^{1BY}$ is —H.

In this embodiment, $R^{1BX}$ is —H and $R^{1BY}$ is —H, and so $R^{1B}$ is —CH($R^{1BX}$)($R^{1BY}$) is —CH$_3$ (from formaldehyde, HC(=O)H).

"CH-Monosubstituted" (i.e., from other aldehydes):
In one embodiment:
$R^{1BX}$, if present, is independently $C_{1-10}$alkyl, $C_{3-6}$cycloalkyl, or $C_{6-10}$carboaryl; and
$R^{1BY}$, if present, is —H;
wherein:
$C_{6-10}$carboaryl is optionally substituted with one or more groups selected from: —$R^{S1}$, —F, —Cl, —Br, —I, —OH, —O$R^{S1}$, —NH$_2$, —NH$R^{S1}$, —N$R^{S1}_2$, pyrrolidino, piperidino, morpholino, —C(=O)OH, and —C(=O)O$R^{S1}$; wherein each —$R^{S1}$ is a $C_{1-4}$alkyl group.

In one embodiment:
$R^{1BX}$, if present, is independently $C_{1-6}$alkyl, $C_{3-6}$cycloalkyl, or $C_{6-10}$carboaryl; and
$R^{1BY}$, if present, is —H;

In one embodiment:
$R^{1BX}$, if present, is independently $C_{1-4}$alkyl, $C_{5-6}$cycloalkyl, or phenyl; and
$R^{1BY}$, if present, is —H.

In one embodiment:
$R^{1BX}$, if present, is independently $C_{1-4}$alkyl or phenyl; and
$R^{1BY}$, if present, is —H.

In one embodiment:
$R^{1BX}$, if present, is $C_{1-4}$alkyl; and
$R^{1BY}$, if present, is —H.

For example, in one embodiment, $R^{1BX}$ is -Me and $R^{1BY}$ is —H, and so $R^{1B}$ is —CH($R^{1BX}$)($R^{1BY}$) is —CH$_2$CH$_3$ (from acetaldehyde, CH$_3$C(=O)H).

"CH-Disubstituted" (i.e., from ketones):
In one embodiment:
$R^{1BX}$, if present, is independently $C_{1-10}$alkyl, $C_{3-6}$cycloalkyl, or $C_{6-10}$carboaryl; and
$R^{1BY}$, if present, is independently $C_{1-10}$alkyl, $C_{3-6}$cycloalkyl, or $C_{6-10}$carboaryl; or
$R^{1BX}$ and $R^{1BY}$, if present, taken together, form $C_{4-6}$alkylene;

wherein:
each $C_{6-10}$carboaryl is optionally substituted with one or more groups selected from: —$R^{S1}$, —F, —Cl, —Br, —I, —OH, —O$R^{S1}$, —NH$_2$, —NH$R^{S1}$, —N$R^{S1}_2$, pyrrolidino, piperidino, morpholino, —C(=O)OH, and —C(=O)O$R^{S1}$; wherein each —$R^{S1}$ is a $C_{1-4}$alkyl group.

In one embodiment:
$R^{1BX}$, if present, is independently $C_{1-6}$alkyl, $C_{3-6}$cycloalkyl, or $C_{6-10}$carboaryl; and
$R^{1BY}$, if present, is independently $C_{1-6}$alkyl, $C_{3-6}$cycloalkyl, or $C_{6-10}$carboaryl; or
$R^{1BX}$ and $R^{1BY}$, if present, taken together, form $C_{4-6}$alkylene;

In one embodiment:
$R^{1BX}$, if present, is independently $C_{1-4}$alkyl, $C_{5-6}$cycloalkyl, or phenyl; and
$R^{1BY}$, if present, is independently $C_{1-4}$alkyl, $C_{5-6}$cycloalkyl, or phenyl; or
$R^{1BX}$ and $R^{1BY}$, if present, taken together, form $C_{4-6}$alkylene.

In one embodiment:
$R^{1BX}$, if present, is independently $C_{1-4}$alkyl or phenyl; and
$R^{1BY}$, if present, is independently $C_{1-4}$alkyl or phenyl; or
$R^{1BX}$ and $R^{1BY}$, if present, taken together, form $C_{4-6}$alkylene.

In one embodiment:
$R^{1BX}$, if present, is $C_{1-4}$alkyl; and
$R^{1BY}$, if present, is $C_{1-4}$alkyl; or
$R^{1BX}$ and $R^{1BY}$, if present, taken together, form $C_{4-6}$alkylene.

In one embodiment:
$R^{1BX}$, if present, is $C_{1-4}$alkyl; and
$R^{1BY}$, if present, is $C_{1-4}$alkyl.

For example, in one embodiment, $R^{1BX}$ is -Me and $R^{1BY}$ is -Me, and so $R^{1B}$ is —CH($R^{1BX}$)($R^{1BY}$) is —CH(CH$_3$)$_2$ (from acetone, CH$_3$C(=O)CH$_3$).

"CH-Disubstituted, Ring-Forming" (i.e., from cyclic ketones):
In one embodiment:
$R^{1BX}$ and $R^{1BY}$, taken together, form $C_{4-6}$alkylene.

For example, in one embodiment, $R^{1BX}$ and $R^{1BY}$, taken together, form —(CH$_2$)$_5$—, and so $R^{1B}$ is —CH($R^{1BX}$)($R^{1BY}$) is —CH[—(CH$_2$)$_5$—], that is, cyclohexyl (from cyclohexanone).

The Group $R^{1AB}$
In one embodiment, $R^{1AB}$ is $C_{2-4}$alkylene.
In one embodiment, $R^{1AB}$ is $C_{3-4}$alkylene.
In one embodiment, $R^{1AB}$ is $C_2$alkylene.
In one embodiment, $R^{1AB}$ is $C_3$alkylene.
In one embodiment, $R^{1AB}$ is $C_4$alkylene.
In one embodiment, $R^{1AB}$ is linear $C_{2-4}$alkylene.
In one embodiment, $R^{1AB}$ is linear $C_{3-4}$alkylene.
In one embodiment, $R^{1AB}$ is linear $C_2$alkylene (i.e. —(CH$_2$)$_2$—).
In one embodiment, $R^{1AB}$ is linear $C_3$alkylene (i.e. —(CH$_2$)$_3$—).
In one embodiment, $R^{1AB}$ is linear $C_4$alkylene (i.e. —(CH$_2$)$_4$—).

For example, in one embodiment, $R^{1A}$ and $R^{1B}$, taken together, form —CH$_2$—$R^{1AB}$—CH$_2$—; and $R^{1AB}$ is —(CH$_2$)$_3$—; and so $R^{1A}$ and $R^{1B}$, taken together, form —(CH$_2$)$_5$—; and so the group —NR$^{1A}$R$^{1B}$ is piperidino (from the di-aldehyde, glutaraldehyde).

The Groups $R^{2AX}$ and $R^{2AY}$
In one embodiment:
$R^{2AX}$ is independently —H, $C_{1-10}$alkyl, $C_{3-6}$cycloalkyl, or $C_{6-10}$carboaryl; and
$R^{2AY}$ is independently —H, $C_{1-10}$alkyl, $C_{3-6}$cycloalkyl, or $C_{6-10}$carboaryl; or
$R^{2AX}$ and $R^{2AY}$, taken together, form $C_{4-6}$alkylene;
wherein:
each $C_{6-10}$carboaryl is optionally substituted with one or more groups selected from: —R$^{S2}$, —F, —Cl, —Br, —I, —OH, —OR$^{S2}$, —NH$_2$, —NHR$^{S2}$, —NR$^{S2}{}_2$, pyrrolidino, piperidino, morpholino, —C(=O)OH, and —C(=O)OR$^{S2}$; wherein each —R$^{S2}$ is a $C_{1-4}$alkyl group.

In one embodiment:
$R^{2AX}$ is independently —H, $C_{1-6}$alkyl, $C_{3-6}$cycloalkyl, or $C_{6-10}$carboaryl; and
$R^{2AY}$ is independently —H, $C_{1-6}$alkyl, $C_{3-6}$cycloalkyl, or $C_{6-10}$carboaryl; or
$R^{2AX}$ and $R^{2AY}$, taken together, form $C_{4-6}$alkylene.

In one embodiment:
$R^{2AX}$ is independently —H, $C_{1-4}$alkyl, $C_{5-6}$cycloalkyl, or phenyl; and
$R^{2AY}$ is independently —H, $C_{1-4}$alkyl, $C_{5-6}$cycloalkyl, or phenyl; or
$R^{2AX}$ and $R^{2AY}$, taken together, form $C_{4-6}$alkylene.

In one embodiment:
$R^{2AX}$ is independently —H, $C_{1-4}$alkyl or phenyl; and
$R^{2AY}$ is independently —H, $C_{1-4}$alkyl or phenyl; or
$R^{2AX}$ and $R^{2AY}$, taken together, form $C_{4-6}$alkylene.

In one embodiment:
$R^{2AX}$ is independently —H or $C_{1-4}$alkyl; and
$R^{2AY}$ is independently —H or $C_{1-4}$alkyl; or
$R^{2AX}$ and $R^{2AY}$, taken together, form $C_{4-6}$alkylene.

In one embodiment:
$R^{2AX}$ is independently —H or $C_{1-4}$alkyl; and
$R^{2AY}$ is independently —H or $C_{1-4}$alkyl.

"CH-Unsubstituted" (i.e., from formaldehyde):
In one embodiment:
$R^{2AX}$ is —H.
$R^{2AY}$ is —H.

In this embodiment, $R^{2AX}$ is —H and $R^{2AY}$ is —H, and so $R^{2A}$ is —CH($R^{2AX}$)($R^{2AY}$) is —CH$_3$ (from formaldehyde, HC(=O)H).

"CH-Monosubstituted" (i.e., from other aldehydes):
In one embodiment:
$R^{2AX}$ is independently $C_{1-10}$alkyl, $C_{3-6}$cycloalkyl, or $C_{6-10}$carboaryl; and
$R^{2AY}$ is —H;
wherein:
$C_{6-10}$carboaryl is optionally substituted with one or more groups selected from: —R$^S$, —F, —Cl, —Br, —I, —OH, —OR$^{S2}$, —NH$_2$, —NHR$^{S2}$, —NR$^{S2}{}_2$, pyrrolidino, piperidino, morpholino, —C(=O)OH, and —C(=O)OR$^{S2}$; wherein each —R$^{S2}$ is a $C_{1-4}$alkyl group.

In one embodiment:
$R^{2AX}$ is independently $C_{1-6}$alkyl, $C_{3-6}$cycloalkyl, or $C_{6-10}$carboaryl; and
$R^{2AY}$ is —H.

In one embodiment:
$R^{2AX}$ is independently $C_{1-4}$alkyl, $C_{5-6}$cycloalkyl, or phenyl; and
$R^{2AY}$ is —H.

In one embodiment:
$R^{2AX}$ is independently $C_{1-4}$alkyl or phenyl; and
$R^{2AY}$ is —H.

In one embodiment:
$R^{2AX}$ is $C_{1-4}$alkyl; and
$R^{2AY}$ is —H.

For example, in one embodiment, $R^{2AX}$ is -Me and $R^{2AY}$ is —H, and so $R^{2A}$ is —CH($R^{2AX}$)($R^{2AY}$) is —CH$_2$CH$_3$ (from acetaldehyde, CH$_3$C(=O)H).

"CH-Disubstituted" (i.e., from ketones):
In one embodiment:
$R^{2AX}$ is independently $C_{1-10}$alkyl, $C_{3-6}$cycloalkyl, or $C_{6-10}$carboaryl; and
$R^{2AY}$ is independently $C_{1-10}$alkyl, $C_{3-6}$cycloalkyl, or $C_{6-10}$carboaryl; or
$R^{2AX}$ and $R^{2AY}$, taken together, form $C_{4-6}$alkylene;
wherein:
each $C_{6-10}$carboaryl is optionally substituted with one or more groups selected from: —R$^{S2}$, —F, —Cl, —Br, —I, —OH, —OR$^{S2}$, —NH$_2$, —NHR$^{S2}$, —NR$^{S2}{}_2$, pyrrolidino, piperidino, morpholino, —C(=O)OH, and —C(=O)OR$^{S2}$; wherein each —R$^{S2}$ is a $C_{1-4}$alkyl group.

In one embodiment:
$R^{2AX}$ is independently $C_{1-6}$alkyl, $C_{3-6}$cycloalkyl, or $C_{6-10}$carboaryl; and
$R^{2AY}$ is independently $C_{1-6}$alkyl, $C_{3-6}$cycloalkyl, or $C_{6-10}$carboaryl; or
$R^{2AX}$ and $R^{2AY}$, taken together, form $C_{4-6}$alkylene.

In one embodiment:
$R^{2AX}$ is independently $C_{1-4}$alkyl, $C_{5-6}$cycloalkyl, or phenyl; and
$R^{2AY}$ is independently $C_{1-4}$alkyl, $C_{5-6}$cycloalkyl, or phenyl; or
$R^{2AX}$ and $R^{2AY}$, taken together, form $C_{4-6}$alkylene.

In one embodiment:
$R^{2AX}$ is independently $C_{1-4}$alkyl or phenyl; and
$R^{2AY}$ is independently $C_{1-4}$alkyl or phenyl; or
$R^{2AX}$ and $R^{2AY}$, taken together, form $C_{4-6}$alkylene.

In one embodiment:
$R^{2AX}$ is $C_{1-4}$alkyl; and
$R^{2AY}$ is $C_{1-4}$alkyl; or
$R^{2AX}$ and $R^{2AY}$, taken together, form $C_{4-6}$alkylene.

In one embodiment:
$R^{2AX}$ is $C_{1-4}$alkyl; and
$R^{2AY}$ is $C_{1-4}$alkyl.

For example, in one embodiment, $R^{2AX}$ is -Me and $R^{2AY}$ is -Me, and so $R^{2A}$ is —CH($R^{2AX}$)($R^{2AY}$) is —CH(CH$_3$)$_2$ (from acetone, CH$_3$C(=O)CH$_3$).

"CH-Disubstituted, Ring-Forming" (i.e., from cyclic ketones):
In one embodiment:
$R^{2AX}$ and $R^{2AY}$, taken together, form $C_{4-6}$alkylene.

For example, in one embodiment, $R^{2AX}$ and $R^{2AY}$, taken together, form —(CH$_2$)$_5$—, and so $R^{2A}$ is —CH($R^{2AX}$)($R^{2AY}$) is —CH[—(CH$_2$)$_5$—], that is, cyclohexyl (from cyclohexanone).

The Groups $R^{2BX}$ and $R^{2BY}$
In one embodiment:
$R^{2BX}$, if present, is independently —H, $C_{1-10}$alkyl, $C_{3-6}$cycloalkyl, or $C_{6-10}$carboaryl; and
$R^{2BY}$, if present, is independently —H, $C_{1-10}$alkyl, $C_{3-6}$cycloalkyl, or $C_{6-10}$carboaryl; or
$R^{2BX}$ and $R^{2BY}$, if present, taken together, form $C_{4-6}$alkylene;
wherein:
  each $C_{6-10}$carboaryl is optionally substituted with one or more groups selected from: —$R^{S2}$, —F, —Cl, —Br, —I, —OH, —OR$^{S2}$, —NH$_2$, —NHR$^{S2}$, —NR$^{S2}$$_2$, pyrrolidino, piperidino, morpholino, —C(=O)OH, and —C(=O)OR$^{S2}$; wherein each —$R^2$ is a $C_{1-4}$alkyl group.

In one embodiment:
$R^{2BX}$, if present, is independently —H, $C_{1-6}$alkyl, $C_{3-6}$cycloalkyl, or $C_{6-10}$carboaryl; and
$R^{2BY}$, if present, is independently —H, $C_{1-6}$alkyl, $C_{3-6}$cycloalkyl, or $C_{6-10}$carboaryl; or
$R^{2BX}$ and $R^{2BY}$, if present, taken together, form $C_{4-6}$alkylene;

In one embodiment:
$R^{2BX}$, if present, is independently —H, $C_{1-4}$alkyl, $C_{5-6}$cycloalkyl, or phenyl; and
$R^{2BY}$, if present, is independently —H, $C_{1-4}$alkyl, $C_{5-6}$cycloalkyl, or phenyl; or
$R^{2BX}$ and $R^{2BY}$, if present, taken together, form $C_{4-6}$alkylene.

In one embodiment:
$R^{2BX}$, if present, is independently —H, $C_{1-4}$alkyl, or phenyl; and
$R^{2BY}$, if present, is independently —H, $C_{1-4}$alkyl, or phenyl; or
$R^{2BX}$ and $R^{2BY}$, if present, taken together, form $C_{4-6}$alkylene.

In one embodiment:
$R^{2BX}$, if present, is independently —H or $C_{1-4}$alkyl; and
$R^{2BY}$, if present, is independently —H or $C_{1-4}$alkyl; or $R^{2BX}$ and $R^{2BY}$, if present, taken together, form $C_{4-6}$alkylene.

In one embodiment:
$R^{2BX}$, if present, is independently —H or $C_{1-4}$alkyl; and
$R^{2BY}$, if present, is independently —H or $C_{1-4}$alkyl.

"CH-Unsubstituted" (i.e., from formaldehyde):
In one embodiment:
$R^{2BX}$ is —H.
$R^{2BY}$ is —H.

In this embodiment, $R^{2BX}$ is —H and $R^{2BY}$ is —H, and so $R^{2B}$ is —CH($R^{2BX}$)($R^{2BY}$) is —CH$_3$ (from formaldehyde, HC(=O)H).

"CH-Monosubstituted" (i.e., from other aldehydes):
In one embodiment:
$R^{2BX}$, if present, is independently $C_{1-10}$alkyl, $C_{3-6}$cycloalkyl, or $C_{6-10}$carboaryl; and
$R^{2BY}$, if present, is —H;
wherein:
  $C_{6-10}$carboaryl is optionally substituted with one or more groups selected from: —$R^S$, —F, —Cl, —Br, —I, —OH, —OR$^{S2}$, —NH$_2$, —NHR$^{S2}$, —NR$^{S2}$$_2$, pyrrolidino, piperidino, morpholino, —C(=O)OH, and —C(=O)OR$^{S2}$; wherein each —$R^{S2}$ is a $C_{1-4}$alkyl group.

In one embodiment:
$R^{2BX}$, if present, is independently $C_{1-6}$alkyl, $C_{3-6}$cycloalkyl, or $C_{6-10}$carboaryl; and
$R^{2BY}$, if present, is —H;

In one embodiment:
$R^{2BX}$, if present, is independently $C_{1-4}$alkyl, $C_{5-6}$cycloalkyl, or phenyl; and
$R^{2BY}$, if present, is —H.

In one embodiment:
$R^{2BX}$, if present, is independently $C_{1-4}$alkyl or phenyl; and
$R^{2BY}$, if present, is —H.

In one embodiment:
$R^{2BX}$, if present, is $C_{1-4}$alkyl; and
$R^{2BY}$, if present, is —H.

For example, in one embodiment, $R^{2BX}$ is -Me and $R^{2BY}$ is —H, and so $R^{2B}$ is —CH($R^{2BX}$)($R^{2BY}$) is —CH$_2$CH$_3$ (from acetaldehyde, CH$_3$C(=O)H).

"CH-Disubstituted" (i.e., from ketones):
In one embodiment:
$R^{2BX}$, if present, is independently $C_{1-10}$alkyl, $C_{3-6}$cycloalkyl, or $C_{6-10}$carboaryl; and
$R^{2BY}$, if present, is independently $C_{1-10}$alkyl, $C_{3-6}$cycloalkyl, or $C_{6-10}$carboaryl; or
$R^{2BX}$ and $R^{2BY}$, if present, taken together, form $C_{4-6}$alkylene;
wherein:
  each $C_{6-10}$carboaryl is optionally substituted with one or more groups selected from: —$R^{S2}$, —F, —Cl, —Br, —I, —OH, —OR$^{S2}$, —NH$_2$, —NHR$^{S2}$, —NR$^{S2}$$_2$, pyrrolidino, piperidino, morpholino, —C(=O)OH, and —C(=O)OR$^{S2}$; wherein each —$R^{S2}$ is a $C_{1-4}$alkyl group.

In one embodiment:
$R^{2BX}$, if present, is independently $C_{1-6}$alkyl, $C_{3-6}$cycloalkyl, or $C_{6-10}$carboaryl; and
$R^{2BY}$, if present, is independently $C_{1-6}$alkyl, $C_{3-6}$cycloalkyl, or $C_{6-10}$carboaryl; or
$R^{2BX}$ and $R^{2BY}$, if present, taken together, form $C_{4-6}$alkylene;

In one embodiment:
$R^{2BX}$, if present, is independently $C_{1-4}$alkyl, $C_{5-6}$cycloalkyl, or phenyl; and $R^{2BY}$, if present, is independently $C_{1-4}$alkyl, $C_{5-6}$cycloalkyl, or phenyl; or $R^{2BX}$ and $R^{2BY}$, if present, taken together, form $C_{4-6}$alkylene.

In one embodiment:

$R^{2BX}$, if present, is independently $C_{1-4}$alkyl or phenyl; and $R^{2BY}$, if present, is independently $C_{1-4}$alkyl or phenyl; or $R^{2BX}$ and $R^{2BY}$, if present, taken together, form $C_{4-6}$alkylene.

In one embodiment:

$R^{2BX}$, if present, is $C_{1-4}$alkyl; and $R^{2BY}$, if present, is $C_{1-4}$alkyl; or $R^{2BX}$ and $R^{2BY}$, if present, taken together, form $C_{4-6}$alkylene.

In one embodiment:

$R^{2BX}$, if present, is $C_{1-4}$alkyl; and $R^{2BY}$, if present, is $C_{1-4}$alkyl.

For example, in one embodiment, $R^{2BX}$ is -Me and $R^{2BY}$ is -Me, and so $R^{2B}$ is —CH($R^{2BX}$)($R^{2BY}$) is —CH($CH_3$)$_2$ (from acetone, $CH_3C(=O)CH_3$).

"CH-Disubstituted, Ring-Forming" (i.e., from cyclic ketones):

In one embodiment:

$R^{2BX}$ and $R^{2BY}$, taken together, form $C_{4-6}$alkylene.

For example, in one embodiment, $R^{2BX}$ and $R^{2BY}$, taken together, form —($CH_2$)$_5$—, and so $R^{2B}$ is —CH($R^{2BX}$)($R^{2BY}$) is —CH[—($CH_2$)$_5$—], that is, cyclohexyl (from cyclohexanone).

The Group $R^{2AB}$

In one embodiment, $R^{2AB}$ is $C_{2-4}$alkylene.

In one embodiment, $R^{2AB}$ is $C_{3-4}$alkylene.

In one embodiment, $R^{2AB}$ is $C_2$alkylene.

In one embodiment, $R^{2AB}$ is $C_3$alkylene.

In one embodiment, $R^{2AB}$ is $C_4$alkylene.

In one embodiment, $R^{2AB}$ is linear $C_{2-4}$alkylene.

In one embodiment, $R^{2AB}$ is linear $C_{3-4}$alkylene.

In one embodiment, $R^{2AB}$ is linear $C_2$alkylene (i.e. —($CH_2$)$_2$—).

In one embodiment, $R^{2AB}$ is linear $C_3$alkylene (i.e. —($CH_2$)$_3$—).

In one embodiment, $R^{2AB}$ is linear $C_4$alkylene (i.e. —($CH_2$)$_4$—).

For example, in one embodiment, $R^{2A}$ and $R^{2B}$, taken together, form —$CH_2$—$R^{2AB}$—$CH_2$—; and $R^{2AB}$ is —($CH_2$)$_3$—; and so $R^{2A}$ and $R^{2B}$, taken together, form —($CH_2$)$_5$—; and so the group —$NR^{2A}R^{2B}$ is piperidino (from the dialdehyde, glutaraldehyde).

The Groups $R^{1A}$, $R^{1B}$, $R^{2A}$ and $R^{2B}$

In one embodiment:

$R^{1A}$ and $R^{2A}$ are the same; and $R^{1B}$ and $R^{2B}$ are the same.

In one embodiment:

$R^{1A}$ and $R^{2A}$ are the same;

$R^{1B}$ and $R^{2B}$ are the same; and $R^{1A}$ and $R^{1B}$ are the same.

In one embodiment:

$R^{1A}$ and $R^{2A}$ are the same; and $R^{1B}$ and $R^{2B}$ are the same; but $R^{1A}$ and $R^{1B}$ are different.

Some Preferred Embodiments

"N,N-Disubstituted, Same Substituents":

In one embodiment:

$R^{1A}$ is -Me and $R^{1B}$ is -Me (and, accordingly, —$NR^{1A}R^{1B}$ is —$NMe_2$);

$R^{2A}$ is -Me and $R^{2B}$ is -Me (and, accordingly, —$NR^{2A}R^{2B}$ is —$NMe_2$).

In one embodiment:

$R^{1A}$ is -Et and $R^{1B}$ is -Et (and, accordingly, —$NR^{1A}R^{1B}$ is -$NEt_2$);

$R^{2A}$ is -Et and $R^{2B}$ is -Et (and, accordingly, —$NR^{2A}R^{2B}$ is -$NEt_2$).

In one embodiment:

$R^{1A}$ is -nPr and $R^{1B}$ is -nPr (and, accordingly, —$NR^{1A}R^{1B}$ is —N(nPr)$_2$); $R^{2A}$ is -nPr and $R^{2B}$ is -nPr (and, accordingly, —$NR^{2A}R^{2B}$ is —N(nPr)$_2$).

In one embodiment:

$R^{1A}$ is -nBu and $R^{1B}$ is -nBu (and, accordingly, —$NR^{1A}R^{1B}$ is —N(nBu)$_2$); $R^{2A}$ is -nBu and $R^{2B}$ is -nBu (and, accordingly, —$NR^{2A}R^{2B}$ is —N(nBu)$_2$).

"N-Monosubstituted":

In one embodiment:

$R^{1A}$ is -iPr and $R^{1B}$ is —H (and, accordingly, —$NR^{1A}R^{1B}$ is —N(iPr)H);

$R^{2A}$ is -iPr and $R^{2B}$ is —H (and, accordingly, —$NR^{2A}R^{2B}$ is —N(iPr)H).

In one embodiment:

$R^{1A}$ is -iBu and $R^{1B}$ is —H (and, accordingly, —$NR^{1A}R^{1B}$ is —N(iBu)H);

$R^{2A}$ is -iBu and $R^{2B}$ is —H (and, accordingly, —$NR^{2A}R^{2B}$ is —N(iBu)H).

In one embodiment:

$R^{1A}$ is cyclopentyl and $R^{1B}$ is —H (and, accordingly, —$NR^{1A}R^{1B}$ is —N(cyclopentyl)H);

$R^{2A}$ is cyclopentyl and $R^{2B}$ is —H (and, accordingly, —$NR^{2A}R^{2B}$ is —N(cyclopentyl)H).

In one embodiment:

$R^{1A}$ is cyclohexyl and $R^{1B}$ is —H (and, accordingly, —$NR^{1A}R^{1B}$ is —N(cyclohexyl)H);

$R^{2A}$ is cyclohexyl and $R^{2B}$ is —H (and, accordingly, —$NR^{2A}R^{2B}$ is —N(cyclohexyl)H).

"N,N-Disubstituted, Different Substituents":

In one embodiment:

$R^{1A}$ is -iPr and $R^{1B}$ is -Me (and, accordingly, —$NR^{1A}R^{1B}$ is —N(iPr)(Me));

$R^{2A}$ is -iPr and $R^{2B}$ is -Me (and, accordingly, —$NR^{2A}R^{2B}$ is —N(iPr)(Me)).

In one embodiment:

$R^{1A}$ is -iPr and $R^{1B}$ is -Et (and, accordingly, —$NR^{1A}R^{1B}$ is —N(iPr)(Et));

$R^{2A}$ is -iPr and $R^{2B}$ is -Et (and, accordingly, —$NR^{2A}R^{2B}$ is —N(iPr)(Et)).

In one embodiment:

$R^{1A}$ is -iPr and $R^{1B}$ is -nPr (and, accordingly, —$NR^{1A}R^{1B}$ is —N(iPr)(nPr));

$R^{2A}$ is -iPr and $R^{2B}$ is -nPr (and, accordingly, —$NR^{2A}R^{2B}$ is —N(iPr)(nPr)).

In one embodiment:

$R^{1A}$ is -iPr and $R^{1B}$ is -nBu (and, accordingly, —$NR^{1A}R^{1B}$ is —N(iPr)(nBu));

$R^{2A}$ is -iPr and $R^{2B}$ is -nBu (and, accordingly, —$NR^{2A}R^{2B}$ is —N(iPr)(nBu)).

In one embodiment:

$R^{1A}$ is -iBu and $R^{1B}$ is -Me (and, accordingly, —$NR^{1A}R^{1B}$ is —N(iBu)(Me));

$R^{2A}$ is -iBu and $R^{2B}$ is -Me (and, accordingly, —$NR^{2A}R^{2B}$ is —N(iBu)(Me)).

In one embodiment:

$R^{1A}$ is -iBu and $R^{1B}$ is -Et (and, accordingly, —$NR^{1A}R^{1B}$ is —N(iBu)(Et));

$R^{2A}$ is -iBu and $R^{2B}$ is -Et (and, accordingly, —$NR^{2A}R^{2B}$ is —N(iBu)(Et)).

In one embodiment:
$R^{1A}$ is -iBu and $R^{1B}$ is -nPr (and, accordingly, —$NR^{1A}R^{1B}$ is —N(iBu)(nPr));
$R^{2A}$ is -iBu and $R^{2B}$ is -nPr (and, accordingly, —$NR^{2A}R^{2B}$ is —N(iBu)(nPr)).

In one embodiment:
$R^{1A}$ is -iBu and $R^{1B}$ is -nBu (and, accordingly, —$NR^{1A}R^{1B}$ is —N(iBu)(nBu));
$R^{2A}$ is -iBu and $R^{2B}$ is -nBu (and, accordingly, —$NR^{2A}R^{2B}$ is —N(iBu)(nBu)).

"Disubstituted, Ring Forming":

In one embodiment:
$R^{1A}$ and $R^{1B}$ together form —$(CH_2)_4$— (and, accordingly, —$NR^{1A}R^{1B}$ is pyrrolidino);
$R^{2A}$ and $R^{2B}$ together form —$(CH_2)_4$— (and, accordingly, —$NR^{2A}R^{2B}$ is pyrrolidino).

In one embodiment:
$R^{1A}$ and $R^{1B}$ together form —$(CH_2)_5$— (and, accordingly, —$NR^{1A}R^{1B}$ is piperidino);
$R^{2A}$ and $R^{2B}$ together form —$(CH_2)_5$— (and, accordingly, —$NR^{2A}R^{2B}$ is piperidino).

In one embodiment:
$R^{1A}$ and $R^{1B}$ together form —$(CH_2)_6$— (and, accordingly, —$NR^{1A}R^{1B}$ is azepano);
$R^{2A}$ and $R^{2B}$ together form —$(CH_2)_6$— (and, accordingly, —$NR^{2A}R^{2B}$ is azepano).

The Groups $R^3$ and $R^4$

In the compounds described herein:
$R^3$ is independently —H, —$R^{T3}$, —$R^{T3H}$, —F, —Cl, —Br, —I, —OH, —$OR^{T3}$, —$NH_2$, —$NHR^{T3}$, —$NR^{T3}_2$, pyrrolidino, piperidino, morpholino, —C(=O)OH, or —C(=O)$OR^{T3}$; wherein each —$R^{T3}$ is a $C_{1-10}$alkyl group and $R^{T3H}$ is a $C_{1-10}$haloalkyl group; and $R^4$ is independently —H, —$R^{T4}$, —$R^{T4H}$, —F, —Cl, —Br, —I, —OH, —$OR^{T4}$, —$NH_2$, —$NHR^{T4}$, —$NR^{T4}_2$, pyrrolidino, piperidino, morpholino, —C(=O)OH, or —C(=O)$OR^{T4}$; wherein each —$R^{T4}$ is a $C_{1-10}$alkyl group and $R^{T4H}$ is a $C_{1-10}$haloalkyl group.

In one embodiment:
$R^3$ is independently H, $C_{1-10}$alkyl, or $C_{1-10}$haloalkyl; and
$R^4$ is independently H, $C_{1-10}$alkyl, or $C_{1-10}$haloalkyl.

In one embodiment:
$R^3$ is independently H, $C_{1-6}$alkyl, or $C_{1-6}$haloalkyl; and
$R^4$ is independently H, $C_{1-6}$alkyl, or $C_{1-6}$haloalkyl.

In one embodiment:
$R^3$ is independently H, $C_{1-4}$alkyl, or $C_{1-4}$haloalkyl; and
$R^4$ is independently H, $C_{1-4}$alkyl, or $C_{1-4}$haloalkyl.

In one embodiment:
$R^3$ is independently H or $C_{1-4}$alkyl; and
$R^4$ is independently H or $C_{1-4}$alkyl.

In one embodiment:
$R^3$ is independently H; and
$R^4$ is independently H.

In one embodiment:
$R^3$ is independently $C_{1-4}$alkyl; and
$R^4$ is independently $C_{1-4}$alkyl.

In one embodiment, $R^3$ and $R^4$ are the same.
In one embodiment, $R^3$ and $R^4$ are different.
In one embodiment, $R^3$ and $R^4$ are both —H.
In one embodiment, $R^3$ and $R^4$ are both -Me.
In one embodiment, $R^3$ and $R^4$ are both -Et.
In one embodiment, $R^3$ and $R^4$ are both —$CF_3$.

The Groups $R^5$ and $R^6$

In the compounds described herein:
$R^5$ is independently —H, —$R^{T5}$, —$R^{T5H}$, —F, —Cl, —Br, —I, —OH, —$OR^{T5}$, —$NH_2$, —$NHR^{T5}$, —$NR^{T5}_2$, pyrrolidino, piperidino, morpholino, —C(=O)OH, or —C(=O)$OR^{T5}$; wherein each —$R^{T5}$ is a $C_{1-10}$alkyl group and $R^{T5H}$ is a $C_{1-10}$haloalkyl group; and $R^6$ is independently —H, —$R^{T6}$, —$R^{T6H}$, —F, —Cl, —Br, —I, —OH, —$OR^{T6}$, —$NH_2$, —$NHR^{T6}$, —$NR^{T6}_2$, pyrrolidino, piperidino, morpholino, —C(=O)OH, or —C(=O)$OR^{T6}$; wherein each —$R^{T6}$ is a $C_{1-10}$alkyl group and $R^{T6H}$ is a $C_{1-10}$haloalkyl group.

In one embodiment:
$R^5$ is independently H, $C_{1-10}$alkyl, or $C_{1-10}$haloalkyl; and
$R^6$ is independently H, $C_{1-10}$alkyl, or $C_{1-10}$haloalkyl.

In one embodiment:
$R^5$ is independently H, $C_{1-6}$alkyl, or $C_{1-6}$haloalkyl; and
$R^6$ is independently H, $C_{1-6}$alkyl, or $C_{1-6}$haloalkyl.

In one embodiment:
$R^5$ is independently H, $C_{1-4}$alkyl, or $C_{1-4}$haloalkyl; and
$R^6$ is independently H, $C_{1-4}$alkyl, or $C_{1-4}$haloalkyl.

In one embodiment:
$R^5$ is independently H or $C_{1-4}$alkyl; and
$R^6$ is independently H or $C_{1-4}$alkyl.

In one embodiment:
$R^5$ is independently H; and
$R^6$ is independently H.

In one embodiment:
$R^5$ is independently $C_{1-4}$alkyl; and
$R^6$ is independently $C_{1-4}$alkyl.

In one embodiment, $R^5$ and $R^6$ are the same.
In one embodiment, $R^5$ and $R^6$ are different.
In one embodiment, $R^5$ and $R^6$ are both —H.
In one embodiment, $R^5$ and $R^6$ are both -Me.
In one embodiment, $R^5$ and $R^6$ are both -Et.
In one embodiment, $R^5$ and $R^6$ are both —$CF_3$.

The Groups $R^7$ and $R^8$

In the compounds described herein:
$R^7$ is independently —H, —$R^{T7}$, —$R^{T7H}$, —F, —Cl, —Br, —I, —OH, —$OR^{T7}$, —$NH_2$, —$NHR^{T7}$, —$NR^{T7}_2$, pyrrolidino, piperidino, morpholino, —C(=O)OH, or —C(=O)$OR^{T7}$; wherein each —$R^{T7}$ is a $C_{1-10}$alkyl group and $R^{T7H}$ is a $C_{1-10}$haloalkyl group; and $R^8$ is independently —H, —$R^{T8}$, —$R^{T8H}$, —F, —Cl, —Br, —I, —OH, —$OR^{T8}$, —$NH_2$, —$NHR^{T8}$, —$NR^{T8}_2$, pyrrolidino, piperidino, morpholino, —C(=O)OH, or —C(=O)$OR^{T8}$; wherein each —$R^{T8}$ is a $C_{1-10}$alkyl group and $R^{T8H}$ is a $C_{1-10}$haloalkyl group.

In one embodiment:
$R^7$ is independently H, $C_{1-10}$alkyl, or $C_{1-10}$haloalkyl; and
$R^8$ is independently H, $C_{1-10}$alkyl, or $C_{1-10}$haloalkyl.

In one embodiment:
$R^7$ is independently H, $C_{1-6}$alkyl, or $C_{1-6}$haloalkyl; and
$R^8$ is independently H, $C_{1-6}$alkyl, or $C_{1-6}$haloalkyl.

In one embodiment:
$R^7$ is independently H, $C_{1-4}$alkyl, or $C_{1-4}$haloalkyl; and
$R^8$ is independently H, $C_{1-4}$alkyl, or $C_{1-4}$haloalkyl.

In one embodiment:
$R^7$ is independently H or $C_{1-4}$alkyl; and
$R^8$ is independently H or $C_{1-4}$alkyl.

In one embodiment:
$R^7$ is independently H; and
$R^8$ is independently H.
In one embodiment:
$R^7$ is independently $C_{1-4}$alkyl; and
$R^8$ is independently $C_{1-4}$alkyl.
In one embodiment, $R^7$ and $R^8$ are the same.
In one embodiment, $R^7$ and $R^8$ are different.
In one embodiment, $R^7$ and $R^8$ are both —H.
In one embodiment, $R^7$ and $R^8$ are both -Me.
In one embodiment, $R^7$ and $R^8$ are both -Et.
In one embodiment, $R^7$ and $R^8$ are both —$CF_3$.

The Groups $X^{1(-)}$ and $X^{2(-)}$

The groups $X^{1(-)}$ and $X^{2(-)}$ are anionic counterions (e.g., pharmaceutically acceptable anionic counterions) in compounds of Formula (2).

The groups $X^{1(-)}$ and $X^{2(-)}$ may be two separate singly-charged anions (e.g., pharmaceutically acceptable anions), which may be the same or different.

In an example of such an embodiment, each of $X^{1(-)}$ and $X^{2(-)}$ is $Cl^-$.

Alternatively, the groups $X^{1(-)}$ and $X^{2(-)}$ together form one doubly-charged anion (e.g., pharmaceutically acceptable anion).

In an example of such an embodiment, $X^{1(-)}$ and $X^{2(-)}$ together form $SO_4^{2-}$.

In the compounds described herein:
each of $X^{1(-)}$ and $X^{2(-)}$ is independently a singly-charged anion; or
$X^{1(-)}$ and $X^{2(-)}$, taken together, form a doubly-charged anion.

In one embodiment, each of $X^{1(-)}$ and $X^{2(-)}$ is independently a singly-charged anion.

In one embodiment, each of $X^{1(-)}$ and $X^{2(-)}$ is independently a singly-charged anion, and $X^{1(-)}$ and $X^{2(-)}$ are the same.

In one embodiment, each of $X^{1(-)}$ and $X^{2(-)}$ is independently a singly-charged anion, and $X^{1(-)}$ and $X^{2(-)}$ are different (e.g., a "mixed salt").

In one embodiment, $X^{1(-)}$ and $X^{2(-)}$, taken together, form a doubly-charged anion.

In one embodiment, each of $X^{1(-)}$ and $X^{2(-)}$, or $X^{1(-)}$ and $X^{2(-)}$ taken together, are pharmaceutically acceptable ions, and resulting compounds of Formula (2) are pharmaceutically acceptable salts.

Examples of suitable anions include:
inorganic anions derived from the following inorganic acids: hydrofluoric, hydrochloric, hydrobromic, hydroiodic, sulfuric, sulfurous, nitric, nitrous, phosphoric, and phosphorous; and
organic anions derived from the following organic acids: 2-acetyoxybenzoic, acetic, ascorbic, aspartic, benzoic, benzenesulfonic, camphorsulfonic, cinnamic, citric, edetic, ethanedisulfonic, ethanesulfonic, formic, fumaric, glucoheptonic, gluconic, glucuronic, galacturonic, glutamic, glycolic, hydroxymaleic, hydroxynaphthalene carboxylic, isethionic, lactic, lactobionic, lauric, maleic, malic, methanesulfonic, mucic, naphthalenesulfonic, naphthalenedisulfonic, oleic, oxalic, palmitic, pamoic, pantothenic, para-toluenesulfonic, phenylacetic, phenylsulfonic, propanedisulfonic, propionic, pyruvic, salicylic, stearic, succinic, sulfanilic, tartaric, toluenesulfonic, and valeric.

In one embodiment:
$X^{1(-)}$ is independently $F^-$, $Cl^-$, $Br^-$, $NO_3$—, $NO_2$—, or $R^{X1}SO_3^-$; and
$X^{2(-)}$ is independently $F^-$, $Cl^-$, $Br^-$, $NO_3$—, $NO_2$—, or $R^{X2}SO_3^-$; or
$X^{1(-)}$ and $X^{2(-)}$, taken together, form $SO_4^{2-}$ or $R^Y(SO_3)_2^{2-}$;
wherein:
$R^{X1}$ is independently $C_{1-10}$alkyl, $C_{1-10}$haloalkyl, $C_{3-6}$cycloalkyl, or $C_{6-10}$carboaryl;
$R^{X2}$ is independently $C_{1-10}$alkyl, $C_{1-10}$haloalkyl, $C_{3-6}$cycloalkyl, or $C_{6-10}$carboaryl; and
$R^Y$ is independently $C_{1-6}$alkylene or $C_{6-10}$carboarylene;
wherein:
each $C_{3-6}$cycloalkyl, each $C_{6-10}$carboaryl, and each $C_{6-10}$carboarylene is optionally substituted with one or more $C_{1-4}$alkyl groups.

TABLE 1

Examples of $R^{X1}/R^{X2}/R^{X3}$

| $R^{X1}/R^{X2}/R^{X3}$ | Corresponding Anion | Corresponding Acid |
| --- | --- | --- |
| —Me | $MeSO_3^-$ (mesylate) | methanesulfonic acid (MsOH) |
| —Et | $EtSO_3^-$ (esylate) | ethanesulfonic acid (EsOH) |
| phenyl | (Phenyl)$SO_3^-$ | benzenesulfonic acid (BSA) |
| tolyl | (Tolyl)$SO_3^-$ | p-toluenesulfonic acid (TsOH) |
| naphthyl | (Naphthyl)$SO_3^-$ | naphthalenesulfonic acid (NSA) |

In one embodiment:

TABLE 2

Examples of $R^Y$

| $R^Y$ | Corresponding Anion | Corresponding Acid |
| --- | --- | --- |
| —$CH_2CH_2$— | —$O_3SCH_2CH_2SO_3$— | ethanedisulfonic acid (EDSA) |
| —$CH_2CH_2CH_2$— | —$O_3SCH_2CH_2CH_2SO_3$— | propanedisulfonic acid (PDSA) |
| naphthalene-di-yl | —$O_3S$(naphthalene-di-yl)$SO_3$— | naphthalenedisulfonic acid (NDSA) |

$X^{1(-)}$ is independently $F^-$, $Cl^-$, $Br^-$, $NO_3$—, $NO_2$—, or $R^{X1}SO_3^-$; and
$X^{2(-)}$ is independently $F^-$, $Cl^-$, $Br^-$, $NO_3$—, $NO_2$—, or $R^{X2}SO_3^-$.

In one embodiment:
$X^{1(-)}$ is independently $F^-$, $Cl^-$, $Br^-$, or $R^{X1}SO_3^-$; and
$X^{2(-)}$ is independently $F^-$, $Cl^-$, $Br^-$, or $R^{X2}SO_3$.

In one embodiment:
$X^{1(-)}$ is independently $F^-$, $Cl^-$, or $Br^-$; and
$X^{2(-)}$ is independently $F^-$, $Cl^-$, or $Br^-$.

In one embodiment:
$X^{1(-)}$ is independently $R^{X1}SO_3^-$; and
$X^{2(-)}$ is independently $R^{X2}SO_3^-$.

In one embodiment:
$X^{1(-)}$ and $X^{2(-)}$, taken together, form $SO_4^{2-}$ or $R^Y(SO_3)_2^{2-}$.

In one embodiment:
$X^{1(-)}$ and $X^{2(-)}$, taken together, form $R^Y(SO_3)_2^{2-}$.

The Groups $R^{X1}$, $R^{X2}$, and $R^Y$
In one embodiment:
$R^{X1}$, if present, is independently $C_{1-10}$alkyl, $C_{1-10}$haloalkyl, $C_{3-6}$cycloalkyl, or $C_{6-10}$carboaryl;
$R^{X2}$, if present, is independently $C_{1-10}$alkyl, $C_{1-10}$haloalkyl, $C_{3-6}$cycloalkyl, or $C_{6-10}$carboaryl; and
$R^Y$, if present, is independently $C_{1-6}$alkylene or $C_{6-10}$carboarylene;

27 wherein:
  each $C_{3-6}$cycloalkyl, each $C_{6-10}$carboaryl, and each $C_{6-10}$carboarylene is optionally substituted with one or more $C_{1-4}$alkyl groups.

In one embodiment:
  $R^{X1}$, if present, is independently $C_{1-6}$alkyl, $C_{1-6}$haloalkyl, $C_{3-6}$cycloalkyl, or $C_{6-10}$carboaryl;
  $R^{X2}$, if present, is independently $C_{1-6}$alkyl, $C_{1-6}$haloalkyl, $C_{3-6}$cycloalkyl, or $C_{6-10}$carboaryl; and
  $R^{Y}$, if present, is independently $C_{1-6}$alkylene or $C_{6-10}$carboarylene;
wherein:
  each $C_{3-6}$cycloalkyl, each $C_{6-10}$carboaryl, and each $C_{6-10}$carboarylene is optionally substituted with one or more $C_{1-4}$alkyl groups.

In one embodiment:
  $R^{X1}$, if present, is independently $C_{1-4}$alkyl, $C_{1-4}$haloalkyl, $C_{3-6}$cycloalkyl, or $C_{6-10}$carboaryl;
  $R^{X2}$, if present, is independently $C_{1-4}$alkyl, $C_{1-4}$haloalkyl, $C_{3-6}$cycloalkyl, or $C_{6-10}$carboaryl; and
  $R^{Y}$, if present, is independently $C_{1-6}$alkylene or $C_{6-10}$carboarylene;
wherein:
  each $C_{3-6}$cycloalkyl, each $C_{6-10}$carboaryl, and each $C_{6-10}$carboarylene is optionally substituted with one or more $C_{1-4}$alkyl groups.

In one embodiment:
  $R^{X1}$, if present, is independently $C_{1-4}$alkyl, $C_{3-6}$cycloalkyl, or $C_{6-10}$carboaryl;
  $R^{X2}$, if present, is independently $C_{1-4}$alkyl, $C_{3-6}$cycloalkyl, or $C_{6-10}$carboaryl; and
  $R^{Y}$, if present, is independently $C_{1-6}$alkylene or $C_{6-10}$carboarylene;
wherein:
  each $C_{3-6}$cycloalkyl, each $C_{6-10}$carboaryl, and each $C_{6-10}$carboarylene is optionally substituted with one or more $C_{1-4}$alkyl groups.

In one embodiment:
  $R^{X1}$, if present, is independently -Me, -Et, phenyl, tolyl, or naphthyl;
  $R^{X2}$, if present, is independently -Me, -Et, phenyl, tolyl, or naphthyl; and
  $R^{Y}$, if present, is independently —$(CH_2)_2$—, —$(CH_2)_3$—, phenylene, or naphthalene-di-yl.

In one embodiment:
  $X^{1(-)}$, if present, is independently $F^-$; and $X^{2(-)}$, if present, is independently $F^-$.

In one embodiment:
  $X^{1(-)}$, if present, is independently $Cl^-$; and
  $X^{2(-)}$, if present, is independently $Cl^-$.

In one embodiment:
  $X^{1(-)}$, if present, is independently $Br^-$; and
  $X^{2(-)}$, if present, is independently $Br^-$.

In one embodiment:
  $X^{1(-)}$, if present, is independently $MeSO_3^-$; and
  $X^{2(-)}$, if present, is independently $MeSO_3^-$.

In one embodiment:
  $X^{1(-)}$, if present, is independently $EtSO_3^-$; and
  $X^{2(-)}$, if present, is independently $EtSO_3^-$.

In one embodiment:
  $X^{1(-)}$, if present, is independently (phenyl)$SO_3^-$; and
  $X^{2(-)}$, if present, is independently (phenyl)$SO_3^-$.

In one embodiment:
  $X^{1(-)}$, if present, is independently (tolyl)$SO_3^-$; and
  $X^{2(-)}$, if present, is independently (tolyl)$SO_3^-$.

28

In one embodiment:
  $X^{1(-)}$, if present, is independently (naphthyl)$SO_3^-$; and
  $X^{2(-)}$, if present, is independently (naphthyl)$SO_3^-$.

In one embodiment:
  $X^{1(-)}$ and $X^{2(-)}$, if present, taken together, form $R^{Y}(SO_3)_2^{2-}$; and
  $R^{Y}$ is —$(CH_2)_2$—.

In one embodiment:
  $X^{1(-)}$ and $X^{2(-)}$, if present, taken together, form $R^{Y}(SO_3)_2^{2-}$; and
  $R^{Y}$ is —$(CH_2)_3$—.

In one embodiment:
  $X^{1(-)}$ and $X^{2(-)}$, if present, taken together, form $R^{Y}(SO_3)_2^{2-}$; and
  $R^{Y}$ is phenylene (e.g., 1,4-phenylene).

In one embodiment:
  $X^{1(-)}$ and $X^{2(-)}$, if present, taken together, form $R^{Y}(SO_3)_2^{2-}$; and
  $R^{Y}$ is naphthalene-di-yl (e.g., naphthalene-1,5-di-yl; naphthalene-1,8-di-yl).

The Group $X^{3(-)}$

The group $X^{3(-)}$ is an anionic counterion (e.g., pharmaceutically acceptable anionic counterion) in compounds of Formula (3).

The group $X^{3(-)}$ may be a singly-charged anion (e.g., pharmaceutically acceptable anion).

In an example of such an embodiment, $X^{3(-)}$ is $Cl^-$.

Alternatively, the group $X^{3(-)}$ may be a multiply-charged (e.g., doubly-charged) anion (e.g., pharmaceutically acceptable anion). In such cases, the molar ratio of the thioninium cation to the counter anion is a corresponding multiple.

In an example of such an embodiment, $X^{3(-)}$ is $SO_4^{2-}$ (and the molar ratio of thioninium cation to counter anion is 2, or equivalently, the molar ratio of counter anion to thioninium cation is 0.5).

In the compounds described herein, $X^{3(-)}$ is an anion (e.g., a pharmaceutically acceptable anion), corresponding to an acid.

In one embodiment, $X^{3(-)}$ is independently a single-charged anion (e.g., pharmaceutically acceptable anion), corresponding to an acid, $HX^3$.

In one embodiment, $X^{3(-)}$ is independently a doubly-charged anion (e.g., pharmaceutically acceptable anion), corresponding to an acid, $H_2X^3$.

Examples of suitable anions include:
  inorganic anions derived from the following inorganic acids: hydrofluoric, hydrochloric, hydrobromic, hydroiodic, sulfuric, sulfurous, nitric, nitrous, phosphoric, and phosphorous; and
  organic anions derived from the following organic acids: 2-acetyoxybenzoic, acetic, ascorbic, aspartic, benzoic, benzenesulfonic, camphorsulfonic, cinnamic, citric, edetic, ethanedisulfonic, ethanesulfonic, formic, fumaric, glucoheptonic, gluconic, glucuronic, galacturonic, glutamic, glycolic, hydroxymaleic, hydroxynaphthalene carboxylic, isethionic, lactic, lactobionic, lauric, maleic, malic, methanesulfonic, mucic, naphthalenesulfonic, naphthalenedisulfonic, oleic, oxalic, palmitic, pamoic, pantothenic, para-toluenesulfonic, phenylacetic, phenylsulfonic, propanedisulfonic, propionic, pyruvic, salicylic, stearic, succinic, sulfanilic, tartaric, toluenesulfonic, and valeric.

In one embodiment:
  $X^{3(-)}$, if present, is independently $F^-$, $Cl^-$, $Br^-$, $NO_3^-$, $NO_2^-$, or $R^{X3}SO_3^-$;

wherein:
R$^{X3}$ is independently C$_{1-10}$alkyl, C$_{1-10}$-haloalkyl, C$_{3-6}$cycloalkyl, or C$_{6-10}$carboaryl;
wherein:
C$_{3-6}$cycloalkyl and C$_{6-10}$carboaryl are optionally substituted with one or more C$_{1-4}$alkyl groups.

In one embodiment, X$^{3(-)}$, if present, is independently F$^-$, Cl$^-$, Br$^-$, or R$^{X3}$SO$_3{}^-$.

In one embodiment, X$^{3(-)}$, if present, is independently F$^-$, Cl$^-$, Br$^-$.

In one embodiment, X$^{3(-)}$, if present, is independently F$^-$.

In one embodiment, X$^{3(-)}$, if present, is independently Cl$^-$.

In one embodiment, X$^{3(-)}$, if present, is independently Br$^-$.

In one embodiment, X$^{3(-)}$, if present, is independently R$^{X3}$SO$_3{}^-$.

In one embodiment, R$^{X3}$, if present, is independently C$_{1-6}$alkyl, C$_{1-6}$haloalkyl, C$_{3-6}$cycloalkyl, or C$_{6-10}$carboaryl; wherein C$_{3-6}$cycloalkyl and C$_{6-10}$carboaryl are optionally substituted with one or more C$_{1-4}$alkyl groups.

In one embodiment, R$^{X3}$, if present, is independently C$_{1-4}$alkyl, C$_{1-4}$haloalkyl, C$_{3-6}$cycloalkyl, or C$_{6-10}$carboaryl; wherein C$_{3-6}$cycloalkyl and C$_{6-10}$carboaryl are optionally substituted with one or more C$_{1-4}$alkyl groups.

In one embodiment, R$^{X3}$, if present, is independently C$_{1-4}$alkyl, C$_{3-6}$cycloalkyl, or C$_{6-10}$carboaryl; wherein C$_{3-6}$cycloalkyl and C$_{6-10}$carboaryl are optionally substituted with one or more C$_{1-4}$alkyl groups.

In one embodiment, R$^{X3}$, if present, is independently C$_{1-4}$alkyl or C$_{6-10}$carboaryl; wherein C$_{6-10}$carboaryl is optionally substituted with one or more C$_{1-4}$alkyl groups.

In one embodiment, R$^{X3}$, if present, is independently -Me, -Et, phenyl, tolyl, or naphthyl; In one embodiment, X$^{3(-)}$, if present, is independently MeSO$_3{}^-$.

In one embodiment, X$^{3(-)}$, if present, is independently EtSO$_3$.

In one embodiment, X$^{3(-)}$, if present, is independently (phenyl)SO$_3{}^-$.

In one embodiment, X$^{3(-)}$, if present, is independently (tolyl)SO$_3{}^-$.

In one embodiment, X$^{3(-)}$, if present, is independently (naphthyl)SO$_3{}^-$.

In one embodiment, X$^{3(-)}$, if present, is independently (naphth-1-yl)SO$_3{}^-$.

In one embodiment, X$^{3(-)}$, if present, is independently (naphth-2-yl)SO$_3$.

Alkyl Groups

In one embodiment, the or each C$_{1-10}$alkyl is C$_{1-6}$alkyl.
In one embodiment, the or each C$_{1-10}$alkyl is C$_{1-4}$alkyl.
In one embodiment, the or each C$_{1-6}$alkyl is C$_{1-4}$alkyl.
In one embodiment, the or each alkyl (e.g., C$_{1-10}$alkyl, C$_{1-6}$alkyl, C$_{1-4}$alkyl) is independently: -Me, -Et, -nPr, -iPr, -nBu, or -iBu.
In one embodiment, the or each alkyl (e.g., C$_{1-10}$alkyl, C$_{1-6}$alkyl, C$_{1-4}$alkyl) is independently: -Me, -Et, -nPr, or -iPr.
In one embodiment, the or each alkyl (e.g., C$_{1-10}$alkyl, C$_{1-6}$alkyl, C$_{1-4}$alkyl) is independently: -Me or -Et.
In one embodiment, the or each alkyl (e.g., C$_{1-10}$alkyl, C$_{1-6}$alkyl, C$_{1-4}$alkyl) is -Me.
In one embodiment, the or each alkyl (e.g., C$_{1-10}$alkyl, C$_{1-6}$alkyl, C$_{1-4}$alkyl) is -Et.
In one embodiment, the or each alkyl (e.g., C$_{1-10}$alkyl, C$_{1-6}$alkyl, C$_{1-4}$alkyl) is -nPr.
In one embodiment, the or each alkyl (e.g., C$_{1-10}$alkyl, C$_{1-6}$alkyl, C$_{1-4}$alkyl) is -iPr.
In one embodiment, the or each alkyl (e.g., C$_{1-10}$alkyl, C$_{1-6}$alkyl, C$_{1-4}$alkyl) is -nBu.
In one embodiment, the or each alkyl (e.g., C$_{1-10}$alkyl, C$_{1-6}$alkyl, C$_{1-4}$alkyl) is -iBu.

Haloalkyl Groups

For the avoidance of doubt, the term "haloalkyl" (e.g., C$_{1-10}$haloalkyl, C$_{1-6}$haloalkyl, C$_{1-4}$haloalkyl), as used herein, relates to an alkyl group (e.g., a C$_{1-10}$alkyl group, a C$_{1-6}$alkyl group, a C$_{1-4}$alkyl group) in which each of one or more hydrogen atoms has been replaced with a halogen atom, typically the same halogen atom.

In one embodiment, the or each C$_{1-4}$haloalkyl is —CF$_3$, —CH$_2$CF$_3$, or —CH$_2$CH$_2$F.

In one embodiment, the or each C$_{1-4}$haloalkyl is —CF$_3$.

Cycloalkyl Groups

In one embodiment, the or each C$_{3-6}$cycloalkyl is C$_{5-6}$cycloalkyl.

In one embodiment, the or each C$_{3-6}$cycloalkyl is cyclopropyl.

In one embodiment, the or each C$_{3-6}$cycloalkyl is cyclobutyl.

In one embodiment, the or each cycloalkyl (e.g., C$_{3-6}$cycloalkyl, C$_{5-6}$cycloalkyl) is cyclopentyl.

In one embodiment, the or each cycloalkyl (e.g., C$_{3-6}$cycloalkyl, C$_{5-6}$cycloalkyl) is cyclohexyl.

Alkylene Groups

For the avoidance of doubt, the term "alkylene" is used herein in the conventional sense to refer to a substituent which is derived from an alkane, and which has two points of attachment, wherein each attachment is via a carbon atom, and is provided by the removal of a hydrogen atom. For example, for the alkane methane (i.e., CH$_4$), the corresponding alkyl group is methyl (i.e., —CH$_3$), and the corresponding alkylene group is methylene (i.e., —CH$_2$—).

In one embodiment, the or each C$_{1-6}$alkylene is C$_{1-4}$alkylene.

In one embodiment, the or each C$_{1-6}$alkylene is C$_{2-4}$alkylene.

In one embodiment, the or each C$_{1-6}$alkylene is C$_{4-6}$alkylene.

In one embodiment, the or each C$_{1-6}$alkylene is linear C$_{1-4}$alkylene.

In one embodiment, the or each C$_{1-6}$alkylene is linear C$_{2-4}$alkylene.

In one embodiment, the or each C$_{1-6}$alkylene is linear C$_{4-6}$alkylene.

In one embodiment, the or each C$_{4-6}$alkylene is linear C$_4$alkylene (i.e., —(CH$_2$)$_4$—).

In one embodiment, the or each C$_{4-6}$alkylene is linear C$_5$alkylene (i.e., —(CH$_2$)$_5$—).

In one embodiment, the or each C$_{4-6}$alkylene is linear C$_6$alkylene (i.e., —(CH$_2$)$_6$—).

In one embodiment, the or each alkylene (e.g., C$_{1-6}$alkylene, C$_{1-4}$alkylene) is methylene (i.e., —CH$_2$—).

In one embodiment, the or each alkylene (e.g., C$_{1-6}$alkylene, C$_{1-4}$alkylene, C$_{2-4}$alkylene) is ethylene (i.e., —(CH$_2$)$_2$—).

In one embodiment, the or each alkylene (e.g., C$_{1-6}$alkylene, C$_{1-4}$alkylene, C$_{2-4}$alkylene) is propylene (i.e., —(CH$_2$)$_3$—).

In one embodiment, the or each alkylene (e.g., C$_{1-6}$alkylene, C$_{1-4}$alkylene, C$_{2-4}$alkylene, C$_{4-6}$alkylene) is butylene (i.e., —(CH$_2$)$_4$—).

In one embodiment, the or each alkylene (e.g., C$_{1-6}$alkylene, C$_{4-6}$alkylene) is pentylene (i.e., —(CH$_2$)$_5$—).

In one embodiment, the or each alkylene (e.g., C$_{1-6}$alkylene, C$_{4-6}$alkylene) is hexylene (i.e., —(CH$_2$)$_6$—).

Carboaryl Groups

In one embodiment, the or each $C_{6-10}$carboaryl is phenyl or naphthyl.

In one embodiment, the or each $C_{6-10}$carboaryl is phenyl.

In one embodiment, the or each $C_{6-10}$carboaryl is unsubstituted.

Methods of Synthesis

Selective Alkylation by Reductive Amination

The methods of synthesis proceed via a step of selective alkylation by reductive amination, in which a compound of Formula (4):

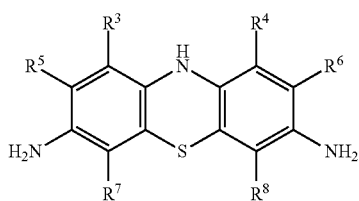

Formula (4)

is reacted with aldehyde/ketone and a reductive amination agent, under reductive amination conditions, to give the corresponding compound of Formula (1):

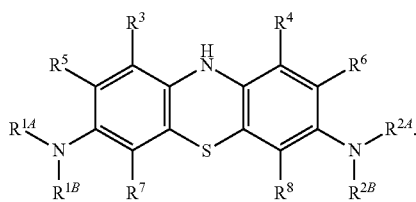

Formula (1)

In the reductive amination reaction, a carbonyl group, (O=)C<, of the aldehyde/ketone gives rise to a corresponding nitrogen substituent, —CH<. Accordingly, any suitable aldehyde/ketone may be used, to give rises to the corresponding nitrogen substituent attached via a —CH< group.

For the avoidance of doubt, the term "aldehyde/ketone", as used herein, denotes an aldehyde, a ketone, a mixture of aldehydes, a mixture of ketones, or a mixture of aldehydes and ketones.

Also for the avoidance of doubt, the term "aldehyde", as used herein, is intended to encompass both monomeric aldehyde and polymeric aldehyde, unless otherwise specified. For example, formaldehyde, H—C(=O)—H, is monomeric, and a corresponding polymeric aldehyde is paraformaldehyde, HO—[CH$_2$—O]n-H. Accordingly, unless otherwise specified a reference to formaldehyde is intended to encompass polymeric formaldehyde, e.g., paraformaldehyde. Similarly, acetaldehyde, CH$_3$—C(=O)—H, is monomeric, and corresponding polymeric aldehydes include a cyclic trimer (paraldehyde), a cylic tetramer (metaldehyde), and more generally polyacetaldehyde, HO—[CH(CH$_3$)—O]n-H. Accordingly, unless otherwise specified a reference to acetaldehyde is intended to encompass polymeric acetaldehyde, e.g., paraldehyde, metaldehyde, polyacetaldehyde, etc.

Surprisingly and unexpectedly, the alkylation by reductive amination is selective, that is, the alkylation is selective for the pendant amino groups at the 3- and 7-positions in compounds of Formula (4), as compared to the bridging amino group at the 10-position in compounds of Formula (4). Surprisingly and unexpectedly, alkylation by reductive amination preferentially occurs at the pendant amino groups at the 3- and 7-positions, even to the point of di-alkylation at both of those positions, with little or no alkylation occurring at the bridging amino group at the 10-position.

Possible Mechanisms

Without wishing to be bound to any particular theory, possible mechanisms for the selective alkylation by reductive amination are illustrated in the following schemes.

A possible mechanism for the first selective alkylation by reductive amination is shown in the following scheme, in which a first aldehyde or ketone, $R^{1AX}$—C(=O)—$R^{1AY}$, is used for a first alkylation, to give $R^{1A}$ as —CH($R^{1AX}$)($R^{1AY}$).

Scheme 1

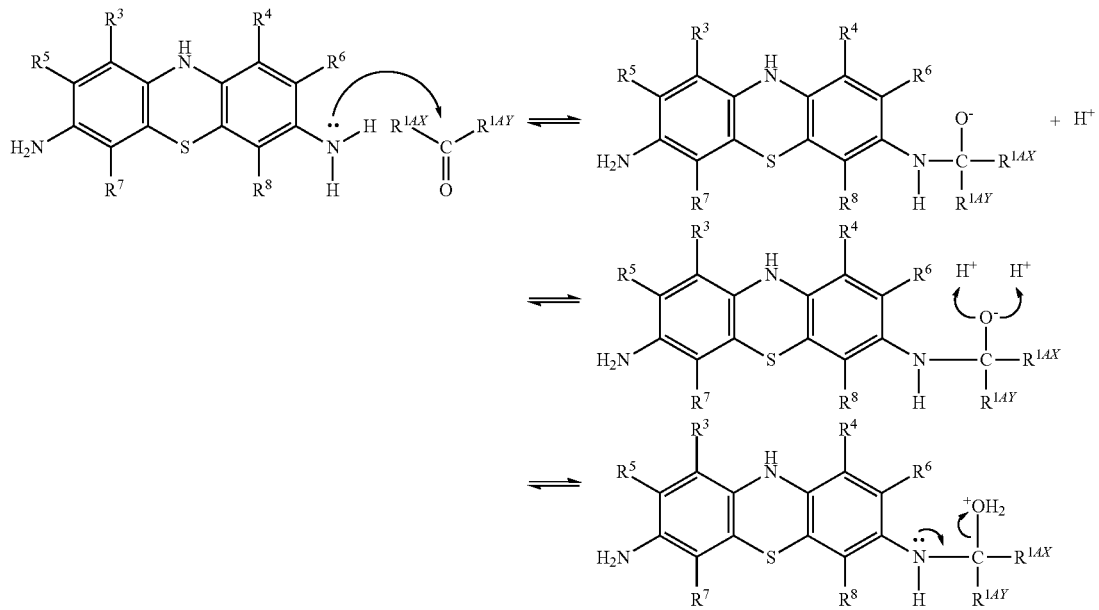

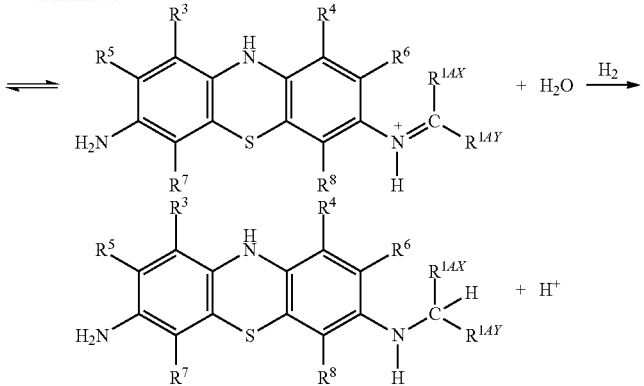

This first selective alkylation by reductive amination may be abbreviated as shown in the following scheme, in which a first aldehyde or ketone, $R^{1AX}-C(=O)-R^{1AY}$, is used for a first alkylation, to give $R^{1A}$ as $-CH(R^{1AX})(R^{1AY})$.

Scheme 2

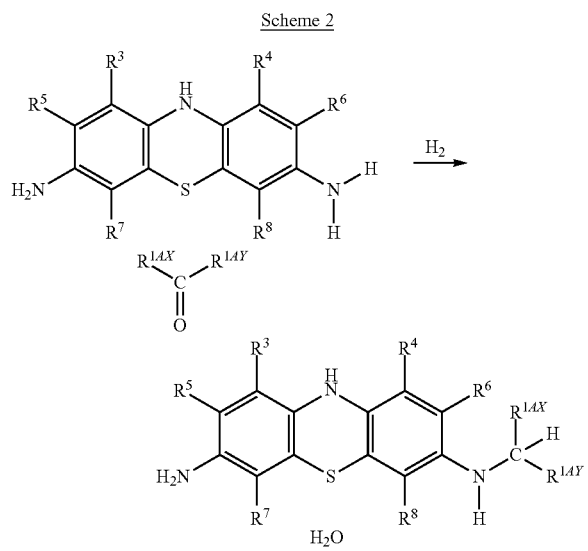

A similar second selective alkylation by reductive amination may be abbreviated as shown in the following scheme, in which a second aldehyde or ketone, $R^{2AX}-C(=O)-R^{2AY}$, is used for a second alkylation, to give $R^{2A}$ as $-CH(R^{2AX})(R^{2AY})$ Scheme 3

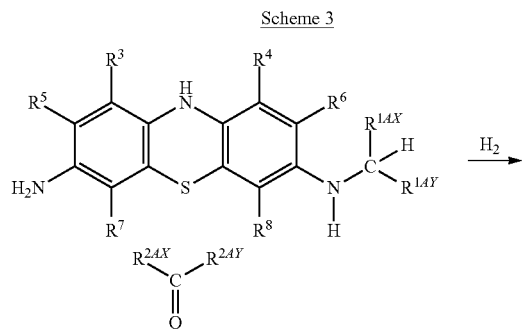

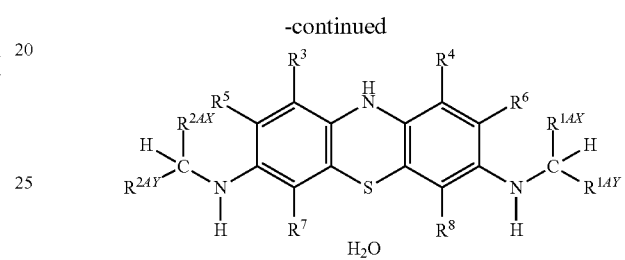

It is possible to stop here, and obtain "N-monosubstituted" compounds (i.e., wherein each of $R^{1B}$ and $R^{2B}$ is $-H$). Alternatively, the process may be continued as described below.

If the process is to be continued, as described below, and if $R^{1B}$ and/or $R^{2B}$ are to be different from $R^{1A}$ and/or $R^{2A}$, then it may be necessary to do the sterically larger groups "first" (as $R^{1A}$ and/or $R^{2A}$) and the sterically smaller groups "second" (as $R^{1B}$ and/or $R^{2B}$). Also, it may be desirable to isolate the N-monosubstituted compound before further reaction.

A similar third selective alkylation by reductive amination may be abbreviated as shown in the following scheme, in which a third aldehyde or ketone, $R^{1BX}-C(=O)-R^{1BY}$, is used for a third alkylation, to give $R^{1B}$ as $-CH(R^{1BX})(R^{1BY})$ Scheme 4

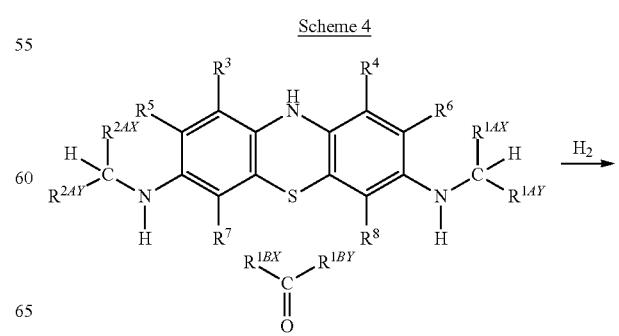

-continued

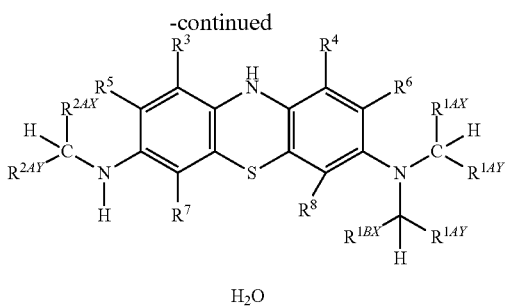

H₂O

A similar fourth selective alkylation by reductive amination may be abbreviated as shown in the following scheme, in which a fourth aldehyde or ketone, $R^{2BX}$—C(=O)—$R^{2BY}$, is used for a fourth alkylation, to give $R^{2B}$ as —CH($R^{2BX}$)($R^{2BY}$).

Scheme 5

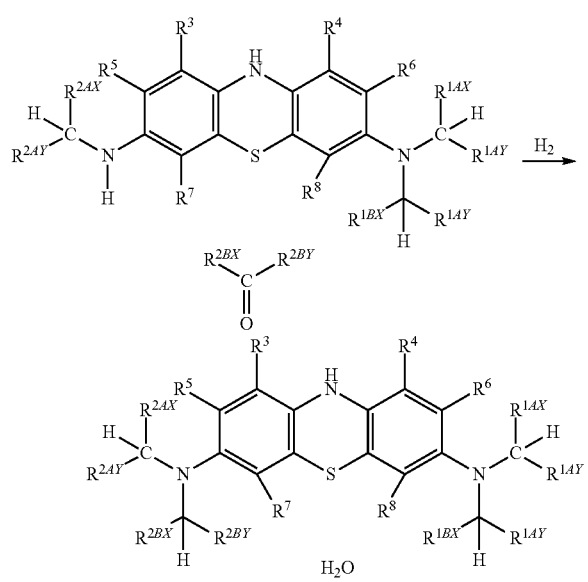

The Aldehyde/Ketone

Again, in the reductive amination reaction, a carbonyl group, (O=)C<, of the aldehyde/ketone gives rise to a corresponding nitrogen substituent, —CH<. Accordingly, any suitable aldehyde/ketone may be used.

Again, for the avoidance of doubt, the term "aldehyde/ketone", as used herein, denotes an aldehyde, a ketone, a mixture of aldehydes, a mixture of ketones, or a mixture of aldehydes and ketones.

Again, for the avoidance of doubt, the term "aldehyde", as used herein, is intended to encompass both monomeric aldehyde and polymeric aldehyde, unless otherwise specified.

For example, formaldehyde, H—C(=O)—H, is monomeric, and a corresponding polymeric aldehyde is paraformaldehyde, HO—[CH₂—O]n-H. Accordingly, unless otherwise specified a reference to formaldehyde is intended to encompass polymeric formaldehyde, e.g., paraformaldehyde. Similarly, acetaldehyde, CH₃—C(=O)—H, is monomeric, and corresponding polymeric aldehydes include a cyclic trimer (paraldehyde), a cylic tetramer (metaldehyde), and more generally polyacetaldehyde, HO—[CH(CH₃)—O]n-H. Accordingly, unless otherwise specified a reference to acetaldehyde is intended to encompass polymeric acetaldehyde, e.g., paraldehyde, metaldehyde, polyacetaldehyde, etc.

In one embodiment, the aldehyde is monomeric aldehyde.

In one embodiment, the aldehyde is polymeric aldehyde (e.g., paraformaldehyde, paraldehyde, metaldehyde, polyacetaldehyde, etc.).

If a particular nitrogen substituent (i.e., $R^{1A}$, $R^{1B}$, $R^{2A}$, $R^{2B}$) is wanted, then the corresponding aldehyde or ketone is used.

For example, if $R^{1A}$ is to be —CH₃ (i.e., —CH(H)(H)), then formaldehyde (HC(=O)H) is used.

Similarly, if $R^{1A}$ is to be -Et (i.e., —CH(H)(CH₃)), then acetaldehyde (HC(=O)CH₃) is used.

Similarly, if $R^{1A}$ is to be -iPr (i.e., —CH(CH₃)₂), then acetone (CH₃C(=O)CH₃) is used.

Similarly, if $R^{1A}$ is to be cyclohexyl (i.e., —CH[—(CH₂)₅—]), then cyclohexanone (i.e., (O=)C[—(CH₂)₅—]), is used.

Similarly, if $R^{1A}$ and $R^{1B}$, taken together, are to form —(CH₂)₅— (i.e., —CH(H)—(CH₂)₃—CH(H)—), so that —N$R^{1A}R^{1B}$ is piperidino, then glutaraldehyde ((O=)CH—(CH₂)₃—CH(=O)) is used.

For example, in one embodiment, a compound of Formula (4a):

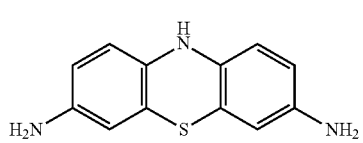

Formula (4a)

is reacted with formaldehyde (e.g., provided as formaldehyde, paraformaldehyde, etc.), under reductive amination conditions, to give the corresponding compound of Formula (1a):

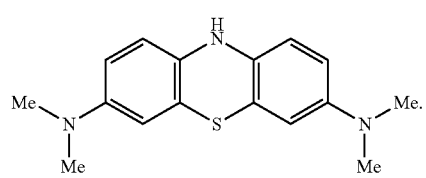

Formula (1a)

In this embodiment:
$R^{1A}$ is —CH₃ (i.e., —CH(H)(H), that is, a substituent attached via a —CH< group);
$R^{1B}$ is —CH₃ (i.e., —CH(H)(H), that is, a substituent attached via a —CH< group);
$R^{2A}$ is —CH₃ (i.e., —CH(H)(H), that is, a substituent attached via a —CH< group); and
$R^{2B}$ is —CH₃ (i.e., —CH(H)(H), that is, a substituent attached via a —CH< group);
and the aldehyde/ketone is H—C(=O)—H (i.e., (O=)C<, i.e., (O=)C(H)(H));
or more specifically:
$R^{1A}$ is —CH($R^{1AX}$)($R^{1AY}$), and is —CH₃;
$R^{1B}$ is —CH($R^{1BX}$)($R^{1BY}$), and is —CH₃;
$R^{2A}$ is —CH($R^{2AX}$)($R^{2AY}$), and is —CH₃; and
$R^{2B}$ is —CH($R^{2BX}$)($R^{2BY}$), and is —CH₃;

and the aldehyde/ketone is H—C(=O)—H:
  $R^{1AX}$—C(=O)—$R^{1AY}$, where $R^{1AX}$ and $R^{1AY}$ are both —H;
  $R^{1BX}$—C(=O)—$R^{1BY}$, where $R^{1BX}$ and $R^{1BY}$ are both —H;
  $R^{2AX}$—C(=O)—$R^{2AY}$, where $R^{2AX}$ and $R^{2A}$ are both —H; and
  $R^{2BX}$—C(=O)—$R^{2BY}$, where $R^{2BX}$ and $R^{2BY}$ are both —H.

Similarly, in one embodiment, a compound of the following formula:

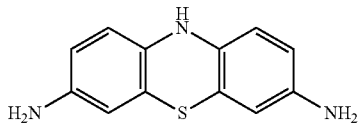

Formula (4a)

is reacted with a mixture of acetone and formaldehyde (e.g., provided as formaldehyde, paraformaldehyde, etc.), under reductive amination conditions, to give the corresponding compound of the following formula:

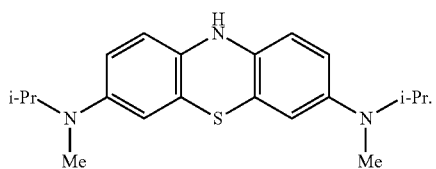 [SMILES: CC(C)N(C)c1ccc2c(c1)Sc1cc(N(C)C(C)C)ccc1N2]

In this embodiment:
$R^{1A}$ is —CH($R^{1AX}$)($R^{1AY}$), and is —CH(CH$_3$)$_2$;
$R^{1B}$ is —CH($R^{1BX}$)($R^{1BY}$), and is —CH$_3$;
$R^{2A}$ is —CH($R^{2AX}$)($R^{2AY}$), and is —CH(CH$_3$)$_2$; and
$R^{2B}$ is —CH($R^{2BX}$)($R^{2BY}$), and is —CH$_3$;
and the aldehyde/ketone is a mixture of CH$_3$—C(=O)—CH$_3$ and H—C(=O)—H:
  $R^{1AX}$—C(=O)—$R^{1AY}$, where $R^{1AX}$ and $R^{1AY}$ are both —CH$_3$;
  $R^{1BX}$—C(=O)—$R^{1BY}$, where $R^{1BX}$ and $R^{1BY}$ are both —H;
  $R^{2AX}$—C(=O)—$R^{2AY}$, where $R^{2AX}$ and $R^{2AY}$ are both —CH$_3$; and
  $R^{2BX}$—C(=O)—$R^{2BY}$, where $R^{2BX}$ and $R^{2BY}$ are both —H.

Similarly, in one embodiment, a compound of the following formula:

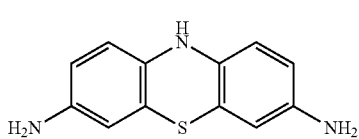

Formula (4a)

is reacted with acetone, under reductive amination conditions, to give the corresponding compound of the following formula:

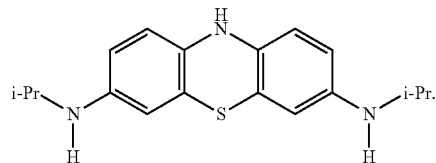 [SMILES: CC(C)Nc1ccc2c(c1)Sc1cc(NC(C)C)ccc1N2]

In this embodiment:
$R^{1A}$ is —CH(CH$_3$)$_2$ (i.e., —CH(CH$_3$)(CH$_3$)), that is, a substituent attached via a —CH< group);
$R^{1B}$ is —H;
$R^{2A}$ is —CH(CH$_3$)$_2$ (i.e., —CH(CH$_3$)(CH$_3$)), that is, a substituent attached via a —CH< group);
$R^{2B}$ is —H;
and the aldehyde/ketone is CH$_3$—C(=O)—CH$_3$ (i.e., (O=)C<, i.e., (O=)C(CH$_3$)(CH$_3$));
or more specifically:
$R^{1A}$ is —CH($R^{1AX}$)($R^{1AY}$), and is —CH(CH$_3$)$_2$;
$R^{1B}$ is —H;
$R^{2A}$ is —CH($R^{2AX}$)($R^{2AY}$), and is —CH(CH$_3$)$_2$; and
$R^{2B}$ is —H;
and the aldehyde/ketone is CH$_3$—C(=O)—CH$_3$:
  $R^{1AX}$—C(=O)—$R^{1AY}$, where $R^{1AX}$ and $R^{1AY}$ are both —CH$_3$; and
  $R^{2AX}$—C(=O)—$R^{2AY}$, where $R^{2AX}$ and $R^{2A}$ are both —CH$_3$.

Similarly, in one embodiment, a compound of the following formula:

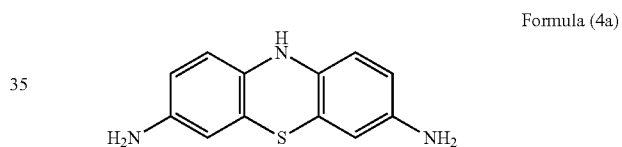

Formula (4a)

is reacted with cyclohexanone, under reductive amination conditions, to give the corresponding compound of the following formula:

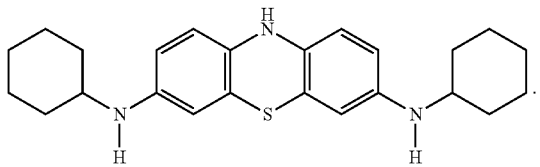 [SMILES: c1cc2c(cc1NC1CCCCC1)Sc1cc(NC3CCCCC3)ccc1N2]

In this embodiment:
$R^{1A}$ is —CH[—(CH$_2$)$_5$—] (i.e., cyclohexyl), that is, a substituent attached via a —CH< group);
$R^{1B}$ is —H;
$R^{2A}$ is —CH[—(CH$_2$)$_5$—] (i.e., cyclohexyl), that is, a substituent attached via a —CH< group);
$R^{2B}$ is —H;
and the aldehyde/ketone is cyclohexanone (i.e., (O=)C<, i.e., (O=)C[—(CH$_2$)$_5$—];
or more specifically:
$R^{1A}$ is —CH($R^{1AX}$)($R^{1AY}$), and is —CH[—(CH$_2$)$_5$—];
$R^{1B}$ is —H;
$R^{2A}$ is —CH($R^{2AX}$)($R^{2AY}$), and is —CH[—(CH$_2$)$_5$—]; and
$R^{2B}$ is —H;
and the aldehyde/ketone is cyclohexanone (i.e., (O=)C[—(CH$_2$)$_5$—]):

$R^{1AX}$—C(=O)—$R^{1AY}$, where $R^{1AX}$ and $R^{1AY}$, taken together, form $C_5$alkylene; and
$R^{2AX}$—C(=O)—$R^{2AY}$, where $R^{2AX}$ and $R^{2AY}$, taken together, form $C_5$alkylene.

Similarly, in one embodiment, a compound of the following formula:

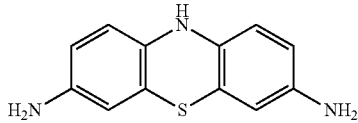

Formula (4a)

is reacted with glutaraldehyde ((O=)CH—(CH$_2$)$_3$—CH (=O)), under reductive amination conditions, to give the corresponding compound of the following formula:

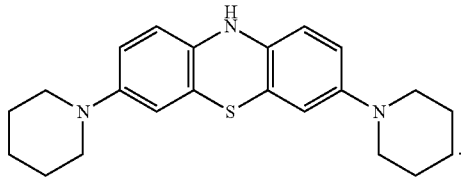 [SMILES: c1cc2c(cc1N1CCCCC1)Sc1cc(N3CCCCC3)ccc1N2]

In this embodiment:
$R^{1A}$ and $R^{1B}$, taken together, form —(CH$_2$)$_5$—, that is, a substituent with two points of attachment, wherein each of the attachments is via a —CH< group; and
$R^{2A}$ and $R^{2B}$, taken together, form —(CH$_2$)$_5$—, that is, a substituent with two points of attachment, wherein each of the attachments is via a —CH< group; the aldehyde/ketone is glutaraldehyde (i.e., (O=)CH—(CH$_2$)$_3$—CH (=O));
or more specifically:
$R^{1A}$ and $R^{1B}$, taken together, form —CH$_2$—$R^{1AB}$—CH$_2$—;
$R^{1AB}$ is —(CH$_2$)$_3$—;
$R^{2A}$ and $R^{2B}$, taken together, form —CH$_2$—$R^{2AB}$—CH$_2$—;
$R^{2AB}$ is —(CH$_2$)$_3$—;
and the aldehyde/ketone is glutaraldehyde (i.e., (O=)CH—(CH$_2$)$_3$—CH(=O)):
(O=)CH—$R^{1AB}$—CH(=O), where $R^{1AB}$ is —(CH$_2$)$_3$—; and
(O=)CH—$R^{2AB}$—CH(=O), where $R^{2AB}$ is —(CH$_2$)$_3$—.

Aldehyde/Ketone: Some Examples

In one embodiment:
if (a):
$R^{1A}$ is —CH($R^{1AX}$)($R^{1AY}$); and
$R^{1B}$ is independently —H or —CH($R^{1BX}$)($R^{1BY}$);
$R^{2A}$ is —CH($R^{2AX}$)($R^{2AY}$); and
$R^{2B}$ is independently —H or —CH($R^{2BX}$)($R^{2BY}$);
then the aldehyde/ketone comprises:
$R^{1AX}$—C(=O)—$R^{1AY}$, and
$R^{2AX}$—C(=O)—$R^{2AY}$;
and further if $R^{1B}$ is other than —H, then the aldehyde/ketone further comprises:
$R^{1BX}$—C(=O)—$R^{1BY}$;
and further if $R^{2B}$ is other than —H, then the aldehyde/ketone further comprises:
$R^{2BX}$—C(=O)—$R^{2BY}$;
and if (b):
$R^{1A}$ and $R^{1B}$, taken together, form —CH$_2$—$R^{1AB}$—CH$_2$—; and $R^{2A}$ and $R^{2B}$, taken together, form —CH$_2$—$R^{2AB}$—CH$_2$—;
then the aldehyde/ketone comprises:
(O=)CH—$R^{1AB}$—CH(=O); and
(O=)CH—$R^{2AB}$—CH(=O).

In one embodiment:
$R^{1AX}$—C(=O)—$R^{1AY}$ is the same as $R^{2AX}$—C(=O)—$R^{2AY}$
(and consequently $R^{1A}$ and $R^{2A}$ are the same).

In one embodiment:
neither $R^{1B}$ nor $R^{2B}$ is —H
(and consequently the aldehyde/ketone further comprises $R^{1BX}$—C(=O)—$R^{1BY}$ and $R^{2BX}$—C(=O)—$R^{2BY}$); and
$R^{1BX}$—C(=O)—$R^{1BY}$ is the same as $R^{2BX}$—C(=O)—$R^{2BY}$
(and consequently $R^{1B}$ and $R^{2B}$ are the same).

"N,N-Disubstituted, Same Substituents" (neither $R^{1B}$ nor $R^{2B}$ is —H):

In one embodiment:
$R^{1AX}$—C(=O)—$R^{1AY}$ is the same as $R^{2AX}$—C(=O)—$R^{2AY}$
(and consequently $R^{1A}$ and $R^{2A}$ are the same);
neither $R^{1B}$ nor $R^{2B}$ is —H
(and consequently the aldehyde/ketone further comprises $R^{1BX}$—C(=O)—$R^{1BY}$ and $R^{2BX}$—C(=O)—$R^{2BY}$);
$R^{1BX}$—C(=O)—$R^{1BY}$ is the same as $R^{2BX}$—C(=O)—$R^{2BY}$
(and consequently $R^{1B}$ and $R^{2B}$ are the same); and
$R^{1AX}$—C(=O)—$R^{1AY}$ is the same as $R^{1BX}$—C(=O)—$R^{1BY}$
(and consequently $R^{1A}$ and $R^{2A}$ and $R^{1B}$ and $R^{2B}$ are all the same).

In an example of such an embodiment:
$R^{1AX}$—C(=O)—$R^{1AY}$ and $R^{2AX}$—C(=O)—$R^{2AY}$ are H—C(=O)—H (i.e., formaldehyde);
$R^{1BX}$—C(=O)—$R^{1BY}$ and $R^{2BX}$—C(=O)—$R^{2BY}$ are H—C(=O)—H (i.e., formaldehyde);
$R^{1A}$ and $R^{2A}$ are -Me; and
$R^{1B}$ and $R^{2B}$ are -Me.

"N,N-Disubstituted, Different Substituents" (neither $R^{1B}$ nor $R^{2B}$ is —H):

In one embodiment:
$R^{1AX}$—C(=O)—$R^{1AY}$ is the same as $R^{2AX}$—C(=O)—$R^{2AY}$
(and consequently $R^{1A}$ and $R^{2A}$ are the same);
neither $R^{1B}$ nor $R^{2B}$ is —H
(and consequently the aldehyde/ketone further comprises $R^{1BX}$—C(=O)—$R^{1BY}$ and $R^{2BX}$—C(=O)—$R^{2BY}$);
$R^{1BX}$—C(=O)—$R^{1BY}$ is the same as $R^{2BX}$—C(=O)—$R^{2BY}$
(and consequently $R^{1B}$ and $R^{2B}$ are the same); but
$R^{1AX}$—C(=O)—$R^{1AY}$ is different from $R^{1BX}$—C(=O)—$R^{1BY}$
(and consequently $R^{1A}$ and $R^{1B}$ are different).

In an example of such an embodiment:
$R^{1AX}$—C(=O)—$R^{1AY}$ and $R^{2AX}$—C(=O)—$R^{2AY}$ are CH$_3$—C(=O)—CH$_3$ (i.e., acetone);
$R^{1BX}$—C(=O)—$R^{1BY}$ and $R^{2BX}$—C(=O)—$R^{2BY}$ are H—C(=O)—H (i.e., formaldehyde);
$R^{1A}$ and $R^{2A}$ are -iPr (i.e., —CH(CH$_3$)(CH$_3$)); and
$R^{1B}$ and $R^{2B}$ are -Me.

"N-Monosubstituted" ($R^{1B}$ and $R^{2B}$ are both —H):

In one embodiment:
$R^{1AX}$—C(=O)—$R^{1AY}$ is the same as $R^{2AX}$—C(=O)—$R^{2AY}$
(and consequently $R^{1A}$ and $R^{2A}$ are the same); and
both $R^{1B}$ and $R^{2B}$ is —H
(and consequently the aldehyde/ketone does not further comprise
$R^{1BX}$—C(=O)—$R^{1BY}$ and $R^{2BX}$—C(=O)—$R^{2BY}$).

In an example of such an embodiment:
$R^{1AX}$—C(=O)—$R^{1AY}$ and $R^{2AX}$—C(=O)—$R^{2AY}$ are $CH_3$—C(=O)—$CH_3$ (i.e., acetone);
$R^{1BX}$—C(=O)—$R^{1BY}$ and $R^{2BX}$—C(=O)—$R^{2BY}$ are absent;
$R^{1A}$ and $R^{2A}$ are -iPr (i.e., —CH(CH$_3$)$_2$); and
$R^{1B}$ and $R^{2B}$ are —H.

Examples of suitable aldehydes and ketones are shown in the following tables.

TABLE 3

Examples of Suitable Aldehydes (*)

| Aldehyde | Formula, (O=)C< (O=)C(H)(R$^P$) | Resulting Group, —CH< —CH(H)(R$^P$) |
|---|---|---|
| Formaldehyde (methanal) | (O=)CH—H | —CH$_3$ |
| Acetaldehyde (ethanal) | (O=)CH—CH$_3$ | —CH$_2$CH$_3$ |
| Propionaldehyde (propanal) | (O=)CH—CH$_2$CH$_3$ | —CH$_2$CH$_2$CH$_3$ |
| Butyraldehyde (butanal) | (O=)CH—CH$_2$CH$_2$CH$_3$ | —CH$_2$CH$_2$CH$_2$CH$_3$ |
| Benzaldehyde (phenylmethanal) | (O=)CH-phenyl | —CH$_2$-phenyl |

(*) In monomeric or polymeric form, as discussed herein.

TABLE 4

Examples of Suitable Ketones

| Ketone | Formula, (O=)C < R$^P$—C(=O)—R$^Q$ | Resulting Group, —CH < —CH(R$^P$)(R$^Q$) |
|---|---|---|
| Acetone | CH$_3$—C(=O)—CH$_3$ | —CH(CH$_3$)$_2$ |
| Butan-2-one | CH$_3$—CH$_2$—C(=O)—CH$_3$ | —CH(CH$_3$)(CH$_2$CH$_3$) |
| Acetophenone | CH$_3$—C(=O)—phenyl | —CH(CH$_3$)(phenyl) |
| Cyclopentanone | (O=)C[—(CH$_2$)$_4$—] | cyclopentyl |
| Cyclohexanone | (O=)C[—(CH$_2$)$_5$—] | cyclohexyl |

TABLE 5

Examples of Suitable Dialdehydes(*)

| Aldehyde | Formula (O=)CH—R$^{PQ}$—CH(=O) | Resulting Group —CH$_2$—(—R$^{PQ}$—)—CH$_2$— |
|---|---|---|
| Succinaldehyde | (O=)CH—(CH$_2$)$_2$—CH(=O) | —(CH$_2$)$_4$— (giving pyrrolidino) |
| Glutaraldehyde | (O=)CH—(CH$_2$)$_3$—CH(=O) | —(CH$_2$)$_5$— (giving piperidino) |
| Adipaldehyde | (O=)CH—(CH$_2$)$_4$—CH(=O) | —(CH$_2$)$_6$— (giving azepano) |

(*)In monomeric or polymeric form, as discussed herein.

A range of different combinations of $R^{1A}$, $R^{1B}$, $R^{2A}$ and $R^{2B}$ can be obtained by using the corresponding aldehyde(s) and/or ketone(s). Examples of some suitable combinations are listed in the following table.

TABLE 6

Examples of Some Combinations of Aldehyde(s) (*) and/or Ketone(s)

| $R^{1A}$ $R^{2A}$ | $R^{1B}$ $R^{2B}$ | $R^{1AX}$—C(=O)—$R^{1AY}$ $R^{2AX}$—C(=O)—$R^{2AY}$ | $R^{1BX}$—C(=O)—$R^{1BY}$ $R^{2BX}$—C(=O)—$R^{2BY}$ |
|---|---|---|---|
| —Me | —Me | formaldehyde | formaldehyde |
| —Et | —Et | acetaldehyde | acetaldehyde |
| —nPr | —nPr | propionaldehyde | propionaldehyde |
| —nBu | —nBu | butyraldehyde | butyraldehyde |
| —iPr | —H | acetone | (none) |
| —iPr | —Me | acetone | formaldehyde |
| —iPr | —Et | acetone | acetaldehyde |
| —iPr | —nPr | acetone | propionaldehyde |
| —iPr | —nBu | acetone | butyraldehyde |
| —iBu | —H | butan-2-one | (none) |
| —iBu | —Me | butan-2-one | formaldehyde |
| —iBu | —Et | butan-2-one | acetaldehyde |
| —iBu | —nPr | butan-2-one | propionaldehyde |
| —iBu | —nBu | butan-2-one | butyraldehyde |
| cyclopentyl | —H | cyclopentanone | (none) |
| cyclohexyl | —H | cyclohexanone | (none) |

(*)In monomeric or polymeric form, as discussed herein.

Selective Alkylation by Reductive Amination: Reaction Conditions

Again, the methods of synthesis proceed via a step of selective alkylation by reductive amination, in which a compound of Formula (4):

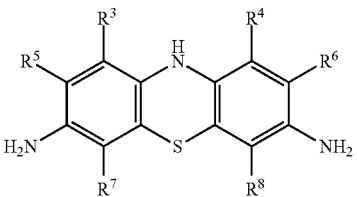

Formula (4)

is reacted with a desired aldehyde/ketone and a reductive amination agent, under reductive amination conditions, to give the corresponding compound of Formula (1):

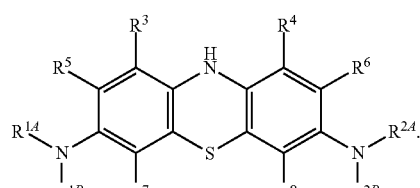

Formula (1)

The amount of aldehyde/ketone depends upon the degree of alkylation sought and whether or not a particular aldehyde or ketone is a mono-aldehyde/ketone or di-aldehyde/ketone. In principle, one equivalent of aldehyde/ketone (more specifically, one equivalent of aldehyde/ketone group) is required for each nitrogen substituent (i.e., for each of $R^{1A}$, $R^{1B}R^{2A}$, and $R^{2B}$, when other than hydrogen).

For example, when each of $R^{1A}$, $R^{1B}$, $R^{2A}$, and $R^{2B}$ is -Me (from formaldehyde), then about 4 equivalents of formaldehyde is required (e.g., provided as formaldehyde, paraformaldehyde, etc.).

Similarly, when $R^{1A}$ and $R^{2A}$ are -iPr (from acetone) and $R^{1B}$ and $R^{2B}$ are —H, then about 2 equivalents of acetone are required.

Similarly, when $R^{1A}$ and $R^{1B}$, taken together, form —$(CH_2)_5$— (from the di-aldehyde glutaraldehyde, and $R^{2A}$ and $R^{2B}$, taken together, form —$(CH_2)_5$— (from the di-aldehyde glutaraldehyde, then about 2 equivalents of glutaraldehyde are required.

An example of a suitable reductive amination agent is hydrogen, for example, gaseous hydrogen.

Typically, a suitable feedstock of gaseous hydrogen is supplied. Any suitable pressure may be used, for example, from about 1 to about 20 bar, for example, from about 1 to about 6 bar, for example, from about 2 to about 4 bar.

Corresponding suitable reductive amination conditions may, for example, include the presence of a suitable hydrogenation catalyst.

Typically, the catalyst is present in a catalytic amount, e.g., less than about 0.1 equivalents, e.g., from about 0.00001 to about 0.1 equivalents, e.g., from about 0.0001 to about 0.05 equivalents. For example, in the worked examples shown below, approximately 0.013 equivalents was used.

The hydrogenation catalyst may be a homogenous or heterogeneous catalyst. Examples of suitable heterogeneous catalysts include heterogeneous palladium, platinum, ruthenium, and nickel catalysts. Examples of suitable homogenous catalysts include iron, ruthenium, osmium, rhodium, iridium, and nickel catalysts.

For example, a suitable heterogeneous catalyst is a palladium-based hydrogenation catalyst, for example, "palladium on carbon" (usually denoted Pd(C)), for example, 5% (w/w) Pd(C).

A corresponding example of suitable reductive amination conditions is a relatively high pressure of hydrogen gas, in the presence of a suitable hydrogenation catalyst, for example, a palladium-based hydrogenation catalyst, for example, "palladium on carbon" (usually denoted Pd(C)), for example, 5% (w/w) Pd(C).

Any suitable reaction temperature may be used. The temperature may be, for example, from about 20° C. to about 100° C. (or reflux temperature), from example, about 90° C.

Any suitable reaction time may be used, in accordance with the other reaction conditions. The reaction time may be, for example, from about 30 minutes to about 1 week, for example, from about 1 hour to about 96 hours, for example, from about 2 hour to about 48 hours.

For example, a compound of Formula (4), a catalytic amount of Pd(C) catalyst, the required aldehyde/ketone (for example, paraformaldehyde), and a suitable solvent (for example, N,N-dimethylformamide) are added to a suitable pressure vessel, and the vessel pressurized with gaseous hydrogen to a suitable pressure, for example, about 4 bar. The reaction mixture may then be stirred, for example, at about 90° C., for example, for about 2 to 48 hours. The vessel is then vented, and the solution filtered to remove the catalyst, to give the product in solution in the filtrate. If desired, the product can then be precipitated, filtered, dried, and purified. Alternatively, the solution can be used for subsequent reaction.

Worked examples of similar methods are shown below.

Another example of a suitable reductive amination agent is a hydride, for example, sodium cyanoborohydride, sodium triacetoxyborohydride, and sodium borohydride.

For example, the compound of Formula (4), a hydride, the required aldehyde/ketone, a suitable solvent (for example, N,N-dimethylformamide) and a carboxylic acid (for example, acetic acid) are added to a suitable vessel. The mixture may be stirred, for example, at 40° C., for example, for about 2 to 24 hours. If desired, the product can then be precipitated, filtered, dried, and purified. Alternatively, the solution can be used for subsequent reaction.

Another example of a suitable reductive amination agent is a transfer hydrogenation reagent, for example, decaborane.

Corresponding suitable reductive amination conditions may, for example, include the presence of a suitable hydrogenation catalyst.

Typically, the catalyst is present in a catalytic amount, e.g., less than about 0.1 equivalents, e.g., from about 0.00001 to about 0.1 equivalents, e.g., from about 0.0001 to about 0.05 equivalents. For example, in the worked examples shown below, approximately 0.013 equivalents was used.

The hydrogenation catalyst may be a homogenous or heterogeneous catalyst. Examples of suitable heterogeneous catalysts include heterogeneous palladium, platinum, ruthenium, and nickel catalysts. Examples of suitable homogenous catalysts include iron, ruthenium, osmium, rhodium, iridium, and nickel catalysts.

For example, a suitable heterogeneous catalyst is a palladium-based hydrogenation catalyst, for example, "palladium on carbon" (usually denoted Pd(C)), for example, 5% (w/w) Pd(C).

Any suitable reaction temperature may be used. The temperature may be, for example, from about 20° C. to about 100° C. (or reflux temperature), from example, about 90° C. It may be that the reaction is carried out at more than one temperature, for example, by reflux for an initial period followed by room temperature for a second period. It may be that the reflux period reduces an oxidised compound of Formula (7) to the corresponding compound of Formula (4).

Any suitable reaction time may be used, in accordance with the other reaction conditions. The reaction time may be, for example, from about 30 minutes to about 1 week, for example, from about 1 hour to about 96 hours, for example, from about 2 hours to about 48 hours. For example, a compound of Formula (4), a catalytic amount of Pd(C) catalyst, the required aldehyde/ketone (for example, acetone), a transfer hydrogenation agent (for example, decaborane) a suitable solvent (for example, methanol) and optionally an acid (for example, glacial acetic acid) are added to a suitable vessel. The reaction mixture may then be stirred and heated, for example, at about 90° C., for example, for about 30 minutes to 2 hours. The reaction may be cooled, for example to 25° C., and left to stir, for example for about 1 to 10 hours. The solution may then be filtered (for example, filtered through Celite) to remove the catalyst, to give the product in solution in the filtrate. If desired, the product can then be isolated, for example by precipitation, filtration, trituration or evaporation of solvent. Alternatively, the solution can be used for subsequent reaction.

It may be that the reaction is carried out in a single step starting from a compound of Formula (7) which is reduced under the reaction conditions to a compound of Formula (4). The compound of Formula (4) formed in situ then undergoes the reductive amination to provide the compound of Formula (1). It may be that the reflux period or heating period reduces the compound of Formula (7).

Worked examples of similar methods are shown below. Similar methods are described, for example, in Jung et al., 2003, Tetrahedron, Vol. 59, pp. 10331-10338.

Preceding Steps: Formation of Unsubstituted Diamine Compound

The methods of synthesis may include preceding steps for the formation of the corresponding unsubstituted diamine compound.

In one embodiment, in a step of nitro reduction, a compound of Formula (5):

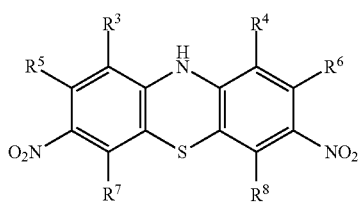

Formula (5)

is reacted with a nitro reducing agent, under nitro reducing conditions, to give the corresponding compound of Formula (4):

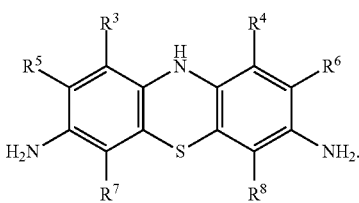

Formula (4)

An example of a suitable nitro reducing agent is hydrogen, for example, gaseous hydrogen.

Typically, a suitable feedstock of gaseous hydrogen is supplied. Any suitable pressure may be used, for example, from about 1 to about 20 bar, for example, from about 1 to about 6 bar, for example, from about 2 to about 4 bar.

Corresponding suitable nitro reducing conditions may, for example, include the presence of a suitable hydrogenation catalyst.

Typically, the catalyst is present in a catalytic amount, e.g., less than about 0.1 equivalents, e.g., from about 0.00001 to about 0.1 equivalents, e.g., from about 0.0001 to about 0.05 equivalents. For example, in the worked examples shown below, approximately 0.013 equivalents was used.

The hydrogenation catalyst may be a homogenous or heterogeneous catalyst. Examples of suitable heterogeneous catalysts include heterogeneous palladium, platinum, ruthenium, and nickel catalysts. Examples of suitable homogenous catalysts include iron, ruthenium, osmium, rhodium, iridium, and nickel catalysts.

For example, a suitable heterogeneous catalyst is a palladium-based hydrogenation catalyst, for example, "palladium on carbon" (usually denoted Pd(C)), for example, 5% (w/w) Pd(C).

A corresponding example of suitable nitro reducing conditions is a relatively high pressure of hydrogen gas, in the presence of a suitable hydrogenation catalyst, for example, a palladium-based hydrogenation catalyst, for example, "palladium on carbon" (usually denoted Pd(C)), for example, 5% (w/w) Pd(C).

Any suitable reaction temperature may be used. The temperature may be, for example, from about 20° C. to about 100° C. (or reflux temperature), for example, about 90° C.

Any suitable reaction time may be used, in accordance with the other reaction conditions. The reaction time may be, for example, from about 5 minutes to about 1 day, for example, from about 5 minutes to about 6 hours, for example, from about 10 minutes to about 120 minutes.

For example, the compound of Formula (5), a catalytic amount of Pd(C) catalyst, and a suitable solvent (for example, N,N-dimethylformamide) may be added to a suitable pressure vessel, and the vessel pressurized with gaseous hydrogen to a suitable pressure, for example, about 4 bar. The reaction mixture may then be stirred, for example, at ambient temperature, for example, for about 10 to about 120 minutes. The vessel may then be vented, and the product collected and purified if desired.

A worked example of a similar method is shown below.

If desired, the step of nitro reduction and the step of selective alkylation by reductive amination may be performed in sequence, without intervening steps of isolating and/or purifying the unsubstituted amine (e.g., in a "one pot" process).

In one embodiment, in a further preceding step of nitration, a compound of Formula (6):

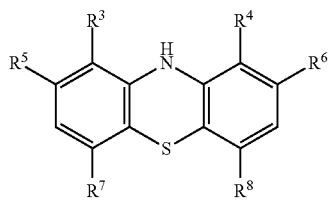

Formula (6)

is reacted with a nitration agent, under nitration conditions, to give the corresponding compound of Formula (5):

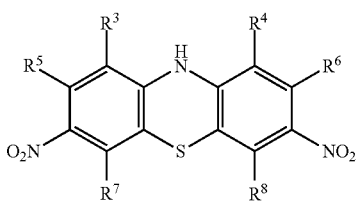

Formula (5)

An example of a suitable nitration agent is sodium nitrite (NaNO$_2$).

Typically, the nitration agent is present in large excess, e.g., more than about 5 equivalents, e.g., from about 5 to about 10 equivalents, e.g., from about 6 to about 6.5 equivalents.

Corresponding suitable nitration conditions may, for example, include the presence of an acid, such as acetic acid.

Typically, the acid is present in large excess, e.g., more than about 5 equivalents, e.g., from about 5 to about 30 equivalents, e.g., from about 10 to about 20 equivalents.

The reaction may be carried out in a suitable solvent, which may be a mixture of solvents. Examples of suitable solvents include, for example, acetonitrile, dimethylsulfoxide, tetrahydrofuran, N,N-dimethylformamide, acetone, methyl tert-butyl ether, and sulfolane, which may be used alone or in combination.

Any suitable reaction temperature may be used. The temperature may be, for example, from about 20° C. to about 100° C. (or reflux temperature), for example, ambient temperature.

Any suitable reaction time may be used, in accordance with the other reaction conditions. The reaction time may be, for example, from about 30 minutes to about 2 days, for example, from about 1 hour to about 24 hours.

For example, the compound of Formula (6), an excess of $NaNO_2$ (for example, about 5 to 10 equivalents, for example, about 6 to 6.5 equivalents) and solvent may be combined in a suitable vessel, and an excess of acetic acid (for example, about 5 to 30 equivalents, for example, about 10 to 20 equivalents) added (for example, dropwise, for example, over about an hour). The reaction mixture may then be stirred, for example, at ambient temperature, for example, for about 1 to 24 hours. The reaction mixture may then be stirred, for example, at about reflux temperature, for example, for about 1 to 24 hours. The reaction mixture may then be cooled, and the product collected by filtration.

A worked example of a similar method is shown below.

Similar methods are described, for example, in Tomilin et al., 1996 and Fiedelei, 1994.

Preceding Steps: Formation of Unsubstituted Diamine Compound

Alternatively, the unsubstituted diamine compound may be prepared by reducing the corresponding oxidized compound.

In one embodiment, in a step of thionine reduction, a compound of Formula (7):

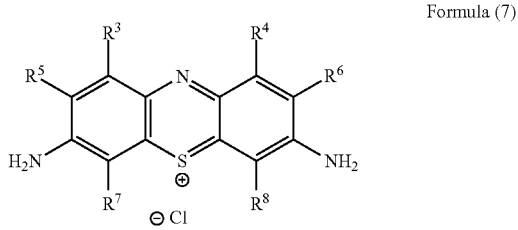

Formula (7)

is reacted with a thionine reducing agent, under thionine reducing conditions, to give the corresponding compound of Formula (4):

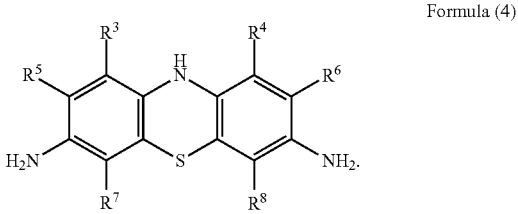

Formula (4)

An example of a suitable thionine reducing agent is hydrogen, for example, gaseous hydrogen.

Typically, a suitable feedstock of gaseous hydrogen is supplied. Any suitable pressure may be used, for example, from about 1 to about 20 bar, for example, from about 1 to about 6 bar, for example, from about 2 to about 4 bar.

Corresponding suitable thionine reducing conditions may, for example, include the presence of a suitable hydrogenation catalyst.

Typically, the catalyst is present in a catalytic amount, e.g., less than about 0.1 equivalents, e.g., from about 0.00001 to about 0.1 equivalents, e.g., from about 0.0001 to about 0.05 equivalents. For example, in the worked examples shown below, approximately 0.013 equivalents was used.

The hydrogenation catalyst may be a homogenous or heterogeneous catalyst. Examples of suitable heterogeneous catalysts include heterogeneous palladium, platinum, ruthenium, and nickel catalysts. Examples of suitable homogenous catalysts include iron, ruthenium, osmium, rhodium, iridium, and nickel catalysts.

For example, a suitable heterogeneous catalyst is a palladium-based hydrogenation catalyst, for example, "palladium on carbon" (usually denoted Pd(C)), for example, 5% (w/w) Pd(C).

A corresponding example of suitable thionine reducing conditions is a relatively high pressure of hydrogen gas, in the presence of a suitable hydrogenation catalyst, for example, a palladium-based hydrogenation catalyst, for example, "palladium on carbon" (usually denoted Pd(C)), for example, 5% (w/w) Pd(C).

Any suitable reaction temperature may be used. The temperature may be, for example, from about 20° C. to about 100° C. (or reflux temperature), for example, ambient temperature.

Any suitable reaction time may be used, in accordance with the other reaction conditions. The reaction time may be, for example, from about 5 minutes to about 1 day, for example, from about 5 minutes to about 6 hours, for example, from about 10 minutes to about 120 minutes.

For example, the compound of Formula (7), a catalytic amount of Pd(C) catalyst, and a suitable solvent (for example, N,N-dimethylformamide) may be added to a suitable pressure vessel, and the vessel pressurized with gaseous hydrogen to a suitable pressure, for example, about 4 bar. The reaction mixture may then be stirred, for example, at ambient temperature, for example, for about 10 to 120 minutes. The vessel may then be vented, and the product collected and purified if desired.

Similar methods are described, for example, in Wildes et al., 1978 and Epstein et al., 1941.

Another example of a suitable thionine reducing agent is a transfer hydrogenation reagent, for example, decaborane.

Corresponding suitable thionine reducing conditions may, for example, include the presence of a suitable hydrogenation catalyst.

Typically, the catalyst is present in a catalytic amount, e.g., less than about 0.1 equivalents, e.g., from about 0.00001 to about 0.1 equivalents, e.g., from about 0.0001 to about 0.05 equivalents. For example, in the worked examples shown below, approximately 0.013 equivalents was used.

The hydrogenation catalyst may be a homogenous or heterogeneous catalyst. Examples of suitable heterogeneous catalysts include heterogeneous palladium, platinum, ruthenium, and nickel catalysts. Examples of suitable homogenous catalysts include iron, ruthenium, osmium, rhodium, iridium, and nickel catalysts.

For example, a suitable heterogeneous catalyst is a palladium-based hydrogenation catalyst, for example, "palladium on carbon" (usually denoted Pd(C)), for example, 5% (w/w) Pd(C).

Any suitable reaction temperature may be used. The temperature may be, for example, from about 20° C. to about 100° C. (or reflux temperature), from example, about 90° C. It may be that the reaction is carried out at more than one temperature, for example, by reflux for an initial period followed by room temperature for a second period.

Any suitable reaction time may be used, in accordance with the other reaction conditions. The reaction time may be, for example, from about 30 minutes to about 1 week, for example, from about 1 hour to about 96 hours, for example, from about 2 hours to about 48 hours.

For example, a compound of Formula (7), a catalytic amount of Pd(C) catalyst, a transfer hydrogenation agent (for example, decaborane) a suitable solvent (for example, methanol) and optionally an acid (for example, glacial acetic acid) are added to a suitable vessel. The reaction mixture may then be stirred and heated, for example, at about 90° C., for example, for about 30 minutes to 2 hours. The solution may then be filtered (for example, filtered through Celite) to remove the catalyst, to give the product in solution in the filtrate. If desired, the product can then be isolated, for example by precipitation, filtration, trituration or evaporation of solvent. Alternatively, the solution can be used for subsequent reaction.

Similar methods are described, for example, in Jung et al., 2003, Tetrahedron, Vol. 59, pp. 10331-10338.

If desired, the step of thionine reduction and the step of selective alkylation by reductive amination may be performed in sequence, without intervening steps of isolating and/or purifiying the unsubstituted amine (e.g., in a "one pot" process).

It may be that a reaction is carried out in a single step to produce a compound of Formula (1) from a compound of Formula (7). The compound of Formula (7) may be reduced under thioinin reducing conditions to a compound of Formula (4). The compound of Formula (4) formed in situ then undergoes the reductive amination to provide the compound of Formula (1). It may be that the reducing agents for the reductive amination and the thionine reduction are the same, for example, both reactions may use a transfer hydrogenation reagent (e.g. decaborane) in the presence of a suitable hydrogenation catalyst (e.g. palladium on carbon).

It may be that a reflux period or heating period is used to reduce the compound of Formula (7).

For example, a compound of Formula (7), a catalytic amount of Pd(C) catalyst, the required aldehyde/ketone (for example, acetone), a transfer hydrogenation agent (for example, decaborane) a suitable solvent (for example, methanol) and optionally an acid (for example, glacial acetic acid) are added to a suitable vessel. The reaction mixture may then be stirred and heated, for example, at about 90° C., for example, for about 30 minutes to 2 hours. This heating step may be used to reduce the compound of Formula (7) to the corresponding compound of Formula (4). The reaction may be cooled, for example to 25° C., and left to stir, for example for about 1 to 10 hours. The solution may then be filtered (for example, filtered through Celite) to remove the catalyst, to give the product of Formula (1) in solution in the filtrate. If desired, the product can then be isolated, for example by precipitation, filtration, trituration or evaporation of solvent. Alternatively, the solution can be used for subsequent reaction.

The term 'thionine' is sometimes written as 'thionin'. For example, in Examples 8 to 12 below 'thionin acetate' is used as a starting material. 'Thionin acetate' is 'thionine acetate'; the spelling used in the Examples reflects the spelling on the label of the starting material used.

In one embodiment, in a further preceding step of ring formation, compounds of Formula (8) and Formula (9):

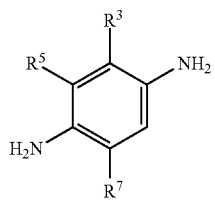

Formula (8)

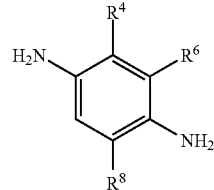

Formula (9)

are reacted with an oxidizing agent and a sulfide, under ring forming conditions, to give the corresponding compound of Formula (7):

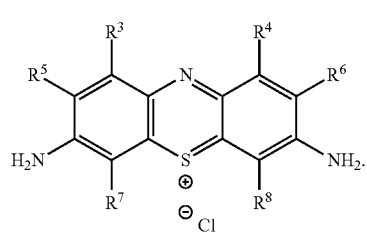

Formula (7)

An example of a suitable oxidizing agent is Fe(III) chloride ($FeCl_3$), typically provided as the hexahydrate, $FeCl_3.6H_2O$.

Typically, the oxidizing agent is present in large excess, e.g., more than about 6 equivalents, e.g., from about 6 to about 10 equivalents, e.g., from about 6.6 to about 8.0 equivalents.

Examples of a suitable sulfide include $H_2S$ or $Na_2S$.

Typically, the sulfide is present in excess, e.g., more than about 1 equivalent, e.g., from about 1 to about 10 equivalents.

Corresponding suitable oxidizing conditions may, for example, include the presence of an acid, e.g., aqueous strong acid, e.g., aqueous hydrochloric acid.

Typically, the acid is present in excess, e.g., more than about 50 equivalents, e.g., from about 50 to about 60 equivalents, e.g., about 54 equivalents.

Any suitable reaction temperature may be used. The temperature may be, for example, from about 2° C. to about 15° C., for example, about 5° C.

Any suitable reaction time may be used, in accordance with the other reaction conditions. The reaction time may be, for example, from about 60 minutes to about 5 hours, for example, from about 1 hours to about 2 hours.

Similar methods are described, for example, in Michaelis et al., 1940.

Subsequent Steps: Conversion to Di-Salt

The methods of synthesis may include a subsequent step of di-salt formation, in which a compound of Formula (1):

Formula (1)

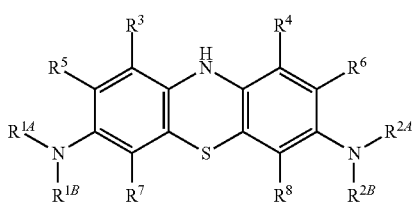

is dissolved in solvent and reacted with the desired acid, under salt forming conditions, to give the corresponding compound of Formula (2):

Formula (2)

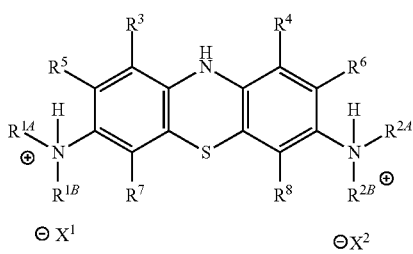

Typically, the acid is present in excess, e.g., more than about 2.0 equivalents, e.g., from about 2.0 to about 3.0 equivalents, e.g., about 2.2 equivalents.

Any suitable solvent may be used, for example toluene, methanol, or a mixture thereof.

Suitable salt forming conditions may, for example, include cooling the reaction mixture (to cause precipitation), optionally with the addition of an anti-solvent.

Any suitable cooling temperature may be used. For example, the cooling may be to a temperature below ambient temperature, for example, a temperature less than about 15° C., for example, a temperature less than about 10° C., for example, a temperature of about 5° C.

Any suitable anti-solvent may be used, for example, ethanol, ethyl acetate, methyl acetate, or a mixture thereof.

For example, the compound of Formula (1), a small excess (for example, 2.2 equivalents) of the required acid (e.g., methanesulfonic acid), and suitable solvent (for example, a mixture of methanol and toluene) are combined and cooled, for example, to 5° C. A suitable anti-solvent (e.g., ethanol) may be added to promote precipitation. The precipitated product may then be collected, for example, by filtration, and washed, dried, and purified (e.g., by recrystallization), if desired.

A worked example of a similar method is shown below.

Similar methods are described, for example, in Marshall et al., 2012.

Subsequent Steps: Conversion to Oxidized Form

Alternatively, the methods of synthesis may include a subsequent step of thiazine oxidation, in which a compound of Formula (1):

Formula (1)

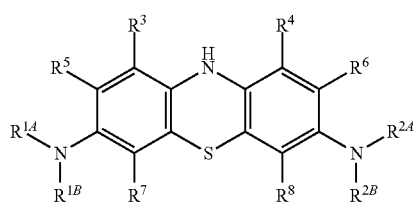

is reacted with an oxidizing agent and an acid, under oxidizing conditions, to give the corresponding compound of Formula (3):

Formula (3)

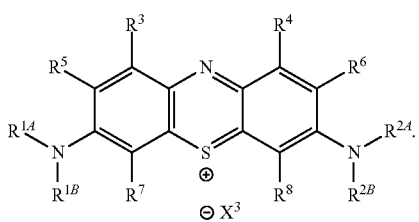

An example of a suitable oxidizing agent is Fe(III) chloride ($FeCl_3$), typically provided as the hexahydrate, $FeCl_3.6H_2O$.

Typically, the oxidizing agent is present in excess, e.g., more than about 2.0 equivalents, e.g., from about 2.0 to about 10 equivalents, e.g., from about 2.0 to about 3 equivalents, e.g., about 2.1 equivalents.

An example of a suitable acid is a strong aqueous strong acid, for example, aqueous hydrochloric acid.

Typically, the acid is present in excess, e.g., more than about 2.0 equivalents, e.g., from about 2.0 to about 3.0 equivalents, e.g., about 2.2 equivalents.

Any suitable reaction temperature may be used. The temperature may be, for example, from about 1° C. to about 15° C., from example, about 5° C.

Any suitable reaction time may be used, in accordance with the other reaction conditions. The reaction time may be, for example, from about 5 minutes to about 2 days, for example, from about 1 hours to about 3 hours.

For example, the compound of Formula (1) and an excess (for example, 2.2 equivalents) of the required acid (e.g., hydrochloric acid) is added to a suitable solvent (for example, N,N-dimethylformamide) and cooled, for example, to 5° C. A slight excess of two equivalents (for example, 2.1 equivalents) of iron (III) chloride is added (for example, as an aqueous solution of $FeCl_3.6H_2O$), for example, dropwise, for example, over about 30 minutes. After the addition, the reaction mixture is then stirred, for example, for about 1 to 12 hours, for example, at 5° C. The precipitated product may then be collected, for example, by filtration, and washed, dried, and purified (e.g., by recrystallization), if desired.

A worked example of a similar method is shown below.

Similar methods are described, for example, in Wischik et al., 2008.

Combinations

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the chemical groups represented by variables (e.g., $R^{1A}$, $R^{1A1}$, $R^{1A2}$, $R^{1B}$, $R^{1B1}$, $R^{1B2}$, $R^{1AB}$, $R^{2A}$, $R^{2A1}$, $R^{2A2}$, $R^{2B}$, $R^{2B1}$, $R^{2B2}$, $R^{2AB}$, $R^3$, $R^4$, $R^5$, $R^6$, $R^7$, $R^8$, $X^{1(-)}$, $X^{2(-)}$, $X^{3(-)}$, $R^{X1}$, $R^{X2}$, $R^{X3}$, $R^Y$, etc.) are specifically embraced by the present invention and are disclosed herein just as if each and every combination was individually and explicitly disclosed, to the extent that such combinations embrace compounds that are stable compounds (i.e., compounds that can be isolated, characterised, and tested). In addition, all sub-combinations of the chemical groups listed in the embodiments describing such variables are also specifically embraced by the present invention and are disclosed herein just as if each and every such sub-combination of chemical groups was individually and explicitly disclosed herein.

Chemical Synthesis

Methods for the chemical synthesis of compounds of the present invention are described herein. These methods may be modified and/or adapted in known ways in order to facilitate the synthesis of additional compounds within the scope of the present invention.

Descriptions of general laboratory methods and procedures, useful in the methods of synthesis described herein, are provided in *Vogel's Textbook of Practical Organic Chemistry, 5th Edition*, 1989, (Editors: Furniss, Hannaford, Smith, and Tatchell) (published by Longmann, UK).

Compositions

One aspect of the present invention pertains to a composition (e.g., a pharmaceutical composition) comprising a compound of Formula (1), Formula (2), or Formula (3), as described herein, and a pharmaceutically acceptable carrier, diluent, or excipient.

Another aspect of the present invention pertains to a method of preparing a composition (e.g., a pharmaceutical composition) comprising mixing a compound of Formula (1), Formula (2), or Formula (3), as described herein, and a pharmaceutically acceptable carrier, diluent, or excipient.

Uses

The compounds of Formula (1), Formula (2), and Formula (3), as described herein, are useful in medicine (e.g., therapy), for example, in treatment or prophylaxis.

Use in Methods of Therapy

One aspect of the present invention pertains to a compound of Formula (1), Formula (2), or Formula (3), as described herein, for use in medicine, for example, for use in treatment or prophylaxis, for example, for use in treatment or prophylaxis of a disorder (e.g., a disease), as described herein.

Use in the Manufacture of Medicaments

One aspect of the present invention pertains to use of a compound of Formula (1), Formula (2), or Formula (3), as described herein, in the manufacture of a medicament, for example, for use in a method of treatment or prophylaxis, for example, for use in a method of treatment or prophylaxis of a disorder (e.g., a disease), as described herein.

In one embodiment, the medicament comprises the compound of Formula (1), Formula (2), or Formula (3).

Methods of Treatment

One aspect of the present invention pertains to a method of treatment or prophylaxis, for example, a method of treatment or prophylaxis of a disorder (e.g., a disease), as described herein, comprising administering to a subject in need of treatment a therapeutically-effective amount of a compound of Formula (1), Formula (2), or Formula (3), as described herein, preferably in the form of a pharmaceutical composition.

Disorders Treated

In one embodiment, the disorder is a disease of protein aggregation.

In one embodiment, the disorder is a tauopathy.

In one embodiment, the disorder is Alzheimer's disease (AD), Pick's disease, progressive supranuclear palsy (PSP), frontotemporal dementia (FTD), FTD with parkinsonism linked to chromosome 17 (FTDP 17), frontotemporal lobar degeneration (FTLD) syndromes; disinhibition-dementia-parkinsonism-amyotrophy complex (DDPAC), pallido-ponto-nigral degeneration (PPND), amyotropic lateral sclerosis (ALS), Guam-ALS syndrome, pallido nigro luysian degeneration (PNLD), cortico-basal degeneration (CBD), dementia with argyrophilic grains (AgD), dementia pugilistica (DP) or chronic traumatic encephalopathy (CTE), Down's syndrome (DS), dementia with Lewy bodies (DLB), subacute sclerosing panencephalitis (SSPE), mild cognitive impairment (MCI), Niemann-Pick disease, type C (NPC), Sanfilippo syndrome type B (or mucopolysaccharidosis III B (MPS III B)), myotonic dystrophies (DM), DM1 or DM2, or Huntington's disease (HD).

In one embodiment, the disorder is Alzheimer's disease.
In one embodiment, the disorder is Parkinson's disease.
In one embodiment, the disorder is PSP, ALS, or FTLD.
In one embodiment, the disorder is Huntington's disease.
In one embodiment, the disorder is Huntington's disease or another polyglutamine disorder, such as spinal bulbar muscular atrophy (Kennedy disease), dentatorubropallidoluysian atrophy, or spinocerebellar ataxias.

In one embodiment, the disorder is mild cognitive impairment (MCI).

In one embodiment, the disorder is skin cancer.
In one embodiment, the disorder is melanoma.
In one embodiment, the disorder is a bacterial, viral, or protozoal disease condition.

In one embodiment, the disorder is a viral disease condition.

In one embodiment, the disorder is Hepatitis C, HIV, or West Nile Virus (WNV) infection.

In one embodiment, the disorder is a protozoan disease.
In one embodiment, the disorder is malaria.

Treatment

The term "treatment," as used herein in the context of treating a disorder, pertains generally to treatment of a human or an animal (e.g., in veterinary applications), in which some desired therapeutic effect is achieved, for example, the inhibition of the progress of the disorder, and includes a reduction in the rate of progress, a halt in the rate of progress, alleviation of symptoms of the disorder, amelioration of the disorder, and cure of the disorder. Treatment as a prophylactic measure (i.e., prophylaxis) is also included. For example, use with patients who have not yet developed the disorder, but who are at risk of developing the disorder, is encompassed by the term "treatment."

The term "therapeutically-effective amount," as used herein, pertains to that amount of a compound, or a material, composition or dosage form comprising a compound, which is effective for producing some desired therapeutic effect, commensurate with a reasonable benefit/risk ratio, when administered in accordance with a desired treatment regimen.

Combination Therapies

The term "treatment" includes combination treatments and therapies, in which two or more treatments or therapies are combined, for example, sequentially or simultaneously. For example, the compounds described herein may also be used in combination therapies, e.g., in conjunction with other agents.

The particular combination would be at the discretion of the physician who would select dosages using his common general knowledge and dosing regimens known to a skilled practitioner.

The agents (i.e., the compound of Formula (1), Formula (2), or Formula (3), plus one or more other agents) may be administered simultaneously or sequentially, and may be administered in individually varying dose schedules and via different routes.

The agents (i.e., the compound of Formula (1), Formula (2), or Formula (3), plus one or more other agents) may be formulated together in a single dosage form, or alternatively, the individual agents may be formulated separately and presented together in the form of a kit, optionally with instructions for their use.

Kits

One aspect of the invention pertains to a kit comprising (a) a compound of Formula (1), Formula (2), or Formula (3), as described herein, or a composition comprising a compound of Formula (1), Formula (2), or Formula (3), as described herein, e.g., preferably provided in a suitable container and/or with suitable packaging; and (b) instructions for use, e.g., written instructions on how to administer the compound or composition.

The written instructions may also include a list of indications for which the active ingredient is a suitable treatment.

Routes of Administration

The compound of Formula (1), Formula (2), or Formula (3), or pharmaceutical composition comprising the compound, may be administered to a subject by any convenient route of administration. Typically, the compound is administered orally or intravenously.

The Subject/Patient

The subject/patient may be a mammal, a placental mammal, a marsupial (e.g., kangaroo, wombat), a rodent (e.g., a guinea pig, a hamster, a rat, a mouse), murine (e.g., a mouse), a lagomorph (e.g., a rabbit), avian (e.g., a bird), canine (e.g., a dog), feline (e.g., a cat), equine (e.g., a horse), porcine (e.g., a pig), ovine (e.g., a sheep), bovine (e.g., a cow), a primate, simian (e.g., a monkey or ape), a monkey (e.g., marmoset, baboon), an ape (e.g., gorilla, chimpanzee, orangutang, gibbon), or a human.

In one preferred embodiment, the subject/patient is a human.

Formulations

While it is possible for a compound of Formula (1), Formula (2), or Formula (3) to be administered alone, it is preferable to present it as a pharmaceutical formulation (e.g., composition, preparation, medicament) comprising at least one compound, as described herein, together with one or more other pharmaceutically acceptable ingredients well-known to those skilled in the art, including pharmaceutically acceptable carriers, diluents, excipients, adjuvants, fillers, buffers, preservatives, anti-oxidants, lubricants, stabilisers, solubilisers, surfactants (e.g., wetting agents), masking agents, colouring agents, flavouring agents, and sweetening agents. If formulated as discrete units (e.g., tablets, etc.), each unit contains a predetermined amount (dosage) of the compound. The formulation may further comprise other active agents, for example, other therapeutic or prophylactic agents.

Suitable carriers, diluents, excipients, etc. can be found in standard pharmaceutical texts. See, for example, *Handbook of Pharmaceutical Additives,* 2nd Edition (eds. M. Ash and I. Ash), 2001 (Synapse Information Resources, Inc., Endicott, N.Y., USA), *Reminqton's Pharmaceutical Sciences,* 20th edition, pub. Lippincott, Williams & Wilkins, 2000; and *Handbook of Pharmaceutical Excipients,* 5th edition, 2005.

The term "pharmaceutically acceptable," as used herein, pertains to compounds, ingredients, materials, compositions, dosage forms, etc., which are, within the scope of sound medical judgment, suitable for use in contact with the tissues of the subject in question (e.g., human) without excessive toxicity, irritation, allergic response, or other problem or complication, commensurate with a reasonable benefit/risk ratio. Each carrier, diluent, excipient, etc. must also be "acceptable" in the sense of being compatible with the other ingredients of the formulation.

The formulations may be prepared by any methods well known in the art of pharmacy. Such methods include the step of bringing into association the compound with a carrier which constitutes one or more accessory ingredients. In general, the formulations are prepared by uniformly and intimately bringing into association the compound with carriers (e.g., liquid carriers, finely divided solid carrier, etc.), and then shaping the product, if necessary.

The formulation may be prepared to provide for rapid or slow release; immediate, delayed, timed, or sustained release; or a combination thereof.

Formulations suitable for oral administration (e.g., by ingestion) include liquids, solutions (e.g., aqueous, non-aqueous), suspensions (e.g., aqueous, non-aqueous), emulsions (e.g., oil-in-water, water-in-oil), elixirs, syrups, electuaries, tablets, granules, powders, capsules, cachets, pills, ampoules, boluses.

Tablets may be made by conventional means, e.g., compression or moulding, optionally with one or more accessory ingredients. Compressed tablets may be prepared by compressing in a suitable machine the compound in a free-flowing form such as a powder or granules, optionally mixed with one or more binders (e.g., povidone, gelatin, acacia, sorbitol, tragacanth, hydroxypropylmethyl cellulose); fillers or diluents (e.g., lactose, microcrystalline cellulose, calcium hydrogen phosphate); lubricants (e.g., magnesium stearate, talc, silica); disintegrants (e.g., sodium starch glycolate, cross-linked povidone, cross-linked sodium carboxymethyl cellulose); surface-active or dispersing or wetting agents (e.g., sodium lauryl sulfate); preservatives (e.g., methyl p-hydroxybenzoate, propyl p-hydroxybenzoate, sorbic acid); flavours, flavour enhancing agents, and sweeteners. Moulded tablets may be made by moulding in a suitable machine a mixture of the powdered compound moistened with an inert liquid diluent. The tablets may optionally be coated or scored and may be formulated so as to provide slow or controlled release of the compound therein using, for example, hydroxypropylmethyl cellulose in varying proportions to provide the desired release profile. Tablets may optionally be provided with a coating, for example, to affect release, for example an enteric coating, to provide release in parts of the gut other than the stomach.

Formulations suitable for parenteral administration (e.g., by injection), include aqueous or non-aqueous, isotonic, pyrogen-free, sterile liquids (e.g., solutions, suspensions), in which the compound is dissolved, suspended, or otherwise provided (e.g., in a liposome or other microparticulate). Such liquids may additionally contain other pharmaceutically acceptable ingredients, such as anti-oxidants, buffers, preservatives, stabilisers, bacteriostats, suspending agents, thickening agents, and solutes which render the formulation isotonic with the blood (or other relevant bodily fluid) of the intended recipient. Examples of excipients include, for example, water, alcohols, polyols, glycerol, vegetable oils, and the like. Examples of suitable isotonic carriers for use in such formulations include Sodium Chloride Injection, Ringer's Solution, or Lactated Ringer's Injection. Typically, the concentration of the compound in the liquid is from about 1 ng/ml to about 10 μg/ml, for example from about 10 ng/ml to about 1 μg/ml. The formulations may be presented in unit-dose or multi-dose sealed containers, for example, ampoules and vials, and may be stored in a freeze-dried (lyophilised) condition requiring only the addition of the sterile liquid carrier, for example water for injections, immediately prior to use. Extemporaneous injection solutions and suspensions may be prepared from sterile powders, granules, and tablets.

Dosage

It will be appreciated by one of skill in the art that appropriate dosages of the compound of Formula (1), Formula (2), or Formula (3), and compositions comprising the compound can vary from patient to patient. Determining the optimal dosage will generally involve the balancing of the level of therapeutic benefit against any risk or deleterious side effects. The selected dosage level will depend on a variety of factors including the activity of the particular compound, the route of administration, the time of administration, the rate of excretion of the compound, the duration of the treatment, other drugs, compounds, and/or materials used in combination, the severity of the disorder, and the species, sex, age, weight, condition, general health, and prior medical history of the patient. The amount of compound and route of administration will ultimately be at the discretion of the physician, veterinarian, or clinician, although generally the dosage will be selected to achieve local concentrations at the site of action which achieve the desired effect without causing substantial harmful or deleterious side-effects.

Administration can be effected in one dose, continuously or intermittently (e.g., in divided doses at appropriate intervals) throughout the course of treatment. Methods of determining the most effective means and dosage of administration are well-known to those of skill in the art and will vary with the formulation used for therapy, the purpose of the therapy, the target cell(s) being treated, and the subject being treated. Single or multiple administrations can be carried out with the dose level and pattern being selected by the treating physician, veterinarian, or clinician.

Examples of Some Preferred Formulations

A preferred formulation is a dosage unit (e.g., a pharmaceutical tablet or capsule) comprising 20 to 300 mg of a compound of Formula (1), Formula (2), or Formula (3), as described herein; and a pharmaceutically acceptable carrier, diluent, or excipient.

In some embodiments, the dosage unit is a tablet.
In some embodiments, the dosage unit is a capsule.
In some embodiments, said capsules are gelatine capsules.
In some embodiments, said capsules are HPMC (hydroxypropylmethylcellulose) capsules.
In some embodiments, the amount is from about 30 to about 300 mg.
In some embodiments, the lower value is about 60 mg.
In some embodiments, the lower value is about 100 mg.
In some embodiments, the higher value is about 150 mg.
In some embodiments, the higher value is about 200 mg.
In some embodiments, the higher value is about 250 mg.
In some embodiments, the amount is about 30 mg.
In some embodiments, the amount is about 60 mg.
In some embodiments, the amount is about 100 mg.
In some embodiments, the amount is about 150 mg.
In some embodiments, the amount is about 200 mg.
In some embodiments, the amount is about 250 mg.
In some embodiments, the amount is about 300 mg.

The dosage amounts as set out above may refer to the amount of the compound itself or may refer to the amount of free base equivalent contained in the dosage unit. Both of these alternatives are specifically and explicitly disclosed by the present disclosure.

In some embodiments, the pharmaceutically acceptable carrier, diluent, or excipient is or comprises one or both of a glyceride (e.g., Gelucire 44/14 ®; lauroyl macrogol-32 glycerides PhEur, USP) and colloidal silicon dioxide (e.g., 2% Aerosil 200 ®; Colliodal Silicon Dioxide PhEur, USP).

EXAMPLES

The following worked examples are provided solely to illustrate the present invention and are not intended to limit the scope of the invention, as described herein.

Method 1

Synthesis of 3,7-Dinitro-10H-phenothiazine ("DNP")

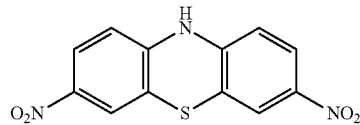 [SMILES: O=[N+]([O-])c1ccc2c(c1)Sc1cc([N+](=O)[O-])ccc1N2]

General Method A: Phenothiazine (1 equivalent), sodium nitrite (NaNO$_2$, 6.0-6.5 equivalents) and initial solvent(s) (see table below; 8-14 volumes) were added to a multi-necked round bottom flask. Glacial acetic acid (CH$_3$COOH, 2.9-6.0 volumes) was added drop-wise over the course of 45-60 minutes at ambient temperature (RT). The reaction mixture was stirred at ambient temperature for up to 22 hours depending upon the solvent(s) used. The mixture was then heated to reflux (or 100° C. if the boiling point of the solvent was above this temperature) and stirred for 3-19 hours depending upon the solvent(s) used. The mixture was cooled to ambient temperature and filtered using a Buchner funnel to give the crude product. The crude solid was washed with hot water (5×5 volumes) to remove the water soluble impurities, followed by washing with methanol (2×2 volumes). The solid was oven dried at 55° C. until a constant mass was reached to give the product as a purple/brown solid.

As used herein, a "volume" of liquid (e.g., solvent) is calculated as follows: 1 volume of solvent is equal to 1 ml of solvent for every 1 g of material. For example, in Batch B1 below, 14 ml of acetonitrile were used per gram of phenothiazine.

In Batch B1 below, 25 g of phenothiazine, 56.27 g of sodium nitrite, 350 ml of acetonitrile, and 75 ml of acetic acid were used.

TABLE 7

Reaction Conditions for DNP Synthesis

| DNP Batch No. | Solvent(s) | NaNO$_2$ (equiv.) | Conditions |
|---|---|---|---|
| B1 | (initial) Acetonitrile (14.0)<br>(added) Acetic acid (3.0)<br>(total 17.0) | 6.5 | RT (22 h)<br>reflux (4 h) |
| B2 | (initial) Dimethyl sulfoxide (10.0)<br>(added) Acetic acid (6.0)<br>(total 16.0) | 6.0 | RT (4 h)<br>reflux (15 h) |
| B3 | (initial) Tetrahydrofuran (10.0)<br>(added) Acetic acid (6.0)<br>(total 16.0) | 6.0 | RT (3 h)<br>reflux (15 h) |
| B4 | (initial) N,N-dimethylformamide (10.0)<br>(added) Acetic acid (6.0)<br>(total 16.0) | 6.0 | RT (2 h)<br>reflux (19 h) |
| B5 | (initial) Acetone (10.0)<br>(added) Acetic acid (6.0)<br>(total 16.0) | 6.0 | RT (2 h)<br>reflux (15 h) |
| B6 | (initial) Methyl tert-butyl ether (10.0)<br>(added) Acetic acid (6.0)<br>(total 16.0) | 6.0 | RT (1 h)<br>reflux (5 h) |
| T1 | (initial) Acetonitrile (7.5)<br>(initial) Sulfolane (2.5)<br>Acetic acid (6.0)<br>(total 16.0) | 6.0 | RT (2 h)<br>reflux (3 h) |
| T2 | (initial) Acetonitrile (11.0)<br>(initial) Tetrahydrofuran (3.0)<br>(added) Acetic acid (2.9)<br>(total 16.9) | 6.5 | RT (2 h)<br>reflux (2.5 h) |
| T3 | (initial) Acetonitrile (7.5)<br>(initial) Dimethylsulfoxide (2.5)<br>(added) Acetic acid (6.0)<br>(total 16.0) | 6.0 | RT (2 h)<br>reflux (3 h) |
| T4 | (initial) Acetonitrile (8.0)<br>(initial) N,N-dimethylformamide (2.0)<br>(added) Acetic acid (6.0)<br>(total 16.0) | 6.0 | RT (2 h)<br>reflux (3 h) |
| T5 | (initial) Acetonitrile (4.0)<br>(initial) Acetone (4.0)<br>(added) Acetic acid (3.5)<br>(total 11.5) | 6.5 | RT (2 h)<br>reflux (15 h) |
| T6 | (initial) Acetone (10.0)<br>(initial) Tetrahydrofuran (2.0)<br>(added) Acetic acid (6.0)<br>(total 18.0) | 6.0 | RT (3 h)<br>reflux (17 h) |

The product of DNP Batch B1 was characterised as follows:

TABLE 8

Characterisation of DNP Product (DNP Batch B1)

| | |
|---|---|
| $^1$H NMR (400 MHz, DMSO-d$_6$) | δ = 6.75 (d, J = 9.2, 2H), 7.79 (d, J = 2.8, 2H), 7.89 (dd, J = 2.8, 9.2, 2H), 10.12 (s, 1H) |
| IR ν$_{max}$ (KBr) cm$^{-1}$ | 3331(s), 3101(m), 3095(m), 3067(m), 1605(m), 1564(m), 1504(m) 1482(s), 1311(s), 1272(s), 1126(s) |

Yield and purity of the crude product (as measured by HPLC) are summarised in Table 12 below. Yields are corrected for DNP purity.

As used herein, "HPLC % (a/a)" refers to "HPLC percent area by area", and denotes the ratio of the area under the HPLC peak associated with the chemical species to the total area under all of the HPLC peaks observed, expressed as a percent. For example, "DNP % (a/a)" denotes the ratio of the area under the HPLC peak associated with DNP to the total area under all of the HPLC peaks observed, multiplied by 100.

Similarly, as used herein, "HPLC % (w/w)" refers to "HPLC percent weight by weight", and denotes the ratio of the area under the HPLC peak compared with the area under the HPLC peak of a reference standard, expressed as a percent. For example, "LMTM % (w/w)" denotes the ratio of the area under the LMTM peak compared against the area under the peak of a LMTM reference standard of known concentration, multiplied by 100.

The HPLC parameters are summarised in the following tables. HPLC samples where prepared using 100 mL clear-glass volumetric flasks. In preparing solutions, 19-21 mg of sample were dissolved in 60 ml of tetrahydrofuran (THF), sonicated for 5 minutes, and then diluted to the graduation mark with hexane.

TABLE 9

HPLC Parameters for DNP System Parametrs

| | |
|---|---|
| HPLC system | Agilent 1100 with DAD and data handling capacity |
| Column | Agilent Rx-Sil, 250 × 4.6 mm, 5 μm particle size |
| Column Temperature | 25° C. |
| Autosampler Temperature | Ambient |
| Mobile Phase | A: Hexane, 95 %<br>B: THF |
| Flow Rate | 1 mL/min |
| Injection volume | 25 μL |
| Stop time | 60 min |
| Wavelength | 285 nm, slit width 4 nm |

TABLE 10

HPLC Parameters for DNP Solvent Gradient Parameters

| Time, min | A, % | B, % | Flow, mL/min |
|---|---|---|---|
| 0 | 80 | 20 | 1 |
| 25 | 70 | 30 | 1 |
| 30 | 50 | 50 | 1 |
| 35 | 50 | 50 | 1 |
| 40 | 0 | 100 | 1 |
| 50 | 0 | 100 | 1 |
| 51.0 | 80 | 20 | 1 |

TABLE 11

Typical Retention Times for DNP Analysis (at 285 nm)

| Compound | Retention Time (minutes) |
|---|---|
| Phenothiazine | 5.47 |
| T$_3$NP | 5.72 |
| T$_4$NP | 7.23 |
| MNP | 14.74 |
| DNP | 33.84 |

TABLE 12

Yield and Impurities

| DNP Batch No. | Yield (%) | HPLC (% a/a) | |
|---|---|---|---|
| B1 | 91 | DNP | 96.76 |
| | | MNP | 1.03 |
| | | T$_3$NP | 1.48 |
| | | Others | 0.73 |
| B2 | 72 | DNP | 90.75 |
| | | MNP | 2.36 |
| | | T$_3$NP | 1.51 |

TABLE 12-continued

Yield and Impurities

| DNP Batch No. | Yield (%) | HPLC (% a/a) | |
|---|---|---|---|
| | | Others | 5.38 |
| B3 | 85 | DNP | 90.62 |
| | | MNP | 5.69 |
| | | $T_3NP$ | 0.58 |
| | | Others | 3.11 |
| B4 | 79 | DNP | 85.90 |
| | | MNP | 4.47 |
| | | $T_3NP$ | 4.78 |
| | | $T_4NP$ | 0.05 |
| | | Others | 4.80 |
| B5 | 75 | DNP | 80.24 |
| | | MNP | 15.67 |
| | | Others | 4.09 |
| B6 | 69 | DNP | 74.63 |
| | | MNP | 10.21 |
| | | $T_3NP$ | 1.06 |
| | | Others | 14.10 |

TABLE 12

Yield and Impurities

| DNP Batch No. | Yield (%) | HPLC (% a/a) | |
|---|---|---|---|
| T1 | 90 | DNP | 94.76 |
| | | MNP | 1.19 |
| | | $T_3NP$ | 1.35 |
| | | Others | 2.70 |
| T2 | 87 | DNP | 93.64 |
| | | MNP | 4.23 |
| | | Others | 2.13 |
| T3 | 86 | DNP | 92.31 |
| | | MNP | 3.34 |
| | | $T_3NP$ | 1.45 |
| | | Others | 2.90 |
| T4 | 86 | DNP | 91.29 |
| | | MNP | 4.84 |
| | | $T_3NP$ | 0.53 |
| | | Others | 3.34 |
| T5 | 86 | DNP | 91.20 |
| | | MNP | 4.59 |
| | | Others | 4.21 |
| T6 | 82 | DNP | 86.16 |
| | | MNP | 10.24 |
| | | $T_3NP$ | 0.26 |
| | | Others | 3.34 |

The term "others" refers to all other compounds that are present, for which a specific value is not reported.

For reference, the chemical structures of DNP and the related impurities are shown in the following table.

TABLE 13

Chemical Structure of DNP and Related Impurities

| 3-nitro-10H-phenothiazine (MNP) | 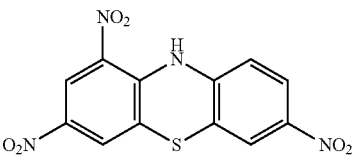 [SMILES: O=[N+]([O-])c1ccc2c(c1)Sc1cc([N+](=O)[O-])cc([N+](=O)[O-])c1N2] |
|---|---|
| 3,7-Dinitro-10H-phenothiazine (DNP) | 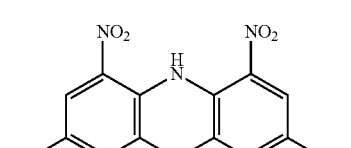 |
| 1,3,7-trinitro-10H-phenothiazine ($T_3NP$) | 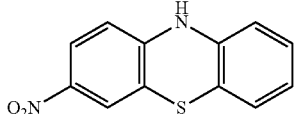 |
| 1,3,7,9-tetranitro-10H-phenothiazine ($T_4NP$) | 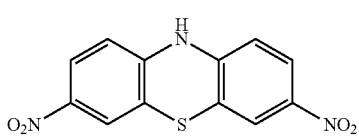 |

Method 2

Recrystallisation of 3,7-Dinitro-10H-Phenothiazine ("DNP")

General Method B: 3,7-dinitro-1 OH-phenothiazine (1.0 equivalent) and solvent (see table below; 5-10 volumes) were added to a round bottom flask. The mixture was heated to 100° C. and stirred at this temperature for 1-2 hours. After this time, the mixture was slowly cooled to ambient temperature (21-23° C.) and stirred at this temperature for 2-3 hours. The product was collected by filtration using a Buchner funnel and washed with solvent (2-3×2 volumes). After drying at 40-50° C. in a vacuum oven for 16 hours the product purity was determined by HPLC analysis. Yields in the table below are corrected for starting material and product purity.

TABLE 14

DNP Yield and HPLC Purity Following Recrystallisation

| Crude purity HPLC (% a/a) | | Recrystallisation Solvent | Solvent volume | Yield (%) | Product purity HPLC (% a/a) | |
|---|---|---|---|---|---|---|
| DNP | 89.23 | Dimethyl sulfoxide | 5.0 | 95 | DNP | 97.30 |
| MNP | 5.74 | | | | MNP | 1.18 |
| $T_3NP$ | 1.75 | | | | $T_3NP$ | 0.17 |
| Others | 3.28 | | | | Others | 1.35 |
| DNP | 89.23 | Dimethyl sulfoxide | 10.0 | 91 | DNP | 98.27 |
| MNP | 5.74 | | | | MNP | 0.34 |
| $T_3NP$ | 1.75 | | | | $T_3NP$ | 0.08 |
| Others | 3.28 | | | | Others | 1.31 |
| DNP | 92.31 | N,N-dimethylacetamide | 5.0 | 82 | DNP | 98.71 |
| MNP | 3.34 | | | | MNP | 0.12 |
| $T_3NP$ | 1.45 | | | | Others | 1.17 |
| Others | 2.90 | | | | | |
| DNP | 92.31 | N-methyl-2-pyrrolidone | 5.0 | 64 | DNP | 99.19 |
| MNP | 3.34 | | | | MNP | 0.06 |
| $T_3NP$ | 1.45 | | | | Others | 0.75 |
| Others | 2.90 | | | | | |
| DNP | 92.31 | N,N-dimethylformamide | 5.0 | 85 | DNP | 98.29 |
| MNP | 3.34 | | | | MNP | 0.35 |
| $T_3NP$ | 1.45 | | | | $T_3NP$ | 0.23 |
| Others | 2.90 | | | | Others | 1.13 |

Again, the term "others" refers to all other compounds that are present, for which a specific value is not reported.

Method 3

Crystal Structure Determination of 3,7-Dinitro-10H-Phenothiazine DMSO Solvate Crystals were grown from a dimethylsulfoxide (DMSO) solution of the recrystallized product above, and crystallographic analysis confirmed that the crystals were 3,7-dinitro-10H-phenothiazine as a DMSO solvate.

Figure 2:
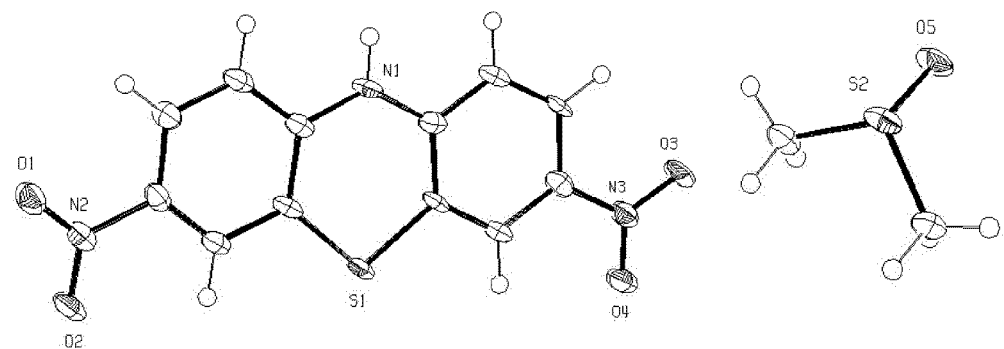
FIG. 2 shows the crystallographic structure of the 3,7-dinitro-10H-phenothiazine (DMSO solvate), as described in Method 3 below.

FIG. 2 shows the crystallographic structure of the 3,7-dinitro-10H-phenothiazine (DMSO solvate).

The crystal data and structure refinement for the DNP.DMSO solvate are as follows:

TABLE 15

| Crystal Structure Data for DNP | |
|---|---|
| Identification code | 5750CM029_0m |
| Empirical formula | $C_{14}H_{13}N_3O_5S_2$ |
| Formula weight | 367.39 |
| Temperature | 150(2)K |
| Wavelength | 0.71073 Å |
| Crystal system | Monoclinic |
| Space group | P2(1)/c |
| Unit cell dimensions | a = 13.5398(11) Å   $\alpha = 90°$ |
|  | b = 4.4722(4) Å   $\beta = 99.633(6)°$ |
|  | c = 25.2996(17) Å   $\gamma = 90°$ |
| Volume | 1510.4(2) Å$^3$ |
| Z | 4 |
| Density (calculated) | 1.616 Mg/m$^3$ |
| Absorption coefficient | 0.385 mm$^{-1}$ |
| F(000) | 760 |
| Crystal size | 0.21 × 0.05 × 0.01 mm$^3$ |
| Theta range for data collection | 1.53 to 27.41° |
| Index ranges | −17 <= h <= 17, −5 <= k <= 4, −32 <= l <= 32 |
| Reflections collected | 14697 |
| Independent reflections | 3422 [R(int) = 0.1138] |
| Completeness to theta = 27.41° | 99.5% |
| Absorption correction | Semi-empirical from equivalents |
| Max. and min. transmission | 0.9962 and 0.9235 |
| Refinement method | Full-matrix least-squares on F$^2$ |
| Data/restraints/parameters | 3422/0/219 |
| Goodness-of-fit on F$^2$ | 1.000 |
| Final R indices [ I > 2sigma(I)] | R1 = 0.0605, wR2 = 0.1448 |
| R indices (all data) | R1 = 0.1377, wR2 = 0.2084 |
| Largest diff. peak and hole | 0.537 and −0.908 e · Å$^{-3}$ |

Method 4

Synthesis of N,N,N',N'-tetramethyl-10H-phenothiazine-3,7-diaminium bis(methanesulfonate) ("LMTM")

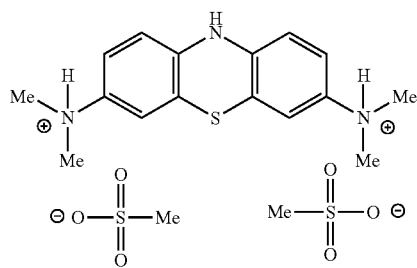 [SMILES: C[NH+](C)c1ccc2c(c1)Sc1cc([NH+](C)C)ccc1N2 ; CS(=O)(=O)[O-] ; CS(=O)(=O)[O-]]

Part 1: To a 450 ml pressure vessel, fitted with an entrainment stirrer, thermometer, pressure gauge and connected to a pressure burette, was added 3,7-dinitro-10H-phenothiazine (DNP, 5.00 g, 17.28 mmol, 1 equivalent), palladium on carbon (5% (w/w) Pd, 58% (w/w) water, 1.15 g, 0.0131 equivalents), and N,N-dimethylformamide (150 ml). The pressure burette and vessel were then purged with hydrogen five times to 10 bar before the burette was pressurised with hydrogen to 20.4 bar and the vessel to 3.7 bar. The mixture was stirred (1500 rpm) at ambient temperature for 90 minutes (i.e., until the nitro group reduction was complete, as indicated by approximately 60% up-take of hydrogen).

Part 2: The vessel was vented and paraformaldehyde (H$_2$CO, 97%, 2.08 g, 67.39 mmol, 3.9 equivalents) was added to the reaction mixture in one aliquot. The vessel was re-pressurised with hydrogen to 3.6 bar and heated to 90° C. while stirring at 1500 rpm. Progress of the reaction was monitored via hydrogen uptake, temperature, and pressure (see FIG. 3). The reaction reached completion after approximately 16 hours (i.e., when the hydrogen up-take had reached approximately 100%, or had plateaued). After a further 8 hours (24 hours in total), the reaction mixture (a green solution) was cooled to 23° C., and the vessel vented. The catalyst was removed by filtration using a Buchner funnel (12 cm diameter) and the filtrate was collected in a round bottom flask. The catalyst was washed with N,N-dimethylformamide (2×15 ml) and the combined filtrate and washings were distilled to dryness under reduced pressure giving a purple solid.

Figure 3:
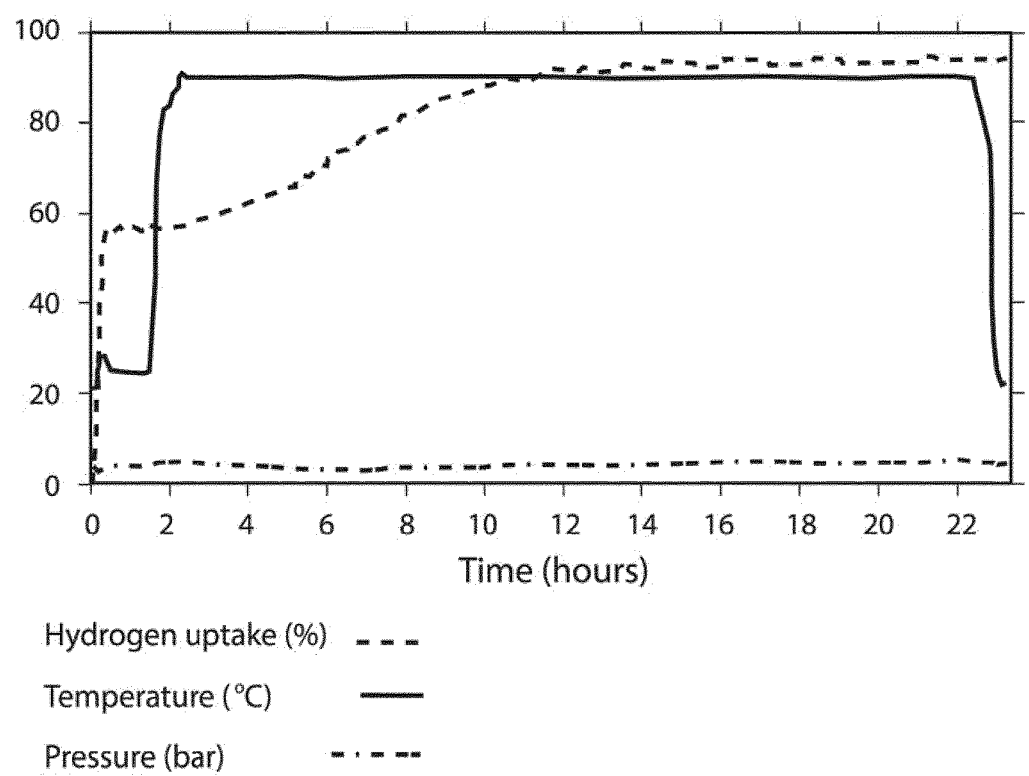
FIG. 3 is a graph of hydrogen uptake (%), vessel temperature (° C.), and vessel pressure (bar) versus time (hours) for the reaction in which the nitro groups of 3,7-dinitro-10H-phenothiazine (DNP) are reduced, and the resulting amino groups are selectively alkylated, as described in Method 4 below.

FIG. 3 is a graph of hydrogen uptake (%), vessel temperature (° C.), and vessel pressure (bar) versus time (hours) for the reaction in which the nitro groups of 3,7-dinitro-10H-phenothiazine (DNP) are reduced, and the resulting amino groups are selectively alkylated.

Part 3: The round bottom flask containing the purple solid was purged with argon before toluene (3 ml), methanol (10 ml) and methane sulfonic acid (5.22 g, 38.02 mmol, 2.2 equivalents) were added. The resultant solution was cooled to 5° C. Ethanol (30 ml) was added drop-wise as an anti-solvent, which caused the product to precipitate as a green crystalline solid. The slurry was stirred at 5° C. for 2 hours and then filtered to give green crystals, which were washed with ethanol (4×10 ml, cooled to 5° C.) giving the product as yellow crystals, which were dried to constant weight in a 50° C. vacuum oven at 10 mm Hg (1333 kPa) (6.59 g, yield 80%).

The LMTM product was characterised as follows:

TABLE 16

Characterisation of LMTM Product

| | |
|---|---|
| $^1$H NMR (300 MHz, CD$_3$OD) | δ = 2.72 (s, 6H), 3.22 (s, 12H), 7.23 (m, 4H), 6.77 (dd, J = 6, 3 Hz, 2H) |

The organic purity of the LMTM product was determined by HPLC analysis and the results are summarised in the following table.

TABLE 17

LMTM Purity by HPLC (% w/w)

| | |
|---|---|
| LMTM (free base) | 93.69 |
| Leuco Azure B Mesylate (free base) | 3.85 |
| MTM (free base) | 0.58 |
| Others | 1.88 |
| Total | 100.00 |

Again, the term "others" refers to all other compounds that are present, for which a specific value is not reported.

The HPLC parameters are summarised in the following tables.

TABLE 18

HPLC parameters for LMTM
System Parametrs

| | |
|---|---|
| HPLC system | Agilent 1200 with DAD and data handling capacity |
| Column | Agilent Zorbax SB-CN, 50 × 4.6 mm, 3 μm particle size |
| Column Temperature | 10° C. |
| Autosampler Temperature | 5° C. |
| Mobile Phase | A: Degassed 0.1% v/v formic acid B: Degassed acetonitrile |
| Flow Rate | 1 mL/min |
| Injection volume | 5 μL |
| Stop time | 22.0 min |
| Wavelength | 255 nm, slit width 4 nm |

TABLE 19

HPLC parameters for LMTM
Solvent Gradient Parameters

| Time, min | A, % | B, % | Flow, mL/min |
|---|---|---|---|
| 0 | 100 | 0 | 1 |
| 10 | 90 | 10 | 1 |
| 17 | 50 | 50 | 1 |
| 18 | 50 | 50 | 1 |
| 18.1 | 100 | 0 | 1 |
| 22 | 100 | 0 | 1 |

HPLC standards and samples were prepared as follows:
Fresh LMTM reference material was used when preparing standards (for determination of retention times and quantification of samples).
50 mL amber-glass volumetric flasks used to prepare standards and samples.
Amber-glass vials filled as much as possible; using a volumetric pipette, the ideal volume was 1.85 mL (which allows for expansion upon chilling of solution).
All glassware pre-rinsed with 0.1% formic acid, oven-dried, and degassed with argon prior to use.
All eluents and diluent (0.1% formic acid) degassed thoroughly (at least 10 min of vigorous degassing), prior to use. For the diluent, degassed for 5 minutes once every hour during a sample run.
Samples were pre-weighed (about 42 mg) into flasks, and stoppered, prior to wetting.
Samples are not wetted more than 10 minutes prior to injection.
Ensure complete material dissolution prior to solution sampling. This was done by inverting the flask, rotating argon bubble around the bottom of the flask a number of times, checking for undissolved material, and then re-invert the solution to ensure thorough mixing.

TABLE 20

Typical Retention Times for LMTM Analysis
(at 255 nm)

| Compound | Retention time (minutes) |
|---|---|
| Leuco Azure B Mesylate (free base) | 5.9 |
| LMTM (free base) | 6.58 |
| Azure B Mesylate (free base) | 14.10 |
| MTM (free base) | 14.37 |

For reference, the chemical structures of LMTM and the related impurities are shown in the following table.

TABLE 21

Chemical Structures of LMTM and Related Impurities

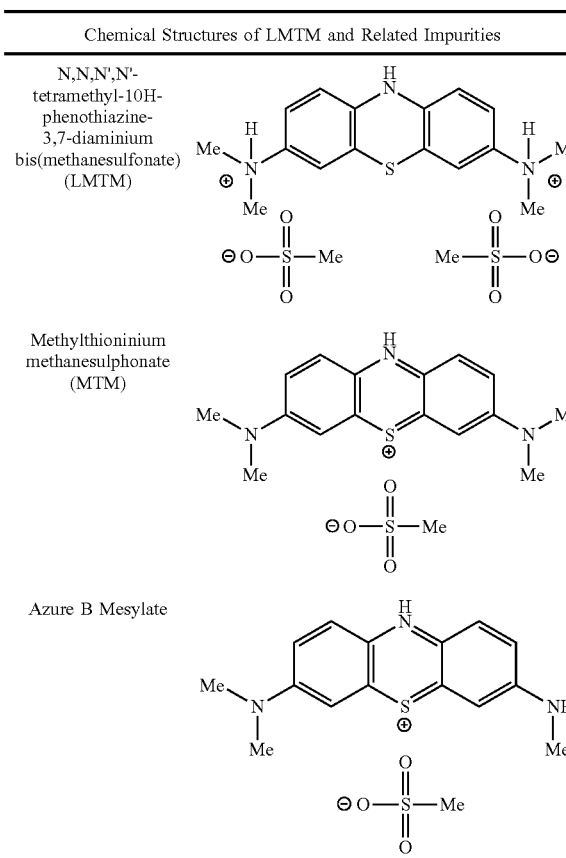

| | |
|---|---|
| N,N,N',N'-tetramethyl-10H-phenothiazine-3,7-diaminium bis(methanesulfonate) (LMTM) | |
| Methylthioninium methanesulphonate (MTM) | |
| Azure B Mesylate | |

TABLE 21-continued

Chemical Structures of LMTM and Related Impurities

N,N,N'-trimethyl-10H-phenothiazine-3,7-diaminium bis(methanesulphonate) (Leuco Azure B Mesylate)

Method 5

"Two Pot" Synthesis of Methylthioninium Chloride ("MTC")

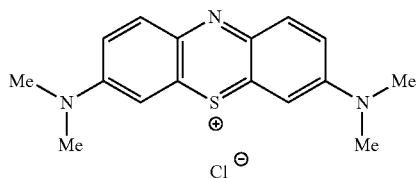 [SMILES: CN(C)c1ccc2nc3ccc(N(C)C)cc3[s+]c2c1 ; [Cl-]]

Part 1: To a 450 ml pressure vessel, fitted with an entrainment stirrer, thermometer, pressure gauge and connected to a pressure burette, was added 3,7-dinitro-10H-phenothiazine ("DNP", 5.00 g, 17.28 mmol, 1 equivalent), palladium on carbon (5% (w/w) Pd, 58% (w/w) water, 1.15 g, 0.0131 equivalents), and N,N-dimethylformamide (150 ml). The pressure burette and vessel were then purged with hydrogen five times to 15 bar before the burette was pressurised with hydrogen to 20.4 bar and the vessel to 3.7 bar. The mixture was stirred (1500 rpm) at ambient temperature for approximately 60 minutes (i.e., until the nitro group reduction was complete, as indicated by approximately 60% up-take of hydrogen).

Part 2: The vessel was vented and paraformaldehyde ($H_2CO$, 95.6%, 2.28 g, 73 mmol, 4.2 equivalents) was added to the reaction mixture in one aliquot. The vessel was purged again with hydrogen, 5 times to 15 bar and re-pressurised with hydrogen to 3.6 bar and heated to 90° C. while stirring at 1500 rpm. Progress of the reaction was monitored via hydrogen uptake, temperature, and pressure. The reaction reached completion after approximately 16 hours (i.e., when the hydrogen up-take had reached approximately 100% or had plateaued). The reaction mixture (a green solution) was cooled to ambient temperature, and the vessel vented. The catalyst was removed by filtration using a Buchner funnel (12 cm diameter) and the filtrate was collected in a round bottom flask containing 32% hydrochloric acid (4.24 g, 37 mmol, 2.15 equivalents) that was submersed in an ice bath. The catalyst was washed with N,N-dimethylformamide (3×10 ml) and the filtrate and washings were combined.

Part 3: The combined filtrate and washings were cooled to 5° C. before iron (III) chloride hexahydrate ($FeCl_3 \cdot 6H_2O$, 9.81 g, 36 mmol, 2.1 equivalents) dissolved in water (14 ml) was added drop-wise over 30 minutes. Once addition of the iron (III) chloride solution was complete, the reaction mixture was stirred for a further 2 hours at 5° C. The golden green needles that precipitated were collected by filtration using a Buchner funnel and were dried on the filter for 1 hour and then oven dried at 50° C. for 16 hours. The mass of product obtained was 3.88 g (Batch 1). The filtrate was stirred for a further 3 days at ambient temperature and gave a second crop of product (2.10 g) (Batch 2). The combined mass of product was 5.98 g.

TABLE 22

Characterisation of "Two-Pot" MTC Product

| | MTC Batch 1A (1st Crop) | MTC Batch 1B (2nd Crop) |
|---|---|---|
| Weight loss on drying (moisture balance) | 20.91% | 2.99% |
| $^1$H NMR (300 MHz, $D_2O$) | δ = 2.91 (s, 12H), 6.58 (s, 2H), 6.81 (d, J = 9 Hz, 2H), 7.06 (d, J = 9 Hz, 2H) | δ = 2.84 (s, 12H), 6.52 (s, 2H), 6.73 (d, J = 9 Hz, 2H), 6.97 (d, J = 9 Hz, 2H) |
| HPLC (w/w) | 77.98% | 43.63% |
| Yield of MTC | 56% | 17% |

The organic purity of the MTC product was determined by HPLC analysis and the results are summarised in the following table.

TABLE 23

HPLC Purity of MTC Product

| | MTC Batch 1A (1st Crop) % (a/a) | MTC Batch 1B (2nd Crop) % (a/a) |
|---|---|---|
| MTC | 99.75 | 77.12 |
| Azure B | 0.22 | 0.72 |
| Azure A | — | 0.19 |
| Azure C | — | — |
| MVB | — | <0.05 |
| MVB-$CH_3$ | — | — |
| sDMT | — | <0.05 |
| Others | 0.03 | 21.97 |
| Total | 100 | 100 |

The term "others" refers to all other compounds that are present, for which a specific value is not reported.

TABLE 24

HPLC parameters for MTC System Parametrs

| | |
|---|---|
| HPLC system | Agilent 1200 with DAD and data handling capacity |
| Column | Agilent Zorbax XDB-Phenyl, 150 × 4.6 mm, 3 μm particle size |
| Column Temperature | 50° C. |
| Autosampler Temperature | 5° C. |
| Mobile Phase | A: 0.1% v/v trifluoroacetic acid B: Acetonitrile |
| Flow Rate | 1.5 mL/min |
| Injection volume | 50 μL |
| Stop time | 25.0 min |
| Wavelength | 284 nm, slit width 4 nm |

TABLE 25

HPLC parameters for MTC Solvent Gradient Parameters

| Time, min | A, % | B, % | Flow, mL/min |
|---|---|---|---|
| 0 | 90 | 10 | 1.5 |
| 1 | 90 | 10 | 1.5 |
| 13 | 75 | 25 | 1.5 |
| 18 | 40 | 60 | 1.5 |
| 20 | 40 | 60 | 1.5 |
| 20.1 | 90 | 10 | 1.5 |
| 25 | 90 | 10 | 1.5 |

HPLC standards and samples were prepared as follows:

Fresh MTC reference material always used when preparing MTC stock and LLOQ standards. Stock and LLOQ standards were used for determination of retention time and quantification.

25 and 100 mL amber-glass volumetric flasks used to prepare standards and samples.

Concentrated solutions were prepared using 34-38 mg of sample. The sample was dissolved in 50 mL of diluent (90:10, 0.1% TFA:acetonitrile), sonicated for 5 minutes, and then diluted to the graduation mark with diluent. Solutions were then allowed to stand for 1 hour prior to a 1:10 dilution.

For runs, 2 L of 0.1% TFA and 1 L of acetonitrile was used for the eluents.

TABLE 26

Typical Retention Times for MTC Analysis (at 255 nm)

| Compound | Retention time (minutes) |
|---|---|
| Thionine | 8.79 |
| MVB-2CH$_3$ | 9.00 |
| MVB-CH$_3$ | 10.34 |
| Azure C | 10.93 |
| MVB | 11.78 |
| Azure A | 13.17 |
| sDMT | 13.47 |
| Azure B | 15.56 |
| MTC | 16.53 |

For reference, the chemical structures of MTC and the related impurities are shown in the following table.

TABLE 27

Chemical Structures of MTC and Related Impurities

| Compound | Structure |
|---|---|
| Methylthioninium chloride (MTC) | [structure] |
| Azure A | [structure] |
| Azure B | [structure] |
| Azure C | [structure] |
| Methylene Violet Bernthsen (MVB) | [structure] |
| 7-(methylamino)-3H-phenothiazine-3-one (MVB-CH$_3$) | [structure] |
| 7-amino-3H-phenothiazine-3-one (MVB-2CH$_3$) | [structure] |
| Thionine | [structure] |
| Symmetrical Dimethyl Thionine (sDMT) | [structure] |

Method 6

"One Pot" Synthesis of Methylthioninium Chloride ("MTC")

Part 1: To a 450 ml pressure vessel, fitted with an entrainment stirrer, thermometer, pressure gauge and connected to a pressure burette, was added 3,7-dinitro-10H-phenothiazine (DNP, 15 g, 51.8 mmol, 1 equivalent), palladium on carbon (5% (w/w) Pd, 58% (w/w) water, 3.45 g, 0.0131 equivalents), paraformaldehyde ($H_2CO$, 95.6%, 6.52 g, 207 mmol, 4.0 equivalents) and N,N-dimethylformamide (150 ml). The pressure burette and vessel were then purged with hydrogen five times to 15 bar before the burette was pressurised with hydrogen to 60.1 bar and the vessel to 3.8 bar. The mixture was stirred (1500 rpm) at ambient temperature for approximately 120 minutes (i.e., until the nitro group reduction was complete, as indicated by approximately 60% up-take of hydrogen).

Part 2: The reaction mixture was then heated to 90° C. while stirring at 1500 rpm. Progress of the reaction was monitored via hydrogen uptake and temperature (see FIG. 4). The reaction reached completion after approximately 16 hours (i.e., when the hydrogen up-take had reached approximately 100%, or had plateaued). The reaction mixture (a green solution) was cooled to ambient temperature, and the vessel vented. The catalyst was removed by filtration using a Buchner funnel (12 cm diameter) and the filtrate was collected in a round bottom flask containing 32% hydrochloric acid (12.7 g, 111 mmol, 2.15 equivalents) that was submersed in an ice bath. The catalyst was washed with N,N-dimethylformamide (3×10 ml) and the filtrate and washings were combined.

Figure 4:
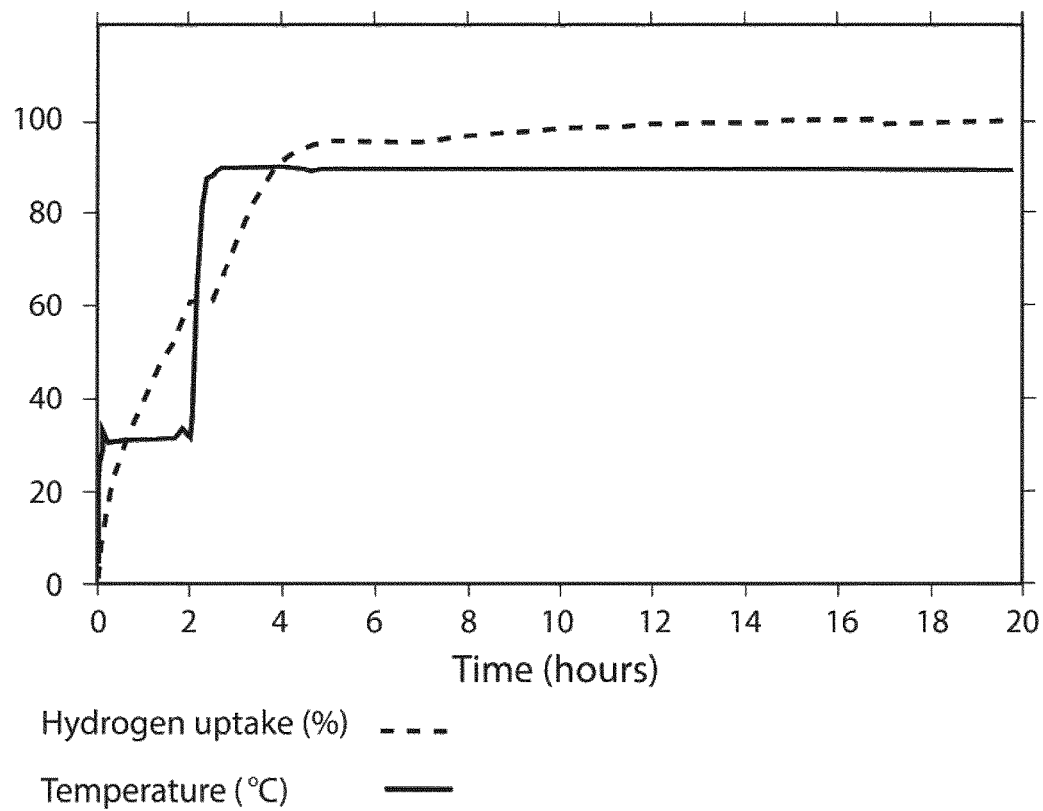
FIG. 4 is a graph of hydrogen uptake (%) and vessel temperature (° C.) versus time (hours) for the reaction in which the nitro groups of 3,7-dinitro-10H-phenothiazine (DNP) are reduced, and the resulting amino groups are selectively alkylated, as described in Method 6 below.

FIG. 4 is a graph of hydrogen uptake (%) and vessel temperature (° C.) versus time (hours) for the reaction in which the nitro groups of 3,7-dinitro-10H-phenothiazine (DNP) are reduced, and the resulting amino groups are selectively alkylated.

Part 3: The combined filtrate and washings were cooled to 5° C. before iron (III) chloride hexahydrate ($FeCl_3.6H_2O$, 29.43 g, 109 mmol, 2.1 equivalents) dissolved in water (42 ml) was added drop-wise over 30 minutes. Once addition of the iron (III) chloride solution was complete, the reaction mixture was stirred for a further 2 hours at 5° C. The golden green needles that precipitated were collected by filtration using a Buchner funnel and were dried on the filter for 1 hour and then oven dried at 50° C. for 16 hours. The mass of product obtained was 15.66 g.

The MTC product was characterised as follows:

TABLE 28

Characterisation of "One-Pot" MTC Product
MTC Batch 2

| | |
|---|---|
| Weight loss on drying (moisture balance) | 8.52% |
| $^1$H NMR (300 MHz, $D_2O$) | δ = 3.00 (s, 12H), 6.68 (s, 2H), 6.91 (d, J = 9 Hz, 2H), 7.18 (d, J = 9 Hz, 2H) |
| IR $v_{max}$ (cm$^{-1}$) | 3305(b, $H_2O$ 'Solvate'), 1592(s), 1485(m), 1389(s), 1329(s), 1169(m), 1130(m), 866(s) |
| MS, m/z (ESI): | [M$^+$] 284 |
| HPLC (a/a) | 98.15% |
| HPLC (w/w) | 76.55% |
| Accurate yield of MTC | 75% |

The organic purity of the MTC product was determined by HPLC analysis and the results are summarised in the following table.

TABLE 29

HPLC Purity of "One-Pot" MTC Product

| | MTC Batch 2 % (a/a) |
|---|---|
| MTC | 98.15 |
| Azure B | 1.33 |
| Azure A | 0.09 |
| Azure C | — |
| MVB | — |
| MVB-CH$_3$ | — |
| sDMT | 0.11 |
| Others | 0.32 |
| Total | 100 |

Additional batches were prepared using similar methods and characterised, as described in the following tables.

TABLE 30

Characterisation of Additional Batches of "One-Pot" MTC Product

| | MTC Batch 3A (1st Crop) | MTC Batch 3B (2nd Crop) | MTC Batch 4 | MTC Batch 5 |
|---|---|---|---|---|
| DMF wash volume | 30 ml | (*) | 30 ml | 30 ml |
| Amount of $CH_2O$ | 4.2 eq. | 4.2 eq. | 4.2 eq. | 4.0 eq. |
| Amount of catalyst | 0.0131 eq. | 0.0131 eq. | 0.0131 eq. | 0.0066 eq. |
| Weight loss on drying (moisture balance) | 4.88% | 2.11% | 8.03% | 8.70% |
| HPLC (a/a) | 99.63% | 99.65% | 98.09% | 99.06% |
| HPLC (w/w) | 77.12% | 78.86% | 74.61% | 76.59% |
| Accurate yield of MTC | 58% | 9% | 67% | 80% |

(*) The second crop was not washed.

For MTC Batch 3A, a 2nd Crop was obtained by stirring the filtrate for 1 day at ambient temperature to give MTC Batch 3B.

The organic purity of the MTC product was determined by HPLC analysis and the results are summarised in the following table.

TABLE 31

HPLC Purity of MTC Product

| | MTC Batch 3A (1st Crop) % (a/a) | MCT Batch 3B (2nd Crop) % (a/a) |
|---|---|---|
| MTC | 99.63 | 99.65 |
| Azure B | 0.29 | 0.19 |
| Azure A | <0.05 | 0.10 |
| Azure C | — | — |
| MVB | — | — |
| MVB-CH$_3$ | — | — |
| sDMT | — | — |
| Others | 0.08 | 0.06 |
| Total | 100 | 100 |

TABLE 32

HPLC Purity of MTC Product

| | MTC Batch 4 % (a/a) | MTC Batch 5 % (a/a) |
|---|---|---|
| MTC | 98.09 | 99.06 |
| Azure B | 1.0 | 0.44 |
| Azure A | 0.19 | 0.06 |
| Azure C | — | — |
| MVB | — | <0.05 |
| MVB-CH$_3$ | <0.05 | — |
| sDMT | <0.05 | <0.05 |
| Others | 0.72 | 0.44 |
| Total | 100 | 100 |

Method 7

Purification of Methylthioninium Chloride ("MTC") by Recrystallisation

Methylthioninium chloride (MTC, 10 g, from Batch 2) and aqueous hydrochloric acid (120 ml) (prepared as 50 parts water and 1 part 32% hydrochloric acid) were added to a 250 ml round bottom flask. The mixture was heated to 70° C. and stirred until the solid dissolved. The solution was then cooled to approximately 22° C. and stirred for 16 hours. The golden green needles that precipitated were collected by filtration using a Buchner funnel and washed with aqueous hydrochloric acid (3×10 ml; as above) that had been cooled to 5° C. The crystals were dried on the filter for 2 hours before being oven dried at 50° C. for 2 hours to give 8.66 g of MTC as a golden green solid.

The purified and recrystallized MTC product was characterised as follows:

TABLE 33

Characterisation of Recrystallized MTC (MTC Batch 6)

| | |
|---|---|
| Weight loss on drying (moisture balance) | 10.68% |
| $^1$H NMR (300 MHz, D$_2$O) | δ = 3.01 (s, 12H), 6.70 (s, 2H), 6.90-6.93 (d, J = 9 Hz, 2H), 7.18-7.21 (d, J = 9 Hz, 2H) |
| $^{13}$C NMR (75 MHz, D$_2$O) | δ = 40.49 (4C), 105.83 (2C), 118.11 (2C), 133.37 (2C), 133.66 (2C), 136.09 (2C), 152.84 (2C) |
| IR ν$_{max}$ (cm$^{-1}$) | 3339(b, H$_2$O 'Solvate'), 1594(s), 1489(m), 1391(s), 1333(s), 1170(m), 1142(m), 877(s) |
| MS, m/z (ESI): | [M$^+$] 284 |
| HPLC (a/a) | 99.01% |
| HPLC (w/w) | 76.61% |
| Yield of MTC | 87% |

The organic purity of the purified and recrystallized MTC product was determined by HPLC analysis and the results are summarised in the following table.

TABLE 34

HPLC Purity of Crude and Recrystallized MTC (MTC Batches 2 and 6)

| | Crude (MTC Batch 2) % (a/a) | Purified and Recrystallized (MTC Batch 6) % (a/a) |
|---|---|---|
| MTC | 98.15 | 99.01 |
| Azure B | 1.33 | 0.82 |
| Azure A | 0.09 | 0.1 |
| Azure C | — | — |
| MVB | — | — |
| MVB-CH$_3$ | — | — |
| sDMT | 0.11 | — |
| Others | 0.32 | 0.07 |
| Total | 100 | 100 |

A second batch of recrystallized MTC product was prepared using the same method. The weight loss on drying (moisture balance) was 21.54% and the accurate yield of MTC was 95%. The organic purity of crude and recrystallized MTC was determined by HPLC analysis and the results are summarised in the following table.

TABLE 35

HPLC Purity of Crude and Recrystallized MTC (Batch 4 and Batch 7)

| | Crude (MTC Batch 4) % (a/a) | Purified and Recrystallized (MTC Batch 7) % (a/a) |
|---|---|---|
| MTC | 98.09 | 98.42 |
| Azure B | 1.0 | 1.14 |
| Azure A | 0.19 | 0.24 |
| Azure C | — | <0.05 |
| MVB | — | <0.05 |
| MVB-CH$_3$ | <0.05 | — |
| sDMT | <0.05 | <0.05 |
| Others | 0.72 | 0.2 |
| Total | 100 | 100 |

Method 8

General Method for Reaction with Ketones

Thionin acetate (1 eq.) was dissolved in methanol (15 mL/mmol) under argon, and 5% palladium on carbon (0.01 eq.), glacial acetic acid (2 drops/mmol), and decaborane (0.3 eq.) were added. The mixture was heated at reflux for 30 minutes, and cooled to ambient temperature (around 20 to 25° C.). Ketone (2.2 eq.) and decaborane (0.4 eq.) were added, and the resultant mixture was stirred for 3 hours. The reaction mixture was treated with 32% aqueous hydrochloric acid (0.3 mL/mmol) and stirred for at least 3 hours before being filtered through Celite. The Celite was washed with methanol (3×10 mL), and the filtrate was evaporated to leave the crude product. If necessary, the crude product was purified.

Method 9

N,N'-di(butan-2-yl)-10H-phenothiazine-3,7-bis(aminium) Dichloride

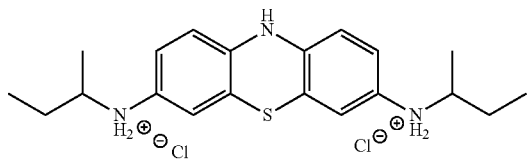 [SMILES: CCC(C)[NH2+]c1ccc2c(c1)Sc1cc([NH2+]C(C)CC)ccc1N2 ; [Cl-] ; [Cl-]]

N,N'-di(butan-2-yl)-10H-phenothiazine-3,7-bis(aminium) dichloride was prepared by the general procedure described in Method 8 above using butan-2-one. The crude product was suspended in boiling acetonitrile (40 mL) for 30 minutes, and the product was collected by evaporation of the solvent. The title compound was isolated as a green solid (537 mg, 69%). $\delta_H$ (400 MHz; CD$_3$OD) 7.12 (2H, dd, J 8.5, 2.4, ArH), 7.07 (2H, d, J 2.3, ArH), 6.80 (2H, d, J 8.6, ArH), 3.44-3.52 (2H, m, CH), 1.79-1.90 (2H, m, CH$_2$), 1.52-1.65 (2H, m, CH$_2$), 1.29 (6H, d, J 6.6, CH$_3$), 1.02 (6H, t, J 7.5, CH$_3$). $\delta_H$(400 MHz; DMSO-d6) 10.81 (4H, bs, NH$_2$+), 9.23 (1H, bs, NH), 7.09-7.16 (4H, m, ArH), 6.80 (2H, d, J 6.8, ArH), 1.69-1.80 (2H, m, CH$_2$), 1.42-1.54 (2H, m, CH$_2$), 1.17 (6H, d, J 6.4, CH$_3$), 0.89 (6H, t, J 7.5, CH$_3$). $\delta_C$ (75 MHz; CD$_3$OD) 144.4 (Ar), 129.4 (Ar), 124.5 (Ar), 122.6 (Ar), 120.2 (Ar), 116.4 (Ar), 62.0 (CH), 27.0 (CH$_2$), 16.0 (CH$_3$), 10.2 (CH$_3$). m/z (ESI) 340.1839 ([M]$^+$. C$_{20}$H$_{26}$N$_3$S requires 340.1847).

Method 10

N,N'-di(isopropyl)-10H-phenothiazine-3,7-bis(aminium) Dichloride

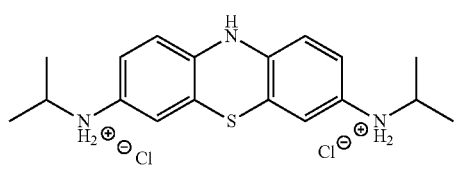 [SMILES: CC(C)[NH2+]c1ccc2c(c1)Sc1cc([NH2+]C(C)C)ccc1N2 ; [Cl-] ; [Cl-]]

N,N'-di(isopropyl)-1 OH-phenothiazine-3,7-bis(aminium) dichloride was prepared by the general procedure described in Method 8 above using acetone. No further purification was required. The title compound was isolated as a green solid (649 mg, 83%).

$\delta_H$ (400 MHz; CD$_3$OD) 7.10 (2H, dd, J 8.6, 2.4, ArH), 7.05 (2H, d, J 2.3, ArH), 6.80 (2H, d, J 8.6, ArH), 3.67 (2H, sept, J 6.5, CH), 1.34 (12H, d, J 6.5, CH$_3$). $\delta_H$ (400 MHz; DMSO-d6) 10.92 (4H, bs, NH$_2$+), 9.31 (1H, bs, NH), 7.14-7.18 (4H, m, ArH), 6.82 (2H, d, J 8.3, ArH), 3.57 (2H, sept, J 6.5, CH), 1.23 (12H, d, J 6.5, CH$_3$). $\delta_C$ (75 MHz; CD$_3$OD) 144.4 (Ar), 129.5 (Ar), 124.5 (Ar), 122.6 (Ar), 120.1 (Ar), 116.4 (Ar), 56.9 (CH), 19.20 (CH$_3$). m/z (ESI) 312.1532 ([M]$^+$. C$_{18}$H$_{22}$N$_3$S requires 312.1534).

Method 11

N,N'-di(cyclopentyl)-10H-phenothiazine-3,7-bis(aminium) Dichloride

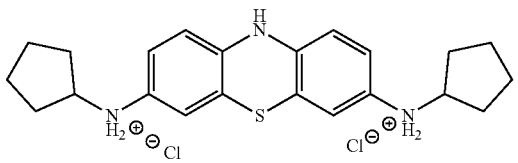 [SMILES: c1cc2c(cc1[NH2+]C1CCCC1)Sc1cc([NH2+]C3CCCC3)ccc1N2 ; [Cl-] ; [Cl-]]

N,N'-di(cyclopentyl)-10H-phenothiazine-3,7-bis(aminium) dichloride was prepared by the general procedure described in Method 8 above using cyclopentanone. The crude product was purified by dissolving in methanol (4.5 mL) and precipitating by adding acetone (18 mL). The product was collected by decanting the solvent, dissolving the residual solid in methanol, and evaporating the methanol. The title compound was isolated as a green solid (278 mg, 63%).

$\delta_H$(400 MHz; CD$_3$OD) 7.14 (2H, dd, J 8.6, 2.4, ArH), 7.08 (2H, d, J 2.4, ArH), 6.79 (2H, d, J 8.6, ArH), 3.89 (2H, quin, J 7.0, CH), 1.97-2.07 (4H, m, CH$_2$), 1.81-1.90 (4H, m, CH$_2$), 1.65-1.80 (8H, m, CH$_2$). $\delta_H$(400 MHz; DMSO-d6) 10.99 (4H, bs, NH$_2$+), 9.27 (1H, bs, NH), 7.13-7.20 (4H, m, ArH), 6.81 (2H, d, J 8.4, ArH), 3.78 (2H, quin, J 6.6, CH), 1.66-1.87 (12H, m, CH$_2$), 1.48-1.56 (4H, m, CH$_2$). $\delta_C$ (75 MHz; CD$_3$OD) 144.4 (Ar), 130.7 (Ar), 124.0 (Ar), 122.1 (Ar), 120.2 (Ar), 116.5 (Ar), 65.4 (CH), 30.6 (CH$_2$), 25.0 (CH$_2$). m/z (ESI) 364.1841 ([M]$^+$. C$_{22}$H$_{26}$N$_3$S requires 364.1847).

Method 12

N,N'-di(cyclohexyl)-10H-phenothiazine-3,7-bis(aminium) Dichloride

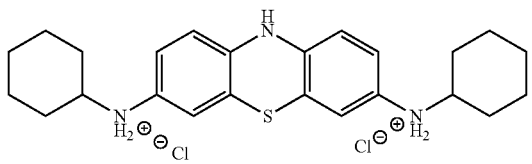 [SMILES: c1cc2c(cc1[NH2+]C1CCCCC1)Sc1cc([NH2+]C3CCCCC3)ccc1N2 ; [Cl-] ; [Cl-]]

N,N'-di(cyclohexyl)-10H-phenothiazine-3,7-bis(aminium) dichloride was prepared by the general procedure described in Method 8 above using cyclohexanone. The crude product was purified by dissolving in methanol (5.8 mL) and precipitating by adding acetone (23 mL). The product was collected by filtration, the collected solid was dissolved in methanol, and the methanol was evaporated. The title compound was isolated as a green solid (279 mg, 60%).

$\delta_H$(400 MHz; CD$_3$OD) 7.10 (2H, dd, J 8.4, 2.4, ArH), 7.06 (2H, d, J 2.3, ArH), 6.79 (2H, d, J 8.4, ArH), 3.33-3.41 (2H, m, CH), 1.96-2.06 (4H, m, CH$_2$), 1.81-1.91 (4H, m, CH$_2$), 1.65-1.73 (2H, m, CH$_2$), 1.17-1.50 (10H, m, CH$_2$). $\delta_H$(400 MHz; DMSO-d6) 10.94 (4H, bs, NH$_2$+), 9.27 (1H, bs, NH), 7.11-7.18 (4H, m, ArH), 6.81 (2H, d, J 8.3, ArH), 3.21-3.31 (2H, m, CH), 1.85-1.95 (4H, m, CH$_2$), 1.69-1.79 (4H, m, CH$_2$), 1.53-1.63 (2H, m, CH$_2$), 1.32-1.45 (4H, m, CH$_2$), 1.05-1.27 (6H, m, CH$_2$). δ$_c$ (75 MHz; CD$_3$OD) 144.4 (Ar), 129.0 (Ar), 124.5 (Ar), 122.6 (Ar), 120.1 (Ar), 116.4 (Ar), 63.1 (CH), 30.4 (CH$_2$), 25.6 (CH$_2$), 26.2 (CH$_2$). m/z (ESI) 392.2150 ([M]$^+$. C$_{2-4}$H$_{30}$N$_3$S requires 392.2160).

Method 13

3,7-bis(cyclohexylamino)phenothiazinium Chloride

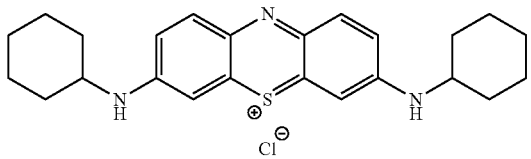 [SMILES: c1cc2nc3ccc(NC4CCCCC4)cc3[s+]c2cc1NC1CCCCC1 ; [Cl-]]

N,N'-di(cyclohexyl)-1 OH-phenothiazine-3,7-bis(aminium) dichloride (211 mg, 0.45 mmol) was dissolved in methanol (5 mL) and cooled in an ice-bath. A solution of iron(III) chloride hexahydrate (243 mg, 0.90 mmol) in methanol (1 mL) was added dropwise to the reaction mixture. The solution was stirred in an ice bath for 45 mins. The reaction mixture was concentrated under reduced pressure and the crude product was dissolved in methanol (2 mL). The solution was diluted with water (20 mL) and loaded onto a reverse-phase silica column. The iron salts were eluted with 1M aqueous HCl, and the product was eluted with methanol. The methanol was evaporated to leave 3,7-bis(cyclohexylamino)phenothiazinium chloride (180 mg, 93%) as a dark blue solid.

δ$_H$(300 MHz; CD$_3$OD) 7.83 (2H, d, J 8.7, ArH), 7.20 (4H, br s, ArH), 3.64-3.76 (2H, m, CH, 2.05 (4H, d, J 10.5, CH$_2$), 1.86 (4H, d, J 10.5, CH$_2$), 1.73 (2H, d, J 12.4, CH$_2$), 1.25-1.60 (10H, m, CH$_2$). m/z (ESI) 392.2151 ([M]$^+$. C$_{2-4}$H$_{30}$N$_3$S requires 392.2160).

The foregoing has described the principles, preferred embodiments, and modes of operation of the present invention. However, the invention should not be construed as limited to the particular embodiments discussed. Instead, the above-described embodiments should be regarded as illustrative rather than restrictive. It should be appreciated that variations may be made in those embodiments by workers skilled in the art without departing from the scope of the present invention.

REFERENCES

A number of publications are cited herein in order to more fully describe and disclose the invention and the state of the art to which the invention pertains. Full citations for these references are provided below. Each of these references is incorporated herein by reference in its entirety into the present disclosure, to the same extent as if each individual reference was specifically and individually indicated to be incorporated by reference.

Bondareff et al., 1994, J. Neuropath. Exper. Neurol., Vol. 53, No. 2, pp. 158-164.
Booth et al., 2001, "Tricyclic compounds and method of treating herpes virus", international patent publication number WO 01/51479 A2, published 19 Jul. 2001.
Epstein et al., 1941, "A Spectrophotometric Study of Thionine", Journal of Optical Society of America, Vol. 31, pp. 77-84.
Fiedeldei, 1994, "Verfahren zur Herstellung reiner Phenothiazinfarbstoffe", German Patent No DE 4302013 C1, published 1 Jun. 1994.
Galey et al., 2010, "Novel diaminophenothiazine compounds, a method for preparing same and uses thereof", US patent publication number US 2010/0204215 A1 published 12 Aug. 2010.
Goedert et al., 1989a, EMBO J., Vol. 8, pp. 393-399.
Goedert et al., 1989b, Neuron, Vol. 3, pp. 519-526.
Guttmann and Ehrlich, 1891, "Uber die wirkung des methylenblau bei malaria," Berl. Klin. Woschenr., Vol. 28, pp. 953-956.
Jakes et al., 1991, EMBO J., Vol. 10, pp. 2725-2729.
Jung et al., 2003, Tetrahedron, Vol. 59, pp. 10331-10338.
Kang et al., 1987, Nature, Vol. 325, p. 733.
Lai et al., 1995, Neurobiology of Ageing, Vol. 16, No. 3, pp. 433-445.
Marshall et al., 2012, "Phenothiazine Diaminium Salts and Their Use", international (PCT) patent publication number WO 2012/107706 A1 published 16 Aug. 2012.
May et al., 2004, Am J Physiol Cell Physiol, Vol. 286, pp. C1390-C1398.
Mena et al., 1995, Acta Neuropathol., Vol. 89, pp. 50-56.
Mena et al., 1996, Acta Neuropathol., Vol. 91, pp. 633-641.
Michaelis et al., 1940, "Semiquinone Radicals of the Thiazines", Journal of the American Chemical Society, Vol. 62, pp. 204-211.
Mukaetova-Ladinska et al., 1993, Am J Pathol. Vol. 143, No. 2, pp. 565-578.
Mukaetova-Ladinska et al., 2000, Am. J. Pathol., Vol. 157, No. 2, pp. 623-636.
Novak et al., 1993, EMBO J., Vol. 12, pp. 365-370.
Rengelshausen et al., 2004, "Pharmacokinetic interaction of chloroquine and methylene blue combination against malaria," European Journal of Clinical Pharmacology, Vol. 60, pp. 709-715.
Schirmer et al., 2003, "Methylene blue as an antimalarial agent," Redox Report, Vol. 8, pp. 272-275.
Schweiger et al., 2005, "Methods of [11C]-radiolabelling phenothiazine and phenothiazine-like compounds", international (PCT) patent publication number WO 2005/030676 A1, published 7 Apr. 2005.
Tomilin et al., 1996, "Cation Radicals of N-substituted Phenothiazines", Chemistry of Heterocyclic Compounds, Vol. 32, No. 3, pp. 365-370.
Wildes et al., 1978, "Correlation of Open-Circuit Voltage and Short-Circuit Current of the Totally Illuminated, Thin-Layer Iron-Thionine Photogalvanic Cell with Photostationary Composition", Journal of the American Chemical Society, Vol. 100, No. 21, pp. 6568-6572.
Wischik et al., 1988a, PNAS USA, Vol. 85, pp. 4506-4510.
Wischik et al., 1988b, PNAS USA, Vol. 85, pp. 4884-4888.
Wischik et al., 1996a, PNAS USA, Vol. 93, pp. 11213-11218.
Wischik et al., 1996b, "Inhibition of Tau-Tau-Association", international (PCT) patent publication number WO 96/30766 A1, published 3 Oct. 1996.
Wischik et al., 1997, in "Brain microtubule-associated proteins: modifications in disease", Eds. Avila, J., Brandt, R. and Kosik, K. S. (Harwood Academic Publishers, Amsterdam) pp. 185-241.
Wischik et al., 2001, in "Neurobiology of Alzheimer's Disease", 2nd Edition, 2001, Eds.
Dawbarn, D. and Allen, S. J., The Molecular and Cellular Neurobiology Series, Bios Scientific Publishers, Oxford).
Wischik et al., 2002, "Materials and Methods Relating to Protein Aggregation in Neurodegenerative Disease", international (PCT) patent publication number WO 02/055720 A2, published 18 Jul. 2002.

Wischik et al., 2007, "3,6-Diamino-10H-phenothiazine Salts and Their Use", international (PCT) patent publication number WO 2007/110627 A2 published 4 Oct. 2007.

Wischik et al., 2007, "Thioninium Compounds and Their Use", international (PCT) patent publication number WO 2007/110630 A1, published 4 Oct. 2007.

Wischik et al., 2008, "Methods of Synthesis and/or Purification of Diaminophenothiazinium Compounds", international (PCT) patent publication number WO 2008/007074 A2 published 17 Jan. 2008.

Wischik et al., 2012, "Phenothiazine Diaminium Salts and Their Use", international (PCT) patent publication number WO 2012/107706 A1 published 16 Aug. 2012.

The invention claimed is:

1. A method of synthesis of a compound of Formula (1):

Formula (1)

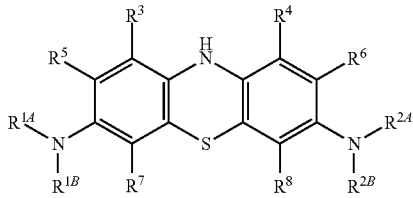

comprising the step of:
reductive amination, in which a compound of Formula (4):

Formula (4)

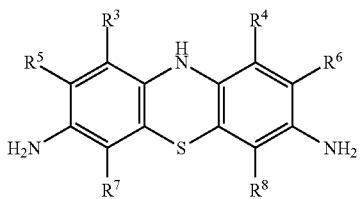

is reacted with aldehyde/ketone and a reductive amination agent,
under reductive amination conditions,
to give the corresponding compound of Formula (1),
wherein a carbonyl group, (O=)C<, of the aldehyde/ketone gives rise to a corresponding nitrogen substituent, —CH<;
wherein:
$R^{1A}$ is independently a substituent with one point of attachment, wherein the attachment is via a —CH< group; and
$R^{1B}$ is independently H or a substituent with one point of attachment, wherein the attachment is via a —CH< group;
or
$R^{1A}$ and $R^{1B}$, taken together, form a substituent with two points of attachment, wherein each of the attachments is via a —CH< group;
$R^{2A}$ is independently a substituent with one point of attachment, wherein the attachment is via a —CH< group; and $R^{2B}$ is independently H or a substituent with one point of attachment, wherein the attachment is via a —CH< group;
or
$R^{2A}$ and $R^{2B}$, taken together, form a substituent with two points of attachment, wherein each of the attachments is via a —CH< group;
and wherein:
$R^3$ is independently —H, —$R^{T3}$, —$R^{T3H}$, —F, —Cl, —Br, —I, —OH, —$OR^{T3}$, —$NH_2$, —$NHR^{T3}$, —$NR^{T3}_2$, pyrrolidino, piperidino, morpholino, —C(=O)OH, or —C(=O)$OR^{T3}$; wherein each —$R^{T3}$ is a $C_{1-10}$alkyl group and $R^{T3H}$ is a $C_{1-10}$haloalkyl group; and
$R^4$ is independently —H, —$R^{T4}$, —$R^{T4H}$, —F, —Cl, —Br, —I, —OH, —$OR^{T4}$, —$NH_2$, —$NHR^{T4}$, —$NR^{T4}_2$, pyrrolidino, piperidino, morpholino, —C(=O)OH, or —C(=O)$OR^{T4}$; wherein each —$R^{T4}$ is a $C_{1-10}$alkyl group and $R^{T4H}$ is a $C_{1-10}$haloalkyl group;
and wherein:
$R^5$ is independently —H, —$R^{T5}$, —$R^{T5H}$, —F, —Cl, —Br, —I, —OH, —$OR^{T5}$, —$NH_2$, —$NHR^{T5}$, —$NR^{T5}_2$, pyrrolidino, piperidino, morpholino, —C(=O)OH, or —C(=O)$OR^{T5}$; wherein each —$R^{T5}$ is a $C_{1-10}$alkyl group and $R^{T5H}$ is a $C_{1-10}$haloalkyl group; and
$R^6$ is independently —H, —$R^{T6}$, —$R^{T6H}$, —F, —Cl, —Br, —I, —OH, —$OR^{T6}$, —$NH_2$, —$NHR^{T6}$, —$NR^{T6}_2$, pyrrolidino, piperidino, morpholino, —C(=O)OH, or —C(=O)$OR^{T6}$; wherein each —$R^{T6}$ is a $C_{1-10}$alkyl group and $R^{T6H}$ is a $C_{1-10}$haloalkyl group;
and wherein:
$R^7$ is independently —H, —$R^{T7}$, —$R^{T7H}$, —F, —Cl, —Br, —I, —OH, —$OR^{T7}$, —$NH_2$, —$NHR^{T7}$, —$NR^{T7}_2$, pyrrolidino, piperidino, morpholino, —C(=O)OH, or —C(=O)$OR^{T7}$; wherein each —$R^{T7}$ is a $C_{1-10}$alkyl group and $R^{T7H}$ is a $C_{1-10}$haloalkyl group; and
$R^8$ is independently —H, —$R^{T8}$, —$R^{T8H}$, —F, —Cl, —Br, —I, —OH, —$OR^{T8}$, —$NH_2$, $NHR^{T8}$, —$NR^{T8}_2$, pyrrolidino, piperidino, morpholino, —C(=O)OH, or —C(=O)$OR^{T8}$; wherein each —$R^{T8}$ is a $C_{1-10}$alkyl group and $R^{T8H}$ is a $C_{1-10}$haloalkyl group,;
$R^4$ is independently —H, —$R^{T4}$, —$R^{T4H}$, —F, —Cl, —Br, —I, —OH, —$OR^{T4}$, —$NH_2$, —$NHR^{T4}$, —$NR^{T4}_2$, pyrrolidino, piperidino, morpholino, —C(=O)OH, or —C(=O)$OR^{T4}$; wherein each —$R^{T4}$ is a $C_{1-10}$alkyl group and $R^{T4H}$ is a $C_{1-10}$haloalkyl group;
and wherein:
$R^5$ is independently —H, —$R^{T5}$, —$R^{T5H}$, —F, —Cl, —Br, —I, —OH, —$OR^{T5}$, —$NH_2$, —$NHR^{T5}$, —$NR^{T5}_2$, pyrrolidino, piperidino, morpholino, —C(=O)OH, or —C(=O)$OR^{T5}$; wherein each —$R^{T5}$ is a $C_{1-10}$alkyl group and $R^{T5H}$ is a $C_{1-10}$haloalkyl group; and
$R^6$ is independently —H, —$R^{T6}$, —$R^{T6H}$, —F, —Cl, —Br, —I, —OH, —$OR^{T6}$, —$NH_2$, —$NHR^{T6}$, —$NR^{T6}_2$, pyrrolidino, piperidino, morpholino, —C(=O)OH, or —C(=O)$OR^{T6}$; wherein each —$R^{T6}$ is a $C_{1-10}$alkyl group and $R^{T6H}$ is a $C_{1-10}$haloalkyl group;

and wherein:
R$^7$ is
independently —H, —R$^{T7}$, —R$^{T7H}$, —F, —Cl, —Br, —I, —OH, —OR$^{T7}$, —NH$_2$, —NHR$^{T7}$, —NR$^{T7}$$_2$, pyrrolidino, piperidino, morpholino, —C(=O)OH, or —C(=O)OR$^{T7}$; wherein each —R$^{T7}$ is a C$_{1-10}$alkyl group and R$^{T7H}$ is a C$_{1-10}$haloalkyl group; and
R$^8$ is
independently —H, —R$^{T8}$, —R$^{T8H}$, —F, —Cl, —Br, —I, —OH, —OR$^{T8}$, —NH$_2$, —NHR$^{T8}$, —NR$^{T8}$$_2$, pyrrolidino, piperidino, morpholino, —C(=O)OH, or —C(=O)OR$^{T8}$; wherein each —R$^{T8}$ is a C$_{1-10}$alkyl group and R$^{T8H}$ is a C$_{1-10}$haloalkyl group.

2. A method according to claim 1, wherein:
R$^{1A}$ is —CH(R$^{1AX}$)(R$^{1AY}$); and
R$^{1B}$ is independently —H or —CH(R$^{1BX}$)(R$^{1BY}$); or
R$^{1A}$ and R$^{1B}$, taken together, form —CH$_2$—R$^{1AB}$—CH$_2$—;
wherein:
R$^{1AX}$ is independently —H, C$_{1-10}$alkyl, C$_{3-6}$cycloalkyl, or C$_{6-10}$carboaryl; and
R$^{1AY}$ is independently —H, C$_{1-10}$alkyl, C$_{3-6}$cycloalkyl, or C$_{6-10}$carboaryl; or
R$^{1AX}$ and R$^{1AY}$, taken together, form C$_{4-6}$alkylene;
and wherein:
R$^{1BX}$ is independently —H, C$_{1-10}$alkyl, C$_{3-6}$cycloalkyl, or C$_{6-10}$carboaryl; and
R$^{1BY}$ is independently —H, C$_{1-10}$alkyl, C$_{3-6}$cycloalkyl, or C$_{6-10}$carboaryl; or
R$^{1BX}$ and R$^{1BY}$, taken together, form C$_{4-6}$alkylene;
and wherein:
R$^{1AB}$ is C$_{2-4}$alkylene;
and wherein:
R$^{2A}$ is —CH(R$^{2AX}$)(R$^{2AY}$); and
R$^{2B}$ is independently —H or —CH(R$^{2BX}$)(R$^{2BY}$); or
R$^{2A}$ and R$^{2B}$, taken together, form —CH$_2$—R$^{2AB}$—CH$_2$—;
wherein:
R$^{2AX}$ is independently —H, C$_{1-10}$alkyl, C$_{3-6}$cycloalkyl, or C$_{6-10}$carboaryl; and
R$^{2AY}$ is independently —H, C$_{1-10}$alkyl, C$_{3-6}$cycloalkyl, or C$_{6-10}$carboaryl; or
R$^{2AX}$ and R$^{2AY}$, taken together, form C$_{4-6}$alkylene;
and wherein:
R$^{2BX}$ is independently —H, C$_{1-10}$alkyl, C$_{3-6}$cycloalkyl, or C$_{6-10}$carboaryl; and
R$^{2BY}$ is independently —H, C$_{1-10}$alkyl, C$_{3-6}$cycloalkyl, or C$_{6-10}$carboaryl; or
R$^{2BX}$ and R$^{2BY}$, taken together, form C$_{4-6}$alkylene;
and wherein:
R$^{2AB}$ is C$_{2-4}$alkylene;
wherein:
if (a):
R$^{1A}$ is —CH(R$^{1AX}$)(R$^{1AY}$); and
R$^{1B}$ is independently —H or —CH(R$^{1BX}$)(R$^{1BY}$);
R$^{2A}$ is —CH(R$^{2AX}$)(R$^{2AY}$); and
R$^{2B}$ is independently —H or —CH(R$^{2BX}$)(R$^{2BY}$);
then the aldehyde/ketone comprises:
R$^{1AX}$—C(=O)—R$^{1AY}$, and
R$^{2AX}$—C(=O)—R$^{2AY}$;
and further if R$^{1B}$ is other than —H, then the aldehyde/ketone further comprises:
R$^{1BX}$—C(=O)—R$^{1BY}$;
and further if R$^{2B}$ is other than —H, then the aldehyde/ketone further comprises:
R$^{2BX}$—C(=O)—R$^{2BY}$;

and if (b):
R$^{1A}$ and R$^{1B}$, taken together, form —CH$_2$—R$^{1AB}$—CH$_2$—; and
R$^{2A}$ and R$^{2B}$, taken together, form —CH$_2$—R$^{2AB}$—CH$_2$—;
then the aldehyde/ketone comprises:
(O=)CH—R$^{1AB}$—CH(=O); and
(O=)CH—R$^{2AB}$—CH(=O).

3. A method according to claim 2, wherein:
R$^{1A}$ is —CH(R$^{1AX}$)(R$^{1AY}$);
R$^{1B}$ is —CH(R$^{1BX}$)(R$^{1BY}$);
R$^{2A}$ is —CH(R$^{2AX}$)(R$^{2AY}$); and
R$^{2B}$ is —CH(R$^{2BX}$)(R$^{2BY}$);
and the aldehyde/ketone comprises:
R$^{1AX}$—C(=O)—R$^{1AY}$;
R$^{2AX}$—C(=O)—R$^{2AY}$;
R$^{1BX}$—C(=O)—R$^{1BY}$; and
R$^{2BX}$—C(=O)—R$^{2BY}$.

4. A method according to claim 3, wherein:
R$^{1A}$ and R$^{2A}$ are the same; and
R$^{1B}$ and R$^{2B}$ are the same.

5. A method according to claim 4, wherein:
R$^{1A}$ and R$^{2A}$ are the same;
R$^{1B}$ and R$^{2B}$ are the same; and
R$^{1A}$ and R$^{1B}$ are the same.

6. A method according to claim 2, wherein:
R$^{1A}$ is —CH$_3$;
R$^{1B}$ is —CH$_3$;
R$^{2A}$ is —CH$_3$; and
R$^{2B}$ is —CH$_3$;
and the aldehyde/ketone comprises formaldehyde.

7. A method according to claim 3, wherein the amount of aldehyde/ketone is about 4 equivalents.

8. A method according to claim 1, wherein:
R$^3$ is independently H, C$_{1-4}$alkyl, or C$_{1-4}$haloalkyl;
R$^4$ is independently H, C$_{1-4}$alkyl, or C$_{1-4}$haloalkyl;
R$^5$ is independently H, C$_{1-4}$alkyl, or C$_{1-4}$haloalkyl;
R$^6$ is independently H, C$_{1-4}$alkyl, or C$_{1-4}$haloalkyl;
R$^7$ is independently H, C$_{1-4}$alkyl, or C$_{1-4}$haloalkyl; and
R$^8$ is independently H, C$_{1-4}$alkyl, or C$_{1-4}$haloalkyl.

9. A method according to claim 1, wherein:
R$^3$ is H;
R$^4$ is H;
R$^5$ is H;
R$^6$ is H;
R$^7$ is H; and
R$^8$ is H.

10. A method according to claim 1, wherein:
the reductive amination agent is gaseous hydrogen; and
the reductive amination conditions include the presence of a hydrogenation catalyst.

11. A method according to claim 10, wherein the hydrogenation catalyst is a palladium-based hydrogenation catalyst.

12. A method according to claim 1, wherein:
the reductive amination agent is decaborane; and
the reductive amination conditions include the presence of a hydrogenation catalyst.

13. A method according to claim 12, wherein the hydrogenation catalyst is a palladium-based hydrogenation catalyst.

14. A method according to claim 1, wherein the method further comprises a preceding step of:
nitro reduction, in which a compound of Formula (5):

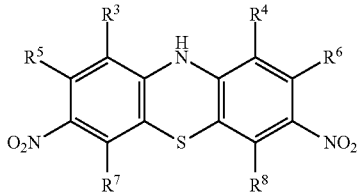

Formula (5)

is reacted with a nitro reducing agent,
under nitro reducing conditions,
to give the corresponding compound of Formula (4):

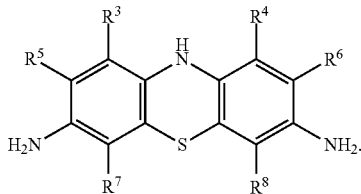

Formula (4)

15. A method according to claim 14, wherein:
the nitro reducing agent is gaseous hydrogen; and
the nitro reducing conditions include the presence of a hydrogenation catalyst.

16. A method according to claim 15, wherein the hydrogenation catalyst is a palladium-based hydrogenation catalyst.

17. A method according to claim 14, wherein the method further comprises a preceding step of:
nitration, in which a compound of Formula (6):

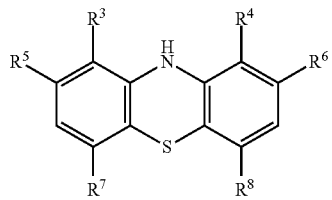

Formula (6)

is reacted with a nitration agent,
under nitration conditions,
to give the corresponding compound of Formula (5):

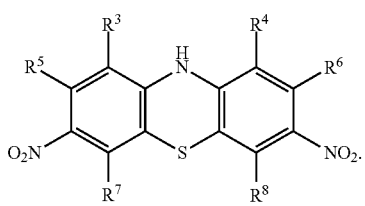

Formula (5)

18. A method according to claim 1, wherein the method further comprises a preceding step of:
thionine reduction, in which a compound of Formula (7):

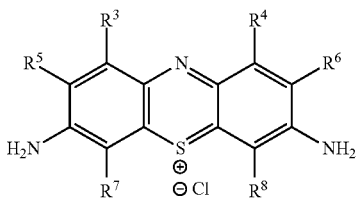

Formula (7)

is reacted with a thionine reducing agent,
under thionine reducing conditions,
to give the corresponding compound of Formula (4):

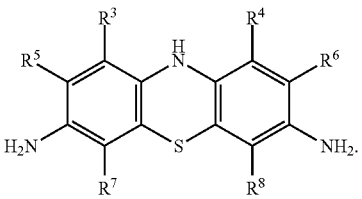

Formula (4)

19. A method according to claim 18, wherein the method further comprises a preceding step of:
ring formation, in which compounds of Formula (8) and Formula (9):

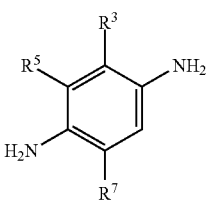

Formula (8)

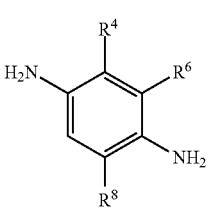

Formula (9)

are reacted with an oxidizing agent and a sulfide,
under ring forming conditions,
to give the corresponding compound of Formula (7):

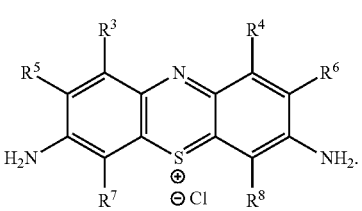

Formula (7)

20. A method of synthesis of a compound of Formula (2):

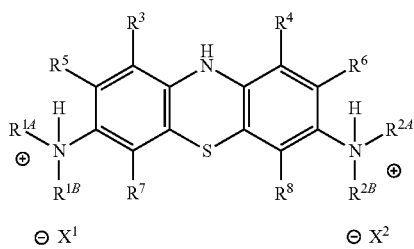

Formula (2)

wherein:
  each of $X^{1(-)}$ and $X^{2(-)}$ is independently a singly-charged anion corresponding to the acid; or
  $X^{1(-)}$ and $X^{2(-)}$, taken together, form a doubly-charged anion corresponding to the acid;
comprising a method according to claim 1;
and further comprising the subsequent step of:
di-salt formation, in which a compound of Formula (1):

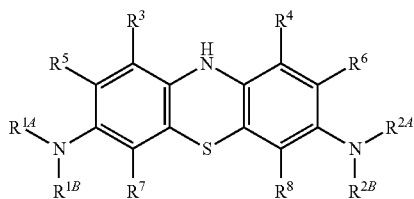

Formula (1)

is dissolved in solvent and reacted with acid,
under salt forming conditions,
to give the corresponding compound of Formula (2).

21. A method according to claim 20, wherein:
  $X^{1(-)}$ is independently $F^-$, $Cl^-$, $Br^-$, $NO_3^-$, $NO_2^-$, or $R^{X1}SO_3^-$; and
  $X^{2(-)}$ is independently $F^-$, $Cl^-$, $Br^-$, $NO_3^-$, $NO_2^-$, or $R^{X2}SO_3^-$; or
  $X^{1(-)}$ and $X^{2(-)}$, taken together, form $SO_4^{2-}$ or $R^Y(SO_3)_2^{2-}$;

wherein:
  $R^{X1}$ is independently $C_{1-10}$alkyl, $C_{1-10}$haloalkyl, $C_{3-6}$cycloalkyl, or $C_{6-10}$carboaryl;
  $R^{X2}$ is independently $C_{1-10}$alkyl, $C_{1-10}$haloalkyl, $C_{3-6}$cycloalkyl, or $C_{6-10}$carboaryl;
and
  $R^Y$ is independently $C_{1-6}$alkylene or $C_{6-10}$carboarylene;
wherein:
  each $C_{3-6}$cycloalkyl, each $C_{6-10}$carboaryl, and each $C_{6-10}$carboarylene is optionally substituted with one or more $C_{1-4}$alkyl groups.

22. A method of synthesis of a compound of Formula (3):

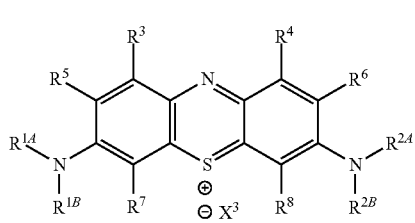

Formula (3)

wherein:
  $X^{3(-)}$ is an anion corresponding to the acid;
comprising a method according to claim 1;
and further comprising the subsequent step of:
thiazine oxidation, in which a compound of Formula (1):

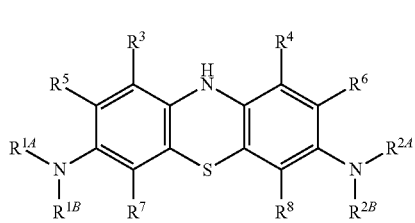

Formula (1)

is reacted with an oxidizing agent and an acid;
under oxidizing conditions,
to give the corresponding compound of Formula (3).

23. A method according to claim 22, wherein the oxidizing agent is Fe(III) chloride.

* * * * *